US008987192B2

(12) United States Patent
Bielicki et al.

(10) Patent No.: US 8,987,192 B2
(45) Date of Patent: *Mar. 24, 2015

(54) POTENT AND SELECTIVE MEDIATORS OF CHOLESTEROL EFFLUX

(75) Inventors: John K. Bielicki, San Ramon, CA (US); Jan Johansson, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 1591 days.

This patent is subject to a terminal disclaimer.

(21) Appl. No.: 12/519,116

(22) PCT Filed: Dec. 13, 2007

(86) PCT No.: PCT/US2007/087477
§ 371 (c)(1),
(2), (4) Date: Sep. 30, 2009

(87) PCT Pub. No.: WO2008/115303
PCT Pub. Date: Sep. 25, 2008

(65) Prior Publication Data
US 2012/0329703 A1    Dec. 27, 2012

Related U.S. Application Data

(60) Provisional application No. 60/874,909, filed on Dec. 13, 2006.

(51) Int. Cl.
| | |
|---|---|
| *A61K 38/00* | (2006.01) |
| *A61K 38/16* | (2006.01) |
| *A61K 45/00* | (2006.01) |
| *A61K 47/24* | (2006.01) |
| *A61K 49/00* | (2006.01) |
| *A61K 51/00* | (2006.01) |
| *A61K 9/127* | (2006.01) |
| *C07K 14/00* | (2006.01) |
| *C07K 14/47* | (2006.01) |
| *C07K 14/705* | (2006.01) |
| *A61P 3/06* | (2006.01) |
| *A61P 9/00* | (2006.01) |
| *C07K 14/775* | (2006.01) |

(52) U.S. Cl.
CPC ............ *C07K 14/775* (2013.01); *C07K 14/4703* (2013.01); *A61K 38/16* (2013.01); *A61K 38/00* (2013.01)
USPC ........... 514/1.9; 514/16.4; 514/7.4; 514/21.4; 530/325

(58) Field of Classification Search
CPC ... A61K 38/00; A61K 38/16; C07K 14/4703; C07K 14/775
USPC .................. 514/16.4, 1.9, 21.4, 7.4; 530/325
See application file for complete search history.

(56) References Cited

U.S. PATENT DOCUMENTS

| | | |
|---|---|---|
| 2004/0058869 A1 | 3/2004 | Hayden et al. |
| 2005/0202532 A1 | 9/2005 | Bielicki et al. |
| 2008/0096815 A1 | 4/2008 | Fogelman et al. |
| 2008/0234192 A1 | 9/2008 | Heinecke et al. |

FOREIGN PATENT DOCUMENTS

| | | |
|---|---|---|
| WO | WO 2005/058938 | 6/2005 |
| WO | WO 2006/020040 | 2/2006 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Ramprasad et al., "Sustained-delivery of an apolipoprotein E-peptidomimetic using multivesicular liposomes lowers serum cholesterol levels," 2002, Journal of Controlled Release, 79, 207-218.
Song et al., "Effects of L- or D-Pro incorporation into hydrophobic or hydrophilic helix face of amphipathic alpha-helical model peptide on structure and cell selectivity," 2004, Biochemical and Biophysical Research Communications, 314, 615-621.
Sparrow et al., "Apolipoprotein E: phospholipid binding studies with synthetic peptides from the carboxyl terminus," 1992, Biochemistry, 31, 1065-1068.

* cited by examiner

*Primary Examiner* — James H Alstrum Acevedo
*Assistant Examiner* — Erinne Dabkowski
(74) *Attorney, Agent, or Firm* — Kilpatrick Townsend & Stockton LLP

(57) ABSTRACT

The present invention provides a family of non-naturally occurring polypeptides having cholesterol efflux activity that parallels that of full-length apolipoproteins (e.g., Apo AI and Apo E), and having high selectivity for ABAC1 that parallels that of full-length apolipoproteins. The invention also provides compositions comprising such polypeptides, methods of identifying, screening and synthesizing such polypeptides, and methods of treating, preventing or diagnosing diseases and disorders associated with dyslipidemia, hypercholesterolemia and inflammation.

28 Claims, 25 Drawing Sheets

Table 1 - Cholesterol efflux efficiency

| | Km values | |
|---|---|---|
| | µg/ml | µM |
| *apoAI | 3.4±0.6 | 0.12±0.02 |
| apoE3 | 4.5±0.8 | 0.13±0.02 |
| CT | 2.5±0.2 | 0.21±0.02 |
| SEQ ID:4 | 0.86±0.3 | 0.26±0.12 |
| SEQ ID:5 | 0.84±0.2 | 0.25±0.10 |
| SEQ ID:6 | 0.72±0.1 | 0.21±0.03 |

*apoA-I and E refer to the full-length proteins
CT refers to the C-terminal domain aa192-299 of apoE3
Values are means±SD

FIGURE 3

POTENT AND SELECTIVE MEDIATORS OF CHOLESTEROL EFFLUX

CROSS-REFERENCES TO RELATED APPLICATIONS

This application is the U.S. National Stage entry of International Application No. PCT/US2007/087477, filed Dec. 13, 2007, which claims the benefit of U.S. Provisional Patent Applications: 60/874,909, filed on Dec. 13, 2006, the disclosures of which are herein incorporated by reference in their entirety for all purposes.

Subject matter in this application is also related to U.S. Patent Application No. 20050202532, filed Dec. 15, 2004, which is a continuation in part of U.S. patent application Ser. No. 10/142,238, filed May 8, 2002, and claims the benefit of U.S. Provisional Patent Application No. 60/529,933, filed Dec. 15, 2003, the disclosures of all of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Grant (Contract) No. R03-AG023153 awarded by the National Institutes of Aging. The Government has certain rights in this invention.

The research leading to this invention was also funded by a sponsored research agreement with Artery Therapeutics, Inc. (LBNL Work for Other Agreement No. LB05-001119) and by Grant No. 13IT-0025 awarded by the Tobacco Related Disease Research Program of the State of California.

BACKGROUND OF THE INVENTION

Cardiovascular disease (CVD) is a leading cause of morbidity and mortality in the United States and throughout the world. The accumulation of cholesterol in macrophages in the artery wall promotes foam-cell formation and atherosclerosis constituting a main cause of CVD (Schmitz, G. and Kaminski, W. E., "ATP-binding cassette (ABC) transporters in atherosclerosis," *Curr Atheroscler Rep.*, 4(3):243-51 (2002). Cholesterol accumulation in macrophages is largely dependent on the balance between the deposition by Apolipoprotein B-containing lipoprotein particles, such as VLDL, IDL and LDL, and the cholesterol removal by ApoA-I and ApoE particles. Lowering of plasma LDL concentrations by statins and other cholesterol lowering medications prevents approximately one-third of the CVD events, while two-thirds of the events remain (see, e.g., "Randomized trial of cholesterol lowering in 4444 patients with coronary heart disease: the Scandinavian Simvastatin Survival Study (4S), *Lancet*, 344 (8934):1383-1389 (1994); and "Influence of pravastatin and plasma lipids on clinical events in the West of Scotland Coronary Prevention Study (WOSCOPS), *Circulation*, 197(15): 1440-5 (1998). The latter constitutes a huge unmet medical need.

Elevated levels of plasma HDL cholesterol are associated with reduced risk of atherosclerosis (Gordon et al., "High Density Lipoprotein As A Protective Factor Against Coronary Heart Disease," *Am. J. Med.*, 62:707-14 (1977)). Recent epidemiological studies have been able to ascribe the HDL protective effect to its main apolipoprotein, Apo A-I (Walldius, G, et al., High Apolipoprotein B, Low Apolipoprotein A-I, And Improvement In The Prediction of Fatal Myocardial Infarction (AMORIS study): A Prospective Study," *Lancet*, 358(9298):2026-33 (2001); and Yusuf et al., "Effect of Potentially Modifiable Risk Factors Associated With Myocardial Infarction in 52 Countries (the INTERHEART study): Case-control Study," *Lancet*, 364(9438):937-52 (2004)). The beneficial effects of HDL are related, in part, to activity in mediating the anti-atherogenic reverse cholesterol transport (RCT) pathway. RCT involves the transport of cholesterol from peripheral macrophages to the liver for excretion of sterol in feces (Lewis et al., "New Insights Into The Regulation of HDL Metabolism and Reverse Cholesterol Transport," *Circ. Res.*, 96:1221-32 (2005)). The rate-limiting step of RCT involves stimulation of cholesterol efflux from macrophages, mediated by native apolipoproteins such as Apo A-I and Apo E. This process of cholesterol efflux generates nascent HDL and requires the ATP-binding cassette transporter A1 (ABCA1) or else atherosclerosis is developed (Calpe-Berdiel et al., "Direct Evidence In Vivo of Impaired Macrophage-Specific Reverse Cholesterol Transport in ATP-Binding Cassette Transporter A1-Deficient Mice," *Biochim. Biophys. Acta.*, 1738(1-3):6-9 (2005). ABCA1 is the defective molecule in Tangiers disease, which is characterized by severe deficiency in plasma HDL and premature atherosclerosis (Attie et al., "Pivotal Role of ABCA1 in Reverse Cholesterol Transport Influencing HDL Levels and Susceptibility to Atherosclerosis," *J Lipid Res.*, 42(11):1717-26 (2001)). Apolipoproteins A and E also stabilize cellular ABCA1 protein by preventing its degradation, which ensures high-levels of cellular cholesterol export and HDL assembly.

The clinical importance of HDL has sparked interest in the development of strategies to manipulate RCT for therapeutic purposes. Explorative proof of concept studies have shown that injections with full length Apo A-I variants, e.g., proApoA-I, Apo A-I Milano, and Apo A-I 2 wild type in phospholipid complexes increases RCT (Eriksson et al., Stimulation of Fecal Steroid Excretion After Infusion of Recombinant Proapolipoprotein A-I. Potential Reverse Cholesterol Transport in Humans," *Circulation*, 100(6):594-8 (1999)), and regress coronary atherosclerosis (Nissen et al., "Effect of Recombinant ApoA-I Milano on Coronary Atherosclerosis in Patients with Acute Coronary Syndromes: A Randomized Controlled Trial," *JAMA*, 290(17):2292-300 (2003); and Tardif et al., "Effect of rHDL on Atherosclerosis-Safety and Efficacy (ERASE) Investigators," *JAMA*, 297:1675-82. Epub Mar. 26, 2007)). Albeit promising full length ApoA-I protein have several drawbacks as a therapeutics if they are to be developed into commercial products. For instance, Apo A-I is a 243 amino acid long protein that is far from trivial to produce in the quantities needed for a commercial product. In addition, Apo A-I variants, such as the Milano and Paris variants, may evoke immunologic responses due to their foreign nature.

Thus, there is a need in the art for additional compositions and methods utilizing the potent RCT pathway to mediate cholesterol efflux for stabilizing and regressing atherosclerotic plaques, i.e., for treating cardiovascular disease. Surprisingly, the present invention fulfills this need as well as other needs by providing such compositions and methods.

SUMMARY OF THE INVENTION

The present invention relates to peptides that have effects on lipids metabolism. Lipids are an important cell structural component and provide source material for fundamental cell signaling including prostaglandins, reactive oxidative species, and the like. Through signaling pathways, lipids also contribute to the orchestration of cytokine responses, e.g., to inflammatory stimuli. Such lipid effects are implicated in several disease states including but not limited to atherosclerosis, and neurological, inflammatory and infectious disease manifestations. The peptides exert their effects directly or through mediators. Mediators include, but are not limited to, HDL, ABC transporters, and mediators for oxidation and inflammation.

In one aspect, the invention therefore provides a family of polypeptides having cholesterol efflux activity that parallels, and preferably exceeds on a weight basis, that of full-length apolipoproteins (e.g., Apo AI and Apo E); and having high selectivity for ABAC1 that parallels that of full-length apolipoproteins. More particularly, the present invention provides a family of non-naturally occurring polypeptides that act as high-affinity functional ligands for ABCA1 and that stimulate cellular cholesterol efflux with approximately the capacity and potency of native apolipoproteins on a per molecule basis. The polypeptides of the present invention stimulate cholesterol efflux from macrophage foam cells in vivo, promote a sustained increase in fecal sterol secretion, and reduce the severity of established atherosclerosis in the presence of hypercholesterolemia and a high-fat dietary insult in an apolipoprotein E-deficient mouse model of disease, and also prevent atherosclerosis development in a LDL receptor-deficient mouse model.

As such, the polypeptides of the present invention, i.e., polypeptides that have potent and selective activity for ABCA1, can be used therapeutically to promote ABCA1-stabilization as well as ABCA1-lipid efflux activity, and can be used alone or, alternatively, in combination with other known pharmacological agents for the treatment of cardiovascular disease to reduce atherosclerosis. In addition, the polypeptides of the present invention can be used alone or, alternatively, in combination with other known pharmacological agents for the treatment of acute coronary syndrome to reduce plaque lipid content and to stabilize vulnerable plaques. Further, the polypeptides of the present invention can be used alone or, alternatively, in combination with other known pharmacological agents for the treatment of dyslipidemia, hypercholesterolemia and inflammation to raise plasma HDL concentrations and/or to promote reverse cholesterol transport.

The peptides of the invention comprise certain features that together define the pharmacokinetic and pharmacodynamic properties of the peptides. These features include an α-helix structure and amphipathic orientation of amino acids along the axis of the α-helix structure. The peptides comprise two separate acidic residue foci along the hydrophilic axis. The α-helix structure is further enforced by natural amino acid salt bridge formation in the lipid-water inter phase. The peptides also lack substantial stereo-specific effect, e.g., peptides that comprise L and D amino acids and inverted forms work equally well. The peptides comprise a core sequence of 24 amino acid residues that selectively bind to HDL in plasma and target the ABCA1 transporter in cells.

Pharmacodynamics are facilitated by the hydrophobic properties, e.g., the hydrophobic wedge angle along the axis of the α-helix positions the peptide in the cell membrane in the vicinity of the ABCA1 transporter, thereby allowing functional interaction. Thus the peptides interact with cell membranes in a physiological way in that they confer ABCA1 specific lipid efflux with minimal non-specific cell membrane effects.

In one aspect, the present invention provides an isolated polypeptide comprising the following amino acid sequence:

(SEQ ID NO: 11)
$X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$ wherein: $X_1$, $X_7$, $X_8$, $X_{15}$, $X_{18}$ and $X_{19}$ are amino acids independently selected from the group consisting of E and D; $X_2$, $X_6$, $X_9$, $X_{10}$, $X_{12}$, $X_{13}$, $X_{16}$, $X_{17}$, $X_{20}$, $X_{21}$ and $X_{24}$ are amino acids independently selected from the group consisting of A, V, L, I, F, W, M and P; $X_3$, $X_5$, $X_{14}$ and $X_{23}$ are amino acids independently selected from the group consisting of R, K, A, V, L, I, F, W, M, P, G, S, T, C, Y, N and Q, wherein at least two of $X_3$, $X_5$, $X_{14}$ and $X_{23}$ are amino acids independently selected from the group consisting of R and K; and $X_4$, $X_{11}$, and $X_{22}$ are amino acids independently selected from the group consisting of S, T, G, A and Y; wherein each letter stands for the conventional one-letter amino acid code. The polypeptides of SEQ ID NO:11 have cholesterol efflux activity, ABCA1-stabilization activity, anti-oxidant activity as well as anti-inflammatory activity.

In certain embodiments of the polypeptide of SEQ ID NO:11, $X_2$, $X_6$, $X_9$, $X_{10}$, $X_{12}$, $X_{13}$, $X_{16}$, $X_{17}$, $X_{20}$, $X_{21}$ and $X_{24}$ are amino acids independently selected from the group consisting of A, V, L, F and W and, preferably, are amino acids independently selected from the group consisting of A, L, F and W. In other embodiments of the polypeptide of SEQ ID NO:11, at least three of $X_3$, $X_5$, $X_{14}$ and $X_{23}$ are amino acids independently selected from the group consisting of R and K. In certain other embodiments, $X_3$, $X_5$, $X_{14}$ and $X_{23}$ are amino acids independently selected from the group consisting of R, K, L and F, wherein at least two of $X_3$, $X_5$, $X_{14}$ and $X_{23}$ are amino acids independently selected from the group consisting of R and K. In yet other embodiments, $X_4$, $X_{11}$, and $X_{22}$ are amino acids independently selected from the group consisting of S, A and Y and, preferably, $X_4$, $X_{11}$, and $X_{22}$ are each A.

In one aspect, the present invention provides an isolated polypeptide comprising the following amino acid sequence:

(SEQ ID NO: 1)
$X_1X_2X_3SX_5X_6X_7X_8X_9X_{10}AAX_{13}X_{14}X_{15}X_{16}X_{17}X_{18}X_{19}X_{20}LAX_{23}X_{24}$ wherein: $X_1$, $X_7$, $X_8$, $X_{15}$, $X_{18}$ and $X_{19}$ are amino acids independently selected from the group consisting of E and D; $X_2$ is an amino acid selected from the group consisting of F, V, L and W; $X_3$, $X_5$, $X_{14}$ and $X_{23}$ are amino acids independently selected from the group consisting of R and K; $X_6$, $X_9$, $X_{10}$, $X_{13}$, $X_{16}$, $X_{20}$ and $X_{24}$ are amino acids independently selected from the group consisting of L, F and W; and $X_{17}$ is an amino acid selected from the group consisting of F, A, L and W; and wherein each letter stands for the conventional one-letter amino acid code. The polypeptides of SEQ ID NO:1 have cholesterol efflux activity, ABCA1-stabilization activity, anti-oxidant activity as well as anti-inflammatory activity.

In another embodiment, the present invention provides an isolated polypeptide comprising the following amino acid sequence:

(SEQ ID NO: 2)
$X_1X_2X_3SX_5LX_7X_8WFAAFX_{14}X_{15}FX_{17}X_{18}X_{19}FLAX_{23}L$ wherein: $X_1$, $X_7$, $X_8$, $X_{15}$, $X_{18}$ and $X_{19}$ are amino acids independently selected from the group consisting of E and D; $X_2$ is an amino acid selected from the group consisting of F and V; $X_3$, $X_5$, $X_{14}$ and $X_{23}$ are amino acids independently selected from the group consisting of R and K; and $X_{17}$ is an amino acid selected from the group consisting of F and A; and wherein each letter stands for the conventional one-letter amino acid code. The polypeptides of SEQ ID NO:2 have cholesterol efflux activity, ABCA1-stabilization activity, anti-oxidant activity as well as anti-inflammatory activity.

In yet another embodiment, the present invention provides an isolated polypeptide comprising the following amino acid sequence:

$EX_2RSKLEEWFAAFREFX_{17}EEFLARLKS$, (SEQ ID NO: 3)

wherein: $X_2$ is an amino acid selected from the group consisting of F and V; and $X_{17}$ is an amino acid selected from the group consisting of F and A; and wherein each letter stands for the conventional one-letter amino acid code. The polypeptides of SEQ ID NO:3 have cholesterol efflux activity, ABCA1-stabilization activity, anti-oxidant activity as well as anti-inflammatory activity.

In one embodiment, the present invention provides isolated polypeptide of SEQ ID NOS:1-3 and 11, further comprising $X_{25}$ and $X_{26}$ at the carboxy terminus (i.e., C-terminus), wherein $X_{25}$ is an amino acid independently selected from the group consisting of R, K, A, V, L, I, F, W, M, P, G, S, T, C, Y, N and Q, and $X_{26}$ is an amino acid independently selected from the group consisting of S, T, G, A and Y. In a preferred embodiment, $X_{25}$ is K and $X_{26}$ is S. In connection with this preferred embodiment, the present invention provides, an isolated polypeptide comprising the following amino acid sequence:

$X_1X_2X_3SX_5X_6X_7X_8X_9X_{10}AAX_{13}X_{14}X_{15}X_{16}X_{17}X_{18}X_{19}X_{20}LAX_{23}X_{24}KS$ (SEQ ID NO: 8)

wherein: $X_1$, $X_7$, $X_8$, $X_{15}$, $X_{18}$ and $X_{19}$ are amino acids independently selected from the group consisting of E and D; $X_2$ is an amino acid selected from the group consisting of F, V, L and W; $X_3$, $X_5$, $X_{14}$ and $X_{23}$ are amino acids independently selected from the group consisting of R and K; $X_6$, $X_9$, $X_{10}$, $X_{13}$, $X_{16}$, $X_{20}$ and $X_{24}$ are amino acids independently selected from the group consisting of L, F and W; and $X_{17}$ is an amino acid selected from the group consisting of F, A, L and W; and wherein each letter stands for the conventional one-letter amino acid code. In addition, the present invention provides an isolated polypeptide comprising the following amino acid sequence:

$X_1X_2X_3SX_5LX_7X_8WFAAFX_{14}X_{15}FX_{17}X_{18}X_{19}FLAX_{23}LKS$ (SEQ ID NO: 9)

wherein: $X_1$, $X_7$, $X_8$, $X_{15}$, $X_{18}$ and $X_{19}$ are amino acids independently selected from the group consisting of E and D; $X_2$ is an amino acid selected from the group consisting of F and V; $X_3$, $X_5$, $X_{14}$ and $X_{23}$ are amino acids independently selected from the group consisting of R and K; and $X_{17}$ is an amino acid selected from the group consisting of F and A; and wherein each letter stands for the conventional one-letter amino acid code. Further, the present invention provides an isolated polypeptide comprising the following amino acid sequence:

$EX_2RSKLEEWFAAFREFX_{17}EEFLARLKS$, (SEQ ID NO: 10)

wherein: $X_2$ is an amino acid selected from the group consisting of F and V; and $X_{17}$ is an amino acid selected from the group consisting of F and A; and wherein each letter stands for the conventional one-letter amino acid code.

In one embodiment, the isolated polypeptide of the present invention comprises (and, in certain embodiments, consists of or, alternatively, consists essentially of) the following amino acid sequence: EVRSKLEEWFAAFREFAEEFLARLKS (SEQ ID NO:4, which is also referred to herein as "ATI-5261" or "5261") or comprises (and, in certain embodiments, consists of or, alternatively, consists essentially of) the sequence: EVRSKLEEWFAAFREFAEEFLARL (SEQ ID NO:12). In another embodiment, the isolated polypeptide comprises (and, in certain embodiments, consists of or, alternatively, consists essentially of) the following amino acid sequence: EVRSKLEEWFAAFREFFEEFLARLKS (SEQ ID NO:5, which is also referred to herein as "S1") or comprises (and, in certain embodiments, consists of or, alternatively, consists essentially of) the sequence: EVRSKLEEWFAAFREF-FEEFLARL (SEQ ID NO:13). In yet another embodiment, the isolated polypeptide comprises (and, in certain embodiments, consists of or, alternatively, consists essentially of) the following amino acid sequence: EFRSKLEEWFAAFREF-FEEFLARLKS (SEQ ID NO:6, which is also referred to herein as "S2") or comprises (and, in certain embodiments, consists of or, alternatively, consists essentially of) the sequence: EFRSKLEEWFAAFREFFEEFLARL (SEQ ID NO:14). In yet another embodiment, the isolated polypeptide comprises (and, in certain embodiments, consists of or, alternatively, consists essentially of) the following amino acid sequence: EFRSKLEEWFAAFREFAEEFLARLKS (SEQ ID NO:7, which is also referred to herein as "S3") or comprises (and, in certain embodiments, consists of or, alternatively, consists essentially of) the sequence: EFRSKLEEW-FAAFREFAEEFLARL (SEQ ID NO:15).

In another aspect, the present invention provides polypeptide variants of the polypeptides of SEQ ID NO:10. In one embodiment, the polypeptide has at least 75% identity to the amino acid sequence of SED ID NO:4. In another embodiment, the polypeptide has at least 75% identity to the amino acid sequence of SED ID NO:5. In yet another embodiment, the polypeptide has at least 75% identity to the amino acid sequence of SED ID NO:6. In still another embodiment, the polypeptide has at least 75% identity to the amino acid sequence of SED ID NO:7. In a preferred embodiment, the polypeptide has at least 75% identity, preferably 80%, 85%, 90%, 91%, 92%, 93%, 94%, 95%, 96%, 97%, 98%, 99% or 100% identity to a polypeptide of SEQ ID NO:4, 5, 6, 7, 12, 13, 14, or 15.

In one embodiment, the polypeptides of the present invention further comprise a protecting group. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. Thus, in one embodiment, the polypeptides of the present invention further comprise a protecting group coupled to the amino or carboxy terminus. In one embodiment, the polypeptides further comprise a first protecting group coupled to the amino terminus and a second protecting group coupled to the carboxyl terminus.

Suitable protecting groups include, but are not limited to, acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-butyl (tBu), and trifluoroacetyl (TFA).

In a preferred embodiment, the polypeptides comprise a first protecting group coupled to the amino terminus, the first protecting group including, but not limited to, acetyl, propionyl, and a 3 to 20 carbon alkyl. In a preferred embodiment, the first protecting group is an acetyl. In another preferred embodiment, the polypeptides comprise a second protecting group coupled to the carboxyl terminus, the second protecting being a amide.

The polypeptides of the present invention can comprise all "L" amino acids, all "D" amino acids or a mixture of "L" and "D" amino acids. It has surprisingly been found that polypeptides comprising all D-amino acids stimulate cholesterol efflux with high-capacity and high-affinity like the L-amino acid polypeptides.

In one embodiment, a polypeptide of the present invention has cholesterol efflux activity. In another embodiment, a polypeptide of the present invention has ABCA1 stabilizing activity. In yet another embodiment, a polypeptide of the present invention protects a phospholipids from oxidation by an oxidizing agent (i.e., the polypeptide has anti-oxidant activity). In still another embodiment, a polypeptide of the present invention has anti-inflammatory activity, including inhibition of adhesion molecules. In preferred embodiment, a polypeptide of the present invention comprises one or more of these activities. In even more preferred embodiments, a polypeptide of the present invention comprises each of these activities.

A further embodiment of the invention provides pharmaceutical compositions comprising at least one polypeptide described herein and a pharmaceutically acceptable carrier or excipient. In some embodiments, the pharmaceutical compositions comprise an additional therapeutic agent (e.g., a statin such as atorvastatin, lovastatin, pravastatin, simvastatin, fluvastatin, or rosuvastatin; a bile acid binder such as cholestyramine or colestipol; a Nieman-Pick C1-Like 1 sterol transporter channel inhibitor such as Ezetimibe; a platelet clumping inhibitor such as aspirin, ticlopidine, or clopidogrel, niacin/nicotinamide, a PPAR activator, Vitamin E, or combinations thereof, for treating a disease or disorder associated with cholesterol efflux (e.g., cardiovascular disease).

Another aspect of the present invention provides peptidomimetics of the polypeptides disclosed herein. In one embodiment, the present invention provides a peptidomimetic having a substantially three-dimensional conformation as a polypeptide having an amino acid sequence of SEQ ID NO:11 or SEQ ID NO:1. In another embodiment, the present invention provides a peptidomimetic having a substantially three-dimensional conformation as a polypeptide having an amino acid sequence selected from the group consisting of SEQ ID NO:2-10. In one embodiment, the peptidomimetic is a retro-inverso analog. In another embodiment, the peptidomimetic is a retro-enantio analog. In yet another embodiment, the peptidomimetic is a trans-olefin analog. As disclosed herein, the peptidomimetics of the present invention can comprise other back-bone modifications. As with the polypeptides of the present invention, the peptidomimetics of the present invention can further comprise a protecting group and, preferably, a protecting group at both the amino and carboxyl termini.

In another aspect, the invention provides an amphipatic α-helical peptide that binds to the same ABCA1 binding site as a peptide that comprises one a-helical segment and has cholesterol efflux activity, e.g., SEQ ID NO:4. The invention additionally provides an amphipatic α-helical peptide that binds to HDL. Furthermore, the invention further provides an isolated amphipatic α-helix peptide, e.g., that has a single 24 amino acid α-helix peptide element, that stimulates ABCA1-specific cholesterol efflux.

In a further aspect, the present invention provides a composition comprising a polypeptide of the present invention, such as a polypeptide having an amino acid sequence selected from the group consisting of SEQ ID NOS:1-11, or a peptidomimetic thereof complexed with a lipid. In one embodiment, the lipid is a phospholipid. In another embodiment, the phospholipids is 1-palmitoyl-2-oleoyl-sn-glycerol-3-phosphatidylcholine ("POPC"). In yet another embodiment, the composition further comprises a pharmaceutically acceptable carrier.

Yet another aspect of the invention provides methods of mediating cholesterol efflux in a mammalian subject (e.g., a primate such as a human or chimpanzee or a rodent such as a rat or mouse) by administering at least one polypeptide or peptidomimetic described herein to the subject. Those of skill in the art will appreciate that a nucleic acid encoding such a polypeptide (or peptidomimetic) can be administered to the subject in lieu of administering the polypeptide (or peptidomimetic). The present invention provides such nucleic acids. Based on their cholesterol efflux activity, the polypeptides and peptidomimetics of the present invention can be advantageously used to treat, ameliorate or prevent a disease or condition associated with dyslipidemia, hypercholesterolemia and inflammation.

Still another aspect of the present invention provides methods for treating or preventing a symptom of atherosclerosis in a mammal by administering at least one polypeptide or peptidomimetic described herein to the subject. Again, those of skill in the art will appreciate that a nucleic acid encoding such a polypeptide (or peptidomimetic) can be administered to the subject in lieu of administering the polypeptide (or peptidomimetic). Such nucleic acids are provided by the present invention. In one embodiment of this method, the mammal is a mammal diagnosed as having one or more symptoms of atherosclerosis. In another embodiment, the mammal is diagnosed as at risk for atherosclerosis. Preferably, the mammal is a human, but can also be a non-human animal. In one exemplar embodiment, the polypeptide has an amino acid sequence of SEQ ID NO:11, preferably SEQ ID NO:1 or 8, preferably, SEQ ID NO:2 or 9, more preferably, SEQ ID NO:3 or 10 and, even more preferably, an amino acid sequence of SEQ ID NO:4, 5, 6, 7, 12, 13, 14, or 15.

In another related embodiment, the methods further comprise administering at least one additional therapeutic agent. Examples of such therapeutic agents include, but are not limited to, an antibody, an enzyme inhibitor, an antibacterial agent, an antiviral agent, a steroid, a non-steroidal anti-inflammatory agent, an anti-metabolite, a cytokine, or a soluble cytokine receptor. The enzyme inhibitor may be a protease inhibitor or a cyclooxygenase inhibitor. The additional agent may be added as a part of a pharmaceutical composition, or may be administered concomitantly or within a time period when the physiological effect of the additional agent overlaps with the physiological effect of the polypeptide(s) or peptidomimetic(s) of the present invention. More specifically, an additional agent may be administered concomitantly or one week, several days, 24 hours, 8 hours, or immediately before the administration of the polypeptide(s) or peptidomimetic(s). Alternatively, an additional agent may be administered one week, several days, 24 hours, 8 hours, or immediately after the administration of the polypeptide(s) or peptidomimetic(s).

Yet another aspect of the present invention provides methods for stabilizing a vulnerable plaque, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having one or more vulnerable plaques. In another embodiment, the mammal is diagnosed as at risk for having a vulnerable plaque(s). Preferably, the mammal is a human, but can also be a non-human animal. In one exemplar embodiment, the polypeptide has an amino acid sequence of SEQ ID NO:11, preferably SEQ ID NO:1 or 8, preferably, an amino acid sequence of SEQ ID NO:2 or 9, more preferably, an amino acid sequence of SEQ ID NO:3 or 10 and, even more preferably, an amino acid sequence of SEQ ID NO:4, 5, 6 or 7.

The present invention also provides kits for treating or preventing a disease or condition associated with dyslipidemia, hypercholesterolemia or inflammation. In a preferred embodiment, the present invention provides kits for treating or preventing a symptom of atherosclerosis, the kit comprising a container containing a polypeptide or peptidomimetic of the present invention. The kit can further comprise a pharmaceutically acceptable carrier. In addition, the kit can further comprise instructional materials teaching the use of the polypeptide or peptidomimetic for treating or preventing a disease or condition associated with dyslipidemia, hypercholesterolemia or inflammation, such as atherosclerosis. The polypeptides and peptidomimetics provided in the kits of the present invention can comprise all L amino acids, all D amino acids or a mixture of L and D amino acids.

In connection with the above kits, instructional material can include a document or recorded media including a written or audible instruction for the use of a pharmaceutical composition. Instruction material includes, for example, a label on a bottle, a paper inserted in a box, printing on the box or carton, instructions provided by a website at an address given in any of these locations, etc.

In another aspect, the present invention provides methods of making a variant polypeptide having cholesterol efflux activity and/or ABCA stabilization activity, the method comprising: (a) providing a polypeptide having an amino acid sequence of SEQ ID NO:1 or SEQ ID NO:8; (b) modifying at least one amino acid position of the polypeptide to generate a polypeptide variant; (c) screening the polypeptide variant for cholesterol efflux activity and/or ABCA stabilization activity; (d) selecting the polypeptide variant that has at least 80% of the cholesterol efflux activity of the polypeptide having an amino acid sequence of SEQ ID NO:1 or SEQ ID NO:8 and/or selecting the polypeptide variant that has at least 80% of the ABCA stabilization activity of the polypeptide having an amino acid sequence of SEQ ID NO:1 or SEQ ID NO:8; and (e) synthesizing the selected polypeptide variant. In some embodiments, the polypeptide is modified, e.g., by substitution, deletion, or insertion of one, two, three, or more amino acids. In one embodiment, one or more of the amino acids is substituted with a conservative amino acid. The polypeptide can comprise one or more D amino acids. In some embodiments of this method, the modified or variant polypeptide comprises all D amino acids. In addition, to modifying one or more amino acids of the polypeptides, the backbone of the polypeptide can also be modified to make peptidomimetics as described herein.

In yet another aspect, the present invention provides use of at least one polypeptide or peptidomimetic of the present invention in the preparation of a medicament for mediating cholesterol efflux in a mammal. In exemplar embodiments, the polypeptide has an amino acid sequence selected from the group consisting of SEQ ID NOS:1-11 or, alternatively, a peptidomimetic thereof. In one embodiment, the peptidomimetic has a substantially three-dimensional conformation as a polypeptide having an amino acid sequence selected from the group consisting of SEQ ID NOS:1-11.

In a further aspect, the present invention provides use of at least one polypeptide or peptidomimetic of the present invention in the preparation of a medicament for treating a symptom of atherosclerosis in a mammal. In exemplar embodiments, the polypeptide has an amino acid sequence selected from the group consisting of SEQ ID NOS:1-11 or, alternatively, a peptidomimetic thereof. In one embodiment, the peptidomimetic has a substantially three-dimensional conformation as a polypeptide having an amino acid sequence selected from the group consisting of SEQ ID NOS:1-11.

In yet a further aspect, the present invention provides use of at least one polypeptide or peptidomimetic of the present invention in the preparation of a medicament for stabilizing a vulnerable plaque in a mammal. In exemplar embodiments, the polypeptide has an amino acid sequence selected from the group consisting of SEQ ID NOS:1-11 or, alternatively, a peptidomimetic thereof. In one embodiment, the peptidomimetic has a substantially three-dimensional conformation as a polypeptide having an amino acid sequence selected from the group consisting of SEQ ID NOS:1-11.

Another aspect of the invention provides an isolated nucleic acid encoding a polypeptide of the present invention, an expression vector comprising the nucleic acid, and a host cell comprising the expression vector.

A polypeptide and peptidomimetic of the invention is also useful as a research tool and/or diagnostic tool. For example, such a peptide can be used to identify subjects having reverse cholesterol deficient plasma and those subjects that are responders to reverse cholesterol treatment. Also, a polypeptide of the invention can be used to evaluate the anti-atherosclerotic potential of other compounds (including, e.g., peptidomimetics).

In addition, a polypeptide or peptidomimetic of the invention can be used for investigating lipoprotein-receptor interactions in animals and animal models, particularly when a polypeptide or peptidomimetic of the present invention is labeled (e.g., radioactive label, fluorescent label, etc.).

A polypeptide or peptidomimetic of the invention can also be used to identify appropriate animal models for elucidation of lipid metabolic pathways. For example, a polypeptide or peptidomimetic can be used to identify animal models and gene and/or drug interactions that have an effect on reverse cholesterol transport.

Other features, objects and advantages of the invention and its preferred embodiments will become apparent from a reading of the detailed description, examples, claims and figures that follow.

BRIEF DESCRIPTION OF THE DRAWINGS

FIG. 3 illustrates that the Km values for the polypeptides of the present invention were considerably lower (4-5 fold) than intact apolipoproteins when expressed as µg/ml, which is indicative of a high-affinity process resulting in high-levels of cholesterol efflux at relatively low concentrations of the polypeptides. On a per molecule basis, the polypeptides of the present invention stimulated cholesterol efflux from macrophages with the same apparent affinity for ABCA1 and with the approximate efficiency of full-length apoA-I and E.

FIG. 19A shows percent of lipid in plaque in whole aorta (control to free p<0.0040, control to complex p<0.0002, free to complex p=ns). FIG. 19B shows percent plaque in aortic root (control to free p<0.0001, control to complex p<0.0001, free to complex p=ns).

BRIEF DESCRIPTION OF THE SEQUENCES

Figure 1:
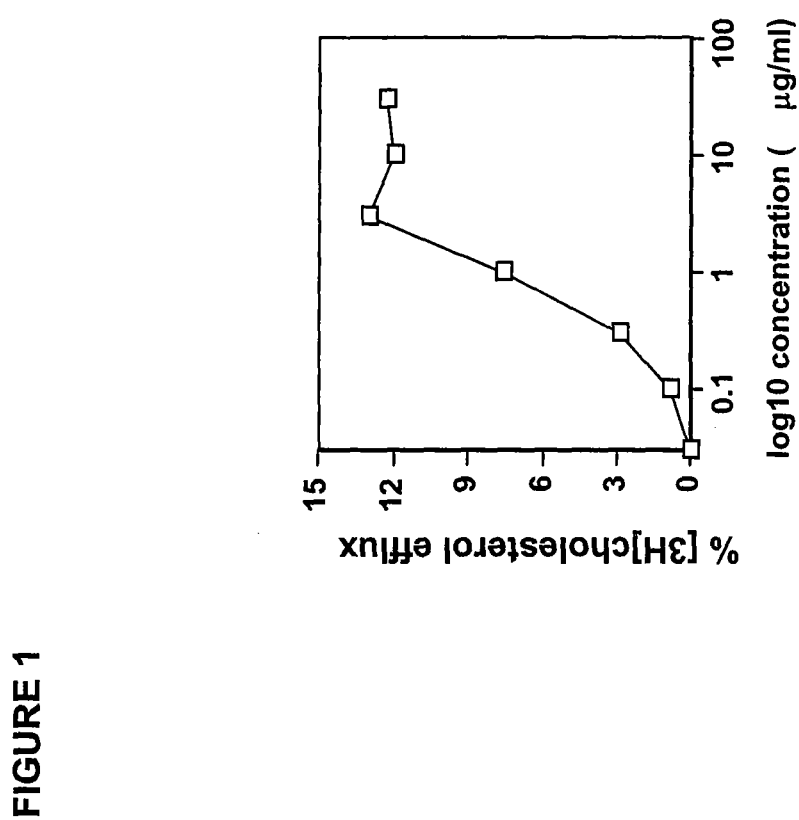
FIG. 1 illustrates that the polypeptide of SEQ ID NO:4 stimulated cholesterol efflux in a concentration-dependent manner, promoting maximal-levels of efflux at 3 µg/ml. The saturation in efflux over a narrow concentration-range and the sigmoidal curve indicate that the polypeptide of SEQ ID NO 4 stimulated cholesterol efflux via a high-affinity, cooperative process involving ABCA1.

SEQ ID NO:1 is:

| Postn[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| AA(s) | E D | F V L W | R K | S | K R | L F W | E | E D | W F | F L | A L | A | F | R L W | E K | F D | F L A W L W | E D | E D | F L W | L | A | R K | L F W |

SEQ ID NO:2 is:

| Postn[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| AA(s) | ED | F V | R | S | K | L | E | E D | W | F | A | A | F | R K | E D | F | F A | E D | E D | F | L | A | R K | L |

SEQ ID NO:3 is:

| Postn[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| AA(s) | E | F V | R | S | K | L | E | E | W | F | A | A | F | R | E | F | F A | E | E | F | L | A | R | L |

SEQ ID NOS:4-7 are as follows:

| SEQ ID NO: | Sequence |
|---|---|
| SEQ ID NO: 4 | EVRSKLEEWFAAFREFAEEFLARLKS |
| SEQ ID NO: 5 | EVRSKLEEWFAAFREFFEEFLARLKS |
| SEQ ID NO: 6 | EFRSKLEEWFAAFREFFEEFLARLKS |
| SEQ ID NO: 7 | EFRSKLEEWFAAFREFAEEFLARLKS |

SEQ ID NO:8 is:

| Postn | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| AA(s) | E | F | R | S | K | L | E | E | W | F | A | A | F | R | E | F | F | E | E | F | L | A | R | L | K | S |
|  | D | V | K |  | R | F | D | D | L | L |  |  | L | K | D | L | A | D | D | L |  |  | K | F |  |  |
|  |  | L |  |  |  | W |  |  | F | W |  |  | W |  |  | W | L |  |  | W |  |  |  | W |  |  |
|  |  | W |  |  |  |  |  |  |  |  |  |  |  |  |  |  | W |  |  |  |  |  |  |  |  |  |

SEQ ID NO:9 is:

| Postn | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| AA(s) | ED | F | R | S | K | L | E | E | W | F | A | A | F | R | E | F | F | E | E | F | L | A | R | L | K | S |
|  |  | V | K |  | R |  | D | D |  |  |  |  |  | K | D |  | A | D | D |  |  |  | K |  |  |  |

SEQ ID NO:10 is:

| Postn | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| AA(s) | E | F | R | S | K | L | E | E | W | F | A | A | F | R | E | F | F | E | E | F | L | A | R | L | K | S |
|  |  | V |  |  |  |  |  |  |  |  |  |  |  |  |  |  | A |  |  |  |  |  |  |  |  |  |

SEQ ID NO:11 is:

| Postn[1] | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| AA(s) | E | A | R | S | R | A | E | E | A | A | S | A | A | R | E | A | A | E | E | A | A | S | R | A |
|  | D | V | K | T | K | V | D | D | V | V | T | V | V | K | D | V | V | D | D | V | V | T | K | V |
|  |  | L | A | G | A | L |  |  | L | L | G | L | L | A |  | L | L |  |  | L | L | G | A | L |
|  |  | I | V | A | V | I |  |  | I | I | A | I | I | V |  | I | I |  |  | I | I | A | V | I |
|  |  | F | L | Y | L | F |  |  | F | F | Y | F | F | L |  | F | F |  |  | F | F | Y | L | F |
|  |  | W | I |  | I | W |  |  | W | W |  | W | W | I |  | W | W |  |  | W | W |  | I | W |
|  |  | M | F |  | F | M |  |  | M | M |  | M | M | F |  | M | M |  |  | M | M |  | F | M |
|  |  | P | W |  | W | P |  |  | P | P |  | P | P | W |  | P | P |  |  | P | P |  | W | P |
|  |  |  | M |  | M |  |  |  |  |  |  |  |  | M |  |  |  |  |  |  |  |  | M |  |
|  |  |  | P |  | P |  |  |  |  |  |  |  |  | P |  |  |  |  |  |  |  |  | P |  |
|  |  |  | G |  | G |  |  |  |  |  |  |  |  | G |  |  |  |  |  |  |  |  | G |  |
|  |  |  | S |  | S |  |  |  |  |  |  |  |  | S |  |  |  |  |  |  |  |  | S |  |
|  |  |  | T |  | T |  |  |  |  |  |  |  |  | T |  |  |  |  |  |  |  |  | T |  |
|  |  |  | C |  | C |  |  |  |  |  |  |  |  | C |  |  |  |  |  |  |  |  | C |  |
|  |  |  | Y |  | Y |  |  |  |  |  |  |  |  | Y |  |  |  |  |  |  |  |  | Y |  |
|  |  |  | N |  | N |  |  |  |  |  |  |  |  | N |  |  |  |  |  |  |  |  | N |  |
|  |  |  | Q |  | Q |  |  |  |  |  |  |  |  | Q |  |  |  |  |  |  |  |  | Q |  |

DETAILED DESCRIPTION OF THE INVENTION AND PREFERRED EMBODIMENTS

I. Introduction

The present invention provides, inter alia, polypeptides that possess strong cholesterol efflux activity and ABCA stabilization activity. The polypeptides of the present invention have cholesterol efflux activity and ABCA1 stabilization activity that parallels that of the native apolipoproteins, such as Apo A-I and Apo E, which is extremely surprising in view of the fact that such polypeptides are non-naturally occurring. In some cases, the polypeptides of the present invention also possess an antioxidant activity and/or an anti-inflammatory activity.

Thus, the polypeptides of the present invention are unique in that they are small in size and possess an amino acid sequence not found in nature, while possessing activities similar in nature to the native apolipoproteins. Therefore, the polypeptides of the present invention are important biological tools for in vitro and in vivo studies of ABCA1 as well as important therapeutic agents for numerous therapeutic applications.

Preferred embodiments of such polypeptides are based on the sequence of SEQ ID NOS:1-3, 8-10 and 11 as well as conservative variants thereof. Preferred polypeptides of the invention are the polypeptides having the amino acid sequences of SEQ ID NOS:4-7, which are designated ATI-5261, S1, S2, and S3, respectively. The invention provides compositions comprising such polypeptides, methods of identifying, screening and synthesizing such polypeptides, and methods of treating, preventing, or diagnosing diseases and disorders associated with dyslipidemia, hypercholesterolemia and inflammation, such as, e.g., heart disease, atherosclerotic lesions, stroke, Alzheimer's (i.e., by ameliorating plaque deposition), and storage disorders by administering such polypeptides. The invention further provides kits for treating, preventing, or diagnosing diseases and disorders associated with dyslipidemia, hypercholesterolemia and inflammation as well as lipid storage disorders.

II. Definitions

The term "ABC" or "ATP Binding Cassette" refers to multidomain membrane proteins, responsible for the controlled efflux and influx of allocrites (e.g. cholesterol) across cellular membranes. ABC proteins comprise four domains, with two transmembrane domains (TMDs) responsible for allocrite binding and transport and two nucleotide-binding domains (NBDs) responsible for coupling the energy of ATP hydrolysis to conformational changes in the TMDs. The family members include, e.g., ABCA1 and ABCA7 (see, e.g., Dean et al., *J. Lipid Res.*, 42:1007-1017 (2001)). ABCA1 is characterized in Denis et al., *J Biol. Chem.*, 279(40):41529-36 (2004). ABCA1 plays a role in cholesterol efflux and is upregulated in cells that are exposed to cholesterol enriching conditions and is the defective molecule in Tangiers Disease (Brooks-Wilson et al., *Nat. Gen.*, 22:336-344 (1999); Bodzioch et al., *Nat. Gen.*, 22:347-351 (1999); Rust et al., *Nat. Gen.*, 22:352-355 (1999)). ABCA1 turns over rapidly and has a half life of about 1 hour in the absence of a suitable stabilizer, such as an apolipoprotein (see, e.g., Wang et al., *J. Clin. Invest.*, 111:99-107 (2003)) ABCA1 sequences are set forth in Genbank Accession Nos.: AJ012376; NM_173076; NM_015657; NM_005502; NP_005493; O95477. The promoter structure and genomic organization of the human ABCA7 gene is described in Broccardo et al., *Cytogenet Cell Genet.*, 92(3-4):264-70 (2001). ABCA7 sequences are set forth in Genbank Accession Nos.: NM_033308; NM_019112; NP_150651; NP_061985; AAK00959. A family of related ATP-binding proteins has been characterized (see, e.g., Higgins et al., *J Bioenerg Biomembr.*, 22(4):571-92 (1990); Higgins et al., *Bioessay*, 8(4):111-6 (1988); Higgins et al., *Nature*, 323(6087):448-50 (1986); Doolittle et al., *Nature*, 323(6087):451-3 (1986); and Blight and Holland, *Mol. Microbiol.*, 4(6):873-80 (1990)). The proteins belonging to this family also contain one or two copies of the 'A' consensus sequence (see, e.g., Walker et al., *EMBO*, 1(8):945-51 (1982)) or the 'P-loop' (see, e.g., Saraste et al., *Trends Biochem Sci.*, 15(11):430-4 6155 (1990)). ABCA family members are reviewed in Broccardo et al., *Biochimica et Biophysica Acta*, 1461:395-404 (1999).

The term "amphipathic alpha helix" or "amphipathic α helix" refers to a polypeptide sequence that can adopt a secondary structure that is helical with one surface, i.e., face, being polar and comprised primarily of hydrophilic amino acids (e.g., Asp, Glu, Lys, Arg, His, Gly, Ser, Thr, Cys, Tyr, Asn and Gln), and the other surface being a nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Biophys. Chem.*, 16:561 (1987), and *Science*, 223:249 (1984)).

The polar face of an amphipathic α helix can, in some instances, display an "alignment of negatively charged amino acids" or "an alignment of acidic amino acids," i.e., a series of negatively charged or acidic amino acids (e.g., Asp and/or Glu) positioned approximately evenly (e.g., at about every one, two or three helical turns) within the polypeptide secondary structure. Amphipathic α helices play a role in both intra- and inter-molecular protein-protein interactions, and proteins and lipoproteins (e.g., including apolipoproteins) comprising amphipathic α helices have been postulated to play a role in lipid (e.g., HDL) transport and metabolism (see, e.g., Anantharamaiah et al., *Adv. Exp. Med. Biol.*, 285:131-40 (1991)). The structure and function of amphipathic α helices has been reviewed in, e.g., Segrest et al., *Proteins*, 8(2):103-17 (1990). In silico methods of identifying amphipathic α helices have been described by, e.g., Jones et al., *J. Lipid Res.*, 33(2):141-66 (1992). Multiple proteins comprising amphipathic α helices have been identified including, e.g., apolipoproteins and serum amyloid proteins.

A structure that is "substantially similar to a three-dimensional conformation" of a polypeptide of the invention refers to structure that comprises a core sequence, e.g., of 24 residues in length, that adopts an amphipathic α helix secondary structure that has an amphipathic orientation of amino acids along the axis of the α-helix structure, with one surface, i.e., face, being polar and comprised primarily of hydrophilic residues and the other surface being a nonpolar face that comprises primarily hydrophobic residues. Two separate acidic residue foci are present along the hydrophilic axis. A polypeptide or peptidomimetic that has a structure substantially similar to a three-dimensional conformation of a polypeptide of the invention also has the ability to stimulate ABCA1-mediated cholesterol efflux.

The term "apolipoprotein" or "Apo" or "exchangeable apolipoprotein" refers to any one of several water soluble proteins that combine with a lipid (i.e., solubilize the lipid) to form a lipoprotein and are constituents of chylomicrons, HDL, LDL and VLDL. Apolipoproteins exert their physiological effect on lipid metabolism by binding to and activating specific enzymes or lipid-transfer proteins or cell-surface receptors or ATP binding cassette transporters (e.g., ABC transporters). The interaction between apolipoproteins and ABCA1 produces cholesterol efflux and HDL particle assembly. Apolipoproteins include, e.g., Apo A-I, Apo A-II, Apo A-IV, Apo C-I, Apo C-II, Apo C-III, Apo E, and serum amyloid proteins such as, serum amyloid A.

The term "Apolipoprotein AI" or Apo A-I refers to a polypeptide comprising 243 amino acids forming N- and C-terminal domains (see, e.g., Saito et al., *J. Biol. Chem.*, 278:23227-23232 (2003) and Saito et al., *Prog. Lipid Res.*, 43:350-380 (2004)). The tertiary structure of apoA-I comprises an N-terminal four-helix bundle domain and a C-terminal domain that binds lipid strongly (see, e.g., Saito et al., *Prog. Lipid Res.*, 43:350-380 (2004) and Mishra et al., *Biochemistry*, 37:10313-10324 (1998)). Residues 44-243 of apoA-I contain the necessary structural determinants for mediating cholesterol efflux via ABCA1 (see, e.g., Chroni et al., *J. Biol. Chem.*, 278:6719-6730 (2003) and Natarajan et al., *J. Biol. Chem.*, 279:24044-24052 (2004)). This region of apoA-I (aa44-243) is comprised of a series of ten amphipathic α-helices of 11- and 22-amino acids separated by proline residues, as defined by exon 4 of the apoA-I gene (see, e.g., Borhani et al., *Proc. Natl. Acad. Sci.*, 94:12291-6 (1997)). The individual α-helical segments of apoA-I are defined, in part, by the relative distribution of positively charged residues and are designated as Class A or Y (see, e.g., Saito et al., *J. Biol. Chem.*, 278:23227-23232 (2003)). Class A helices possess positively charged amino acids at the lipid-water interface, while class Y helices exhibit a positively charged amino acid toward the middle of the polar surface in addition to interfacial cationic residues. The intact apoA-I molecule has been crystallized, along with a truncated form of the protein (A-I Δ1-43) (see, e.g., Ajees et al. *PNAS*, 103:2126-2131 (2006); Borhani et al., *Acta Crystallogr. D. Biol. Crystallogr.*, 55:1578-1583 (1999) and Segrest et al., *J. Biol. Chem.*, 274: 31755-31758 (1999)). Apo AI sequences are set forth in, e.g., Genbank Accession Nos.: P02647, J0009; AAB64381; AAB22835; 1613168A; 1403292A; CAA25519; CAA26097; and LPHUA1.

Each of the amphipathic α-helices represented by aa 44-243 of apoA-I is theoretically capable of binding to phospholipid surfaces. Helices 1 (aa 44-65) and 10 (aa 220-241) of apoA-I possess the highest lipid-binding affinity in isolated form as synthetic 22-mer polypeptides (see, e.g., Gillotte et al., *J. Biol. Chem.*, 274:2021-2028 (1999)). As such, helices 1 and 10 have been implicated as mediators of cellular cholesterol efflux and nascent HDL assembly (Palgunachari et. al., *Arteriocler. Thromb. Vasc. Biol.*, 16:328-338 (1996); Panagotopulos et. al., *J. Biol. Chem.*, 277:39477-39484 (2002); Chroni et al., *J. Biol. Chem.*, 278:6719-6730 (2003)). However, individual helices of apoA-I with high lipid-binding activity, such as helices 1 and 10, are not able to stimulate ABCA1-dependent cholesterol efflux (see e.g. Natarajan et al., *J. Biol. Chem.*, 279:24044-24052 (2004)). This suggests that factors in addition to hydrophobic effects and membrane lipid interactions are required for biological activity. In nature, relatively long stretches of several apoA-I amphipathic α-helices arranged in series and joined end-to-end via proline residues are required for mediating productive ABCA1 interactions, i.e., cholesterol efflux and HDL assembly (see, Beckstead et al., *Biochem.* 44:4591-4599 (2005); Natarajan et al., *J. Biol. Chem.*, 279:24044-24052 (2004); Chroni et al. *J. Biol. Chem.*, 278:6719-6730 (2003) and Chroni et al., *Biochem.* 43:2126-2139 (2004)). The joining of apoA-I helices 9 with 10 creates a minimum element with activity in stimulating ABCA1 lipid efflux, although the activity of this minimum helix set is somewhat weaker than full-length apoA-I protein (see, Natarajan et al., *J. Biol. Chem.*, 279:24044-24052 (2004) and Vedhachalam et al. *J. Biol. Chem.*, 279:49931-49939 (2004)).

The term "Apolipoprotein E" or "Apo E" refers to a blood plasma protein that plays an important role in lipid homeostasis in the artery wall as well as in the brain (see, e.g., Wahrle et al., *J. Biol. Chem.*, 279:40987-40993 (2004)). Apo E is synthesized and secreted by macrophage foam-cells within atherosclerotic lesions where it functions to maintain cellular cholesterol homeostasis (see, e.g. Basu et al., *Proc. Natl. Acad. Sci USA*, 78:7545-7549 (1981); Basu et al., *Science*, 219:871-873 (1983); Rosenfeld et al., *Arterioscler. Thromb.*, 13:1382-1389 (1993); O'Brien et al., *Am. J. Pathol.*, 144:538-548 (1994)) by reversing the macrophage foam-cell phenotype. These effects are related to the ability of apoE to stimulate cellular cholesterol efflux via ABCA1 as well as to its role in reverse cholesterol transport (Hara et al., *J. Biol. Chem.*, 266:3080-3086 (1991); Smith et al., *J. Biol. Chem.*, 271: 30647-30655 (1996); Oram et al., *J. Lipid Res.*, 37:2473-2491 (1996); Zhang et al., *J. Biol. Chem.*, 271:28641-28646 (1996); Remaley et al., *Biochem. Biophys. Res. Comm.*, 280: 818-823 (2001), and Mahley, *Science*, 240:622-630 (1988)). ApoE can compete with apoA-I for binding to ABCA1 expressing cells and it can form a molecular complex with ABCA1 (Krimbou et al., *J. Lipid Res.*, 45:839-848 (2004)). Defective Apo E/ABCA1 interactions in the brain dramatically reduce extracellular Apo E levels and interfere with intercellular lipid transport contributing to the development of neurological disorders (see, e.g., Hirsch-Reinshagen et al., *J. Biol. Chem.*, 279:41197-41207 (2004); Wahrle et al., *J. Biol. Chem.*, 279:40987-40993 (2004) and Koldamavo et al., *J. Biol. Chem.*, 280:43224-43235 (2005)).

The apoE protein is composed of an N-terminal four-helix bundle domain and C-terminal helices, which is similar to apoA-I (Saito et al., *Prog. Lipid Res.*, 43:350-380 (2004); Saito et al., *J. Biol. Chem.*, 278:23227-23232 (2003); Ajees et al., *Proc. Natl. Acad. Sci. USA*, 103:2128-2131 (2006)). The C-terminal domain of apoE is composed of two long helical segments separated by a proline residue (see, e.g., Hatters et al., *Trends Biochem. Sci.*, 416, in press, www.sciencedirect.com (2006); Weisgraber, *Adv. Prot. Chem.*, 45:249-302 (1994); Saito et al., *J. Biol. Chem.*, 278:23227-23232 (2003)). The first segment consists of 51 amino acids (residues 216-266) forming a class A α-helix and the second 33 amino acids (aa 267-299) that is a class G α-helix (Segrest et al., *J. Lipid Res.*, 33:141-165). Both helical segments comprising approximately 79 amino acids (residues 222-299) of the apoE CT domain are required for mediating ABCA1 lipid efflux and HDL assembly efficiently (Vedhachalam et. al., *J. Biol. Chem.*, 279(48):49931-49939 (2004)). Therefore, as is the case with Apo A-I, nature relies on relatively long stretches of multiple helical segments linked in series to elicit ABCA1-interactions and ABCA1-cellular cholesterol efflux (Vedhachalam et. al., supra). Apo E sequences are set forth in Genbank Accession Nos.: NM_000041; P02649; AAH03557; AAB59397; and AAB59518.

The terms "cholesterol efflux" and "cholesterol efflux activity" refer to efflux of cholesterol from any cell type. For example, macrophage foam-cells in the artery wall release (i.e., export) cholesterol to appropriate acceptors, such as apolipoproteins and/or HDL. A compound that mediates cholesterol efflux enhances the release, i.e., movement, of cholesterol out of the cell and into the extracellular medium or compartment. Cholesterol efflux is often accompanied by or preceded by, i.e., follows, the efflux of phospholipids from cells. The coordinated release of both cholesterol and phospholipids produces HDL in the presence of a suitable lipid acceptor, e.g., apolipoprotein or peptide. Therefore, the processes of cholesterol- and phospholipid-efflux are linked and synonymous with one another. A compound that enhances the release of cholesterol from cells increases the amount of cholesterol and/or phospholipids appearing outside the cell by at least 25%, 50%, 75%, 100% or by at least 2-fold, 4-fold, 8-fold, 10-fold or more compared to the level of cholesterol efflux in the absence of the compound.

The term "ABCA stabilization activity" or "ABCA1 stabilization" refers to enhancing and/or extending the half life of an ABCA protein by preventing its degradation. A compound that has ABCA1 stabilization activity will significantly delay the proteins degradation. This will produce an increase in cellular ABCA1 protein levels of at least 25%, 50%, 75%, 100% or at least 2-fold, 4-fold, 8-fold, 10-fold or higher compared to ABCA1 protein detected in the absence of the compound.

The term "anti-inflammatory activity" refers to prevention or reduction of inflammation. Inflammation will be recognized as playing a role in atherosclerosis development and associated with dyslipidemia, hypercholesterolemia and/or lipoprotein lipid oxidation. The inflammatory response can be local, such as in the artery wall or brain or other extra-vascular tissues, and systemic. Both local- and systemic-inflammation can be associated with generation of inflammatory mediators, such as oxidized lipids and/or cytokines. In general, the inflammatory response is associated with recruitment of blood monocyte-macrophages into extra-vascular compartments. The recruitment of monocyte-macrophages is associated with macrophage activation, differentiation and retention in the extra-vascular tissues. A compound that has anti-inflammatory activity will decrease an inflammatory response as measured by a decrease in inflammatory mediators (e.g., adhesion molecules, cytokines and/or oxidized lipids) and/or a decrease in macrophages and/or macrophage activation in plaques and tissues, compared to in the absence of the compound.

The term "antioxidant activity" refers to prevention or reduction of oxidation caused by reactive oxygen species (ROS) including, e.g., hydrogen peroxide ($H_2O_2$); hypochlorite ion (—OCl); hydroxyl radical (—OH); and the superoxide anion ($O_2$—). A number of naturally occurring substances (e.g., proteins and small molecules) possess antioxidant activity. For example, apolipoproteins can inhibit lipid peroxidation, thus protecting phospholipid surfaces from lipophilic, as well as, water soluble free radical initiators (see, e.g., *Biochemistry*, 41:2089-2096 (2002)). In addition, alpha-tocopherol (vitamin E) is an antioxidant. Moreover, proteins and peptides that promote the movement of oxidants, such as oxysterols and oxidized phospholipids, and antioxidants (vitamin E) in and out of cells via ABC transporters or any other means can be viewed as having anti-oxidant activity, to rid the artery wall of inflammatory mediators and/or affect restoration of a favorable redox balance in tissues. A compound with an antioxidant activity, has an antioxidant activity that is at least 25%, 50%, 75%, 100% or at least 2-fold, 4-fold, 8-fold, 10-fold or more higher than the antioxidant activity in the absence of the compound.

"Plaque stabilization," as used herein, refers to the stabilization of vulnerable plaques from risk of rupture or erosion by removing cholesterol from lipid rich plaques, including but not limited to, removal of cholesterol from foam cell macrophages. Plaques contain thrombogenic substances, i.e., substances that when exposed to plasma are very powerful in aggregating platelets with the risk of local thrombosis and vessel occlusion, such as tissue factor. The rupture of the plaque and exposure of such material is prevented by the fibrous cap separating the plaque from the vessel. Lipid removal confers plaque stability in two main ways. Firstly, anatomically, lipid removal by shrinking the gruel in the artery is conferring plaque stability by decreasing the risk of hemodynamical stress (expansion-contraction associated with heart beats and blood pressure changes). Secondly, as described in the literature, cholesterol accumulation is stimulating the synthesis and secretion of proteases, including matrix-metallo-proteinases (MMPs) having lysis effects on the fibrous cap.

"Reverse Cholesterol Transport (RCT)," as used herein, refers to the process of removing cholesterol from macrophage foam cells and the lipid rich plaque from the arterial wall, with subsequent transfer through plasma to the liver for uptake, processing and excretion as neutral sterols (cholesterol) or acidic sterols (hydroxylated cholesterol/bile) in feces. The efflux of cholesterol from macrophage foam cells is a requirement for RCT benefit in itself even though the cholesterol may be shifted to other less vulnerable adjacent cells. However, the further disposal of such cholesterol by transport in HDL-like particles to the liver for excretion is a favorable aspect of treatment. Such complete RCT provide a general rejuvenation of the arterial tree by actual net removal of the cholesterol content in the arteries. The RCT and plaque stabilizing effects are either conferred directly by the peptides, or the complexes that they naturally form with phospholipids in plasma and cells or, alternatively, apoA-I/HDL as the peptides bind to endogenous HDL particles, thereby changing their properties and making them more efficient to promote RCT.

A disease or disorder associated with "dyslipidemia" is any disease or disorder in which lipid metabolism is disregulated, due to alterations in tissue (i.e., blood) lipids and lipoprotein concentrations and/or aberrant mediation of cholesterol efflux or aberrant ABCA stabilization. Such diseases include, for example, heart disease, atherosclerotic lesions, stroke, Alzheimer's, and storage disorders.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. A more detailed description of amino acid as well as conservative amino acid substitutions is provided below in the section entitled "Polypeptides."

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 24 amino acids of SEQ ID NO:1), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the polypeptide, and used to detect antibodies specifically reactive with the polypeptide).

As used herein, "ameliorates" means alleviate, lessen, or decrease the extent of a symptom or decrease the number of occurrences of episodes of a disease manifestation.

The term "preventing" is art-recognized, and when used in relation to a condition, such as recurrence or onset of a disease such as hypercholesterolemia or atherosclerosis, is well understood in the art, and includes administration of a composition which reduces the frequency of, or delays the onset of, symptoms of a medical condition in a subject relative to a subject which does not receive the composition.

As used herein, "treating" means either slowing, stopping or reversing the progression of the disorder or disease. In a preferred embodiment, "treating" means reversing the progression to the point of eliminating the disorder or disease.

As used herein, "inhibits" means that the amount is reduced as compared with the amount that would occur in a control sample. In a preferred embodiment, inhibits means that the amount is reduced by more than 50%, even more preferably by more than 75% or even 100%.

A "subject," "patient" or "mammal" to be treated by the methods disclosed herein can mean either a human or non-human animal.

III. Polypeptides

The present invention provides a family of non-naturally occurring polypeptides that use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-oxidant activity as well as anti-inflammatory activity, any combination of these activities and, preferably, all of these activities.

The peptides of the invention are based on the surprising discovery of a core amino acid sequence that has an effect on cholesterol efflux. The polypeptides of the present invention are non-naturally occurring polypeptide variants of that core peptide (i.e., the polypeptide of SEQ ID NO:4, which is also referred to herein as "ATI-5261" or "5261") that stimulated ABCA1-dependent cholesterol efflux with a molar potency similar to that of apolipoproteins (e.g., Apo A-I, Apo E, etc.). Interestingly, the polypeptide family members of the present invention are small in size, corresponding to a single helical segment that captures the full biological activity and potency of intact apolipoproteins and the long stretches of multiple α-helical segments found in nature that are required to exert cholesterol efflux activity via ABCA1.

Regarding amphipathic α-helix peptides, hydrophobic amino acids are concentrated on one side of the helix, usually with polar or hydrophilic amino acids on the other. This arrangement is common in alpha helices of apolipoproteins and globular proteins, where one face of the helix is oriented toward the hydrophobic core and one face is oriented toward the water-exposed surface. Different amino-acid sequences have different propensities for forming α-helical structure. Methionine, alanine, leucine, glutamate, and lysine all have especially high helix-forming propensities, whereas proline, glycine, tyrosine, and serine have relatively poor helix-forming propensities. Proline tends to break or kink helices because it cannot donate an amide hydrogen bond (having no amide hydrogen), and because its side chain interferes sterically. Its ring structure also restricts its backbone dihedral angle to the vicinity of −70°, which is less common in α-helices. One of skill understands that although proline may be present at certain positions in the sequences described herein, e.g., at certain positions in the sequence of SEQ ID NO:11, the presence of more than three prolines within the sequence would be expected to disrupt the helical structure. Accordingly, the polypeptides of the invention do not have more than three prolines, and commonly do not have more than two prolines, present at positions in the alpha-helix forming sequence. Typically, when a proline is present in the sequence of a core helical structure of a peptide of the invention, e.g., a peptide comprising SEQ ID NO:11, it is present in only one position of the core helix sequence.

Figure 24:
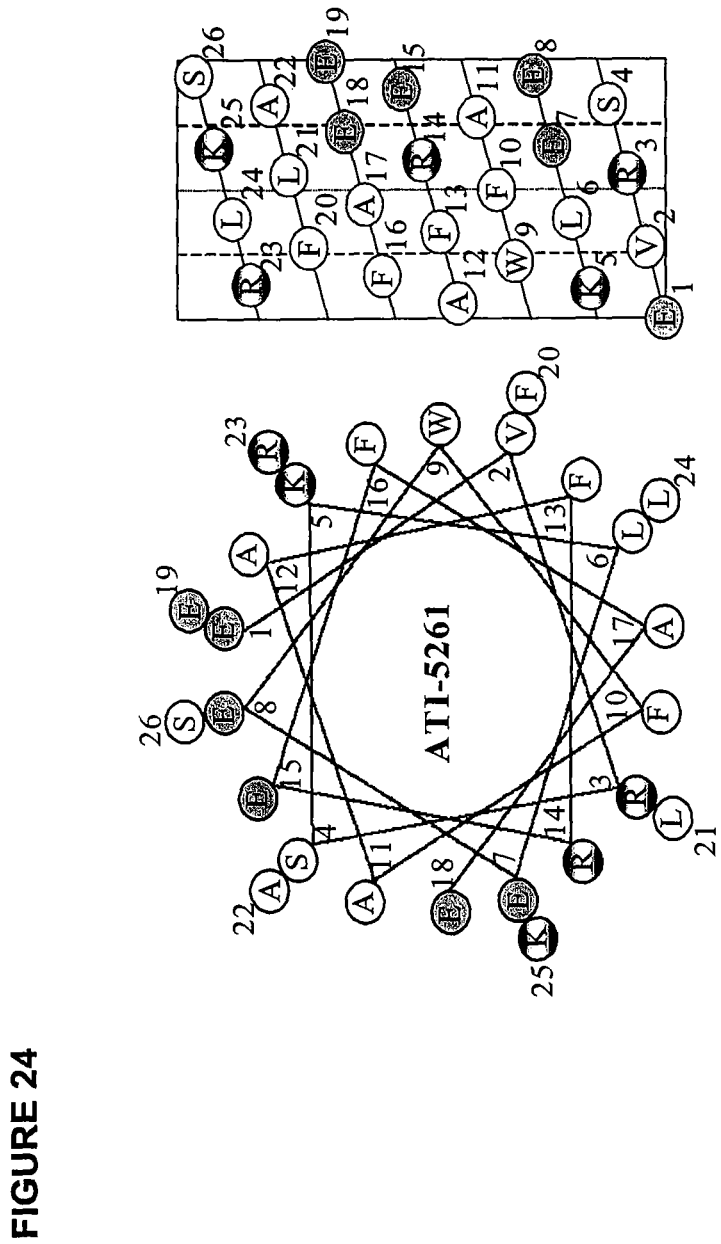
FIG. 24 illustrates the Edmundson helical wheel (SEQ ID NO:16) and cylindrical diagrams (SEQ ID NO:4) showing the structure of a consensus polypeptide of the present invention, i.e., ATI-5261. The Edmundson wheel representation shows the amphipathic nature of the helical polypeptide. The numbers refer to the primary amino acid sequence of the polypeptide. Shaded circles depict the acidic residues and partially shaded circles the positive amino acids. Each point marked by the numbers corresponds to 20° increments around the helical wheel; therefore, the non-polar surface is composed of seven residues covering 140° around the face of the helical structure; this reflects the wedge-angle created by the relative positions of R3, K5 and R23. Cutting the helical wheel projection down the long-axis of the polar surface creates the cylindrical diagram which is shown flattened.

FIG. 24 sets forth a Edmundson helical wheel and a corresponding cylindrical diagram showing the structure of the consensus sequence, i.e., the polypeptide of SEQ ID NO:4, upon which the family of polypeptides is generally based. The Edmundson wheel representation shows the amphipathic nature of the α-helical polypeptides of the present invention. The numbers refer to the primary amino acid sequence of the consensus polypeptide. Shaded circles depict the acidic amino acid residues and partially shaded circles depict the cationic amino (positively charged) acid residues. Each point marked by the numbers corresponds to 20° increments around the helical wheel. This consensus polypeptide displays the position of cationic residues at the lipid-water interface of the amphipathic α-helix set at 140°; this dictates the wedge-angle, i.e., size, of the non-polar surface, which is thought to be important for conferring activity in binding to phospholipid surfaces. One feature of this consensus polypeptide relates to putative sites of salt-bridge formation that were engineered between positively charged amino acids and negatively charged amino acids at the lipid-water interface of the amphipathic α-helix. In this consensus polypeptide, there are four such sites created by acidic/cationic pairs between residues E1/K5, E19/R23, E18/R14 and E7/R3, i.e., each cationic amino acid residue being positioned four residues from an acidic amino acid residue around the face of the amphipathic α-helix. It is thought that the creation of numerous sites for potential intra-helical salt-bridges may help stabilize the secondary structure of the polypeptide, optimizing its α-helical content. Cutting the helical wheel projection down the long-axis of the polar surface creates the cylindrical diagram, which is shown flattened in FIG. 24. Again, it is upon this consensus sequence that the family of polypeptides of the present invention is generally based.

Thus, in one embodiment, the present invention provides an isolated polypeptide comprising an amino acid sequence of SEQ ID NO:10. More particularly, the present invention provides an isolated polypeptide comprising the following amino acid sequence:

(SEQ ID NO: 10)
EX$_2$RSKLEEWFAAFREFX$_{17}$EEFLARLKS wherein X$_2$ is an amino acid including, but not limited to, F and V; and X$_{17}$ is an amino acid including, but not limited to, F and A; and wherein each letter stands for the conventional one-letter amino acid code.

In one embodiment, the isolated polypeptide comprises (and, in certain embodiments, consists of or, alternatively, consists essentially of) the following amino acid sequence: EVRSKLEEWFAAFREFAEEFLARLKS (SEQ ID NO:4, which again is also referred to herein as "ATI-5261" or "5261"). In another embodiment, the isolated polypeptide comprises (and, in certain embodiments, consists of or, alternatively, consists essentially of) the following amino acid sequence: EVRSKLEEWFAAFREFFEEFLARLKS (SEQ ID NO:5, which is also referred to herein as "S1"). In yet another embodiment, the isolated polypeptide comprises (and, in certain embodiments, consists of or, alternatively, consists essentially of) the following amino acid sequence: EFRSKLEEWFAAFREFFEEFLARLKS (SEQ ID NO:6, which is also referred to herein as "S2"). In yet another embodiment, the isolated polypeptide comprises (and, in certain embodiments, consists of or, alternatively, consists essentially of) the following amino acid sequence: EFRSKLEEWFAAFREFAEEFLARLKS (SEQ ID NO:7, which is also referred to herein as "S3").

It will be readily understood by those of skill in the art that the foregoing polypeptides are not fully inclusive of the family of polypeptides of the present invention. In fact, using the teachings provided herein, other suitable polypeptides (e.g., conservative variants) can be routinely produced by, for example, conservative or semi-conservative substitutions (e.g., D replaced by E), extensions, deletions and the like. In addition, using the assays provided herein, other suitable polypeptides can be routinely screened for desired biological activities.

Thus, in another embodiment, the present invention provides polypeptide variants of the polypeptides of SEQ ID NOS:10 and 4-7. In one exemplary embodiment, the polypeptides have at least 75%, at least 80%, at least 85%, at least 90%, at least 95% or at least 98% identity to the polypeptides of SEQ ID NO:10 and, more particularly, to the polypeptides of SEQ ID NOS:4-7. In another embodiment, the present invention provides polypeptide variants of the polypeptides of SEQ ID NOS:1-3 and 8-9. In one exemplary embodiment, the polypeptides have at least 75%, at least 80%, at least 85%, at least 90%, at least 95% or at least 98% identity to the polypeptides of SEQ ID NO:1 or, more particularly, the polypeptides of SEQ ID NOS:3 and 8-9. As will be appreciated by those of skill in the art, non-identical amino acid residues can be naturally or non-naturally occurring. The term "percent identical" refers to sequence identity between two amino acid sequences (or between two nucleotide sequences, which are also provided by the present invention). Identity can each be determined by comparing a position in each sequence that may be aligned for purposes of comparison. When an equivalent position in the compared sequences is occupied by the same amino acid or base, then the molecules are identical at that position; when the equivalent site is occupied by the same or a similar amino acid residue (e.g., similar in steric and/or electronic nature), then the molecules can be referred to as homologous (similar) at that position. Expression as a percentage of homology, i.e., similarity, or identity refers to a function of the number of similar or identical amino acids at positions shared by the compared sequences. Various alignment algorithms and/or programs can be used, including, for example, PASTA, BLAST and ENTREZ. PASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

In another exemplary embodiment, which can overlap with the embodiments described above, the polypeptides of SEQ ID NO:10 and, more particularly, the polypeptides of SEQ ID NOS:4-7 are substituted with conservative (or semi-conservative) amino acid residues. Similarly, in other embodiments, the polypeptides of SEQ ID NO:1 or, more particularly, the polypeptides of SEQ ID NOS:3 and 8-9 are substituted with conservative (or semi-conservative) amino acid residues. The term "conservative amino acid substitutions" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (see, e.g., Schulz, G. E. and R. H. Schirmer, Principles of Protein Structure, Springer- Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr.

In another exemplary embodiment, which again can overlap with the embodiments described above, "a conservative amino acid substitution" can refer to the substitution of an amino acid for another that is similar in molecular weight or similar in hydrophobicity. By "similar molecular weight" and "similar hyrdrophobicity" is meant a value that is within 25%, more preferably 20%, 15%, 10%, or less than 10% of the respective value. Data for amino acid molecular weights and hydrophobicities are set forth in Table 1. A hydrophobicity ranking is set forth in Table 2; a conservative substitution includes exchanging an amino acid that is designated "=" to another (e.g., Tyr=Trp) and exchanging one amino acid for another that is adjacent to it in the ranking order as delineated by the greater and lesser than symbols.

TABLE 1

Parameters for the Unmodified Physiological L-alpha-Amino Acids

| Amino Acid | 3-Letter Code | 1-Letter Code | Molecular Weight† | Hydrophobicity‡ |
|---|---|---|---|---|
| Alanine | Ala | A | 89.09 | 0.616 |
| Cysteine | Cys | C | 121.16 | 0.680 |
| Aspartate | Asp | D | 133.10 | 0.028 |
| Glutamate | Glu | E | 147.13 | 0.043 |
| Phenylalanine | Phe | F | 165.19 | 1.00 |
| Glycine | Gly | G | 75.07 | 0.501 |
| Histidine | His | H | 155.16 | 0.165 |
| Isoleucine | Ile | I | 131.18 | 0.943 |
| Lysine | Lys | K | 146.19 | 0.283 |
| Leucine | Leu | L | 131.18 | 0.943 |
| Methionine | Met | M | 149.21 | 0.738 |
| Asparagine | Asn | N | 132.12 | 0.236 |
| Proline | Pro | P | 115.13 | 0.711 |
| Glutamine | Gln | Q | 146.15 | 0.251 |
| Arginine | Arg | R | 174.20 | 0.000 |
| Serine | Ser | S | 105.09 | 0.359 |
| Threonine | The | T | 119.12 | 0.450 |
| Valine | Val | V | 117.15 | 0.825 |
| Tryptophan | Trp | W | 204.23 | 0.878 |
| Tyrosine | Tyr | Y | 181.19 | 0.880 |

†The molecular weights given are those of the neutral, free amino acids; residue weights can be obtained by subtraction of one equivalent of water (18 g/mol).
‡The hydrophobicities given are the "Scaled" values from computational log(P) determinations by the "Small Fragment Approach" (see, "*Development of Hydrophobicity Parameters to Analyze Proteins Which Bear Post- or Cotranslational Modifications*" Black, S. D. and Mould, D. R., *Anal. Biochem.*, 193: 72-82 (1991)). The equation used to scale raw log(P) values to the scaled values given is as follows: Scaled Parameters = (Raw Parameters + 2.061)/4.484.

TABLE 2

Trend of Hydrophobicity Parameters for the Physiological L-alpha-Amino Acids

Phe > Leu = Ile > Tyr = Trp > Val > Met > Pro > Cys > Ala > Gly > Thr > Ser > Lys > Gln > Asn > His > Glu > Asp > Arg

Another indication that two polypeptides are conservative variants of one another is that the two polypeptides carry out the same function and, in preferred embodiments, the same function at the same or very similar level of activity. Thus, in one embodiment, a conservative variant of a polypeptide of this invention will comprise an activity of at least 80%, 85%, 86%, 87%, 88%, 89%, 90%, 91%, 92%, 93%, 94%, 95%, 96%, 97%, 98%, 99%, or 100% of that found in a polypeptide of SEQ ID NO:10 or, more particularly, a polypeptide of SEQ ID NOS:4-7. Similarly, in other embodiments, a conservative variant of a polypeptide of this invention will comprise an activity of at least 80%, 85%, 86%, 87%, 88%, 89%, 90%, 91%, 92%, 93%, 94%, 95%, 96%, 97%, 98%, 99%, or 100% of that found in a polypeptide of SEQ ID NO:1 or, more particularly, a polypeptide of SEQ ID NOS:3 and 8-9. Again, in some embodiments, the polypeptides of this invention will possess more than one activity. For example, a polypeptide of the invention can comprise cholesterol efflux mediating activity, ABCA stabilization activity, anti-inflammatory activity as well as antioxidant activity, any combination of these activities or, ideally, all of these activities. Conservative variants can have one or more of the same activities and, ideally, all of the same activities. The screening assays described herein can be readily used by those of skill in the art to determine whether two or more polypeptides possess similar activities. In addition, those of skill in the art will know of other screening assays that can be used to determine whether two or more polypeptides possess similar biological properties or activities.

While in preferred embodiments, the polypeptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) can be used in the polypeptides of the present invention. As with the other amino acid substitutions, non-naturally occurring amino acids are typically substituted so that, upon substitution, they retain the spatial and ionic or non-ionic character of the residue that they substitute.

Thus, in one embodiment, the present invention provides polypeptides having conservative amino acid substitutions of the polypeptides of SEQ ID NO:10 and SEQ ID NOS:4-7, the polypeptides comprising the following amino acid sequence:

```
X1X2X3SX5X6X7X8X9X10AAX13X14X15X16X17X18X19X20LAX23X24KS
(SEQ ID NO: 17; including, but not limited to, the
substitutions of SEQ ID NO: 8)
``` wherein $X_1$, $X_7$, $X_8$, $X_{15}$, $X_{18}$ and $X_{19}$ are each independently selected and are amino acids including, but not limited to, E and D; $X_2$ is an amino acid including, but not limited to, F, V, L and W; $X_3$, $X_5$, $X_{14}$ and $X_{23}$ are each independently selected and are amino acids including, but not limited to, R and K; $X_6$, $X_9$, $X_{10}$, $X_{13}$, $X_{16}$, $X_{20}$ and $X_{24}$ are each independently selected and are amino acids including, but not limited to, L, F and W; and $X_{17}$ is an amino acid including, but not limited to, F, A, L and W. In certain embodiments, the conservatively modified polypeptides of SEQ ID NO:8 will have one or more of the same activities and, ideally, all of the same activities as a polypeptide of SEQ ID NO:10 or a polypeptide of SEQ ID NOS:4-7.

In another embodiment, the present invention provides polypeptides having conservative amino acid substitutions of the polypeptides of SEQ ID NO:10 and SEQ ID NOS:4-7, the polypeptides comprising the following amino acid sequence:

$X_1X_2X_3SX_5LX_7X_8WFAAFX_{14}X_{15}FX_{17}X_{18}X_{19}FLAX_{23}LKS$
(SEQ ID NO: 18; including, but not limited to, the substitutions of SEQ ID NO: 9)

wherein $X_1$, $X_7$, $X_8$, $X_{15}$, $X_{18}$ and $X_{19}$ are independently selected and are amino acids including, but not limited to, E and D; $X_2$ is an amino acid including, but not limited to, F and V; $X_3$, $X_5$, $X_{14}$ and $X_{23}$ are each independently selected and are amino acids including, but not limited to, R and K; and $X_{17}$ is an amino acid including, but not limited to, F and A. As with the conservatively modified polypeptides of SEQ ID NO:8, the conservatively modified polypeptides of SEQ ID NO:9 will have one or more of the same activities and, ideally, all of the same activities as a polypeptide of SEQ ID NO: 10 or a polypeptide of SEQ ID NOS:4-7.

In addition to the foregoing, the present invention provides truncated forms of the polypeptides of SEQ ID NOS:4-7 and 8-10. In one such embodiment, the amino acids at positions 25 (i.e., K) and 26 (i.e., S) of SEQ ID NOS:8-10 are not present. The resulting polypeptides, i.e., the polypeptides of SEQ ID NOS:1-3, 11, which are 24 amino acids in length, have properties similar to the polypeptides of SEQ ID NO:8-10. Similarly, polypeptides of the invention can be truncated relative to the polypeptides of SEQ IDS NO:4-7. Again, in such embodiments, the amino acids at positions 25 and 26 are not present (SEQ ID NO:12-15).

One of skill understands that amino acid residues may be added to either the C-terminus and/or N-terminus of the polypeptides of the present invention without effecting the activity of such polypeptides. Thus, a polypeptide of the invention that comprises a helical sequence as described herein (e.g., SEQ ID NO:1 or SEQ ID NO:11), includes embodiments that are over 24 amino acids in length, e.g., peptide that are 25, 26, 28, 30, 32, 35, or 40 amino acids in length. One of skill also understands that polypeptides of the invention may also be linked, e.g., via a proline or other linker residues, to another amphipathic α helical peptide that can stimulate cholesterol efflux to form longer polypeptides, e.g., of 50, 60, 70, 80, 90, or 100 amino acids in length. Accordingly, a sequence of any of SEQ ID NOs. 1-15 can have amino acid additions or can be joined. For example, one molecule of a polypeptide of the invention, e.g., SEQ ID NO: 4, 5, 6, or 7, may be joined to another molecule of the polypeptide through a proline residue to provide a polypeptide that is 53 amino acids in length. Similarly, two 24-mers, e.g., any of SEQ ID NOs 1, 11, or 12-15, can be joined to another 24-mer or to a 26-mer, e.g., using a proline, thereby resulting in a polypeptide that is 49-53 residues in length. Such a polypeptide can have cholesterol efflux activity that exceeds that of a native full-length apolipoproteins (e.g., Apo AI and Apo E), or that of the cholesterol efflux-mediating domain of the apolipoprotein. Using the methodologies described herein, one of skill can readily add additional amino acids to either the C-terminus and/or N-terminus, and then screen the resulting polypeptides for the desired activity.

In view of the foregoing, the present invention provides an isolated polypeptide comprising the following amino acid sequence:

(SEQ ID NO: 11)
$X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$ wherein: $X_1$, $X_7$, $X_8$, $X_{15}$, $X_{18}$ and $X_{19}$ are amino acids independently selected from the group consisting of E and D; $X_2$, $X_6$, $X_9$, $X_{10}$, $X_{12}$, $X_{13}$, $X_{16}$, $X_{17}$, $X_{20}$, $X_{21}$ and $X_{24}$ are amino acids independently selected from the group consisting of A, V, L, I, F, W, M and P; $X_3$, $X_5$, $X_{14}$ and $X_{23}$ are amino acids independently selected from the group consisting of R, K, A, V, L, I, F, W, M, P, G, S, T, C, Y, N and Q, wherein at least two of $X_3$, $X_5$, $X_{14}$ and $X_{23}$ are amino acids independently selected from the group consisting of R and K; and $X_4$, $X_{11}$, and $X_{22}$ are amino acids independently selected from the group consisting of S, T, G, A and Y; wherein each letter stands for the conventional one-letter amino acid code. The polypeptides of SEQ ID NO:11 have cholesterol efflux activity, ABCA1-stabilization activity, anti-oxidant activity as well as anti-inflammatory activity.

In certain embodiments of the polypeptide of SEQ ID NO:11, $X_2$, $X_6$, $X_9$, $X_{10}$, $X_{12}$, $X_{13}$, $X_{16}$, $X_{17}$, $X_{20}$, $X_{21}$ and $X_{24}$ are amino acids independently selected from the group consisting of A, V, L, F and W and, preferably, are amino acids independently selected from the group consisting of A, L, F and W. In other embodiments of the polypeptide of SEQ ID NO:11, at least three of $X_3$, $X_5$, $X_{14}$ and $X_{23}$ are amino acids independently selected from the group consisting of R and K. In certain other embodiments, $X_3$, $X_5$, $X_{14}$ and $X_{23}$ are amino acids independently selected from the group consisting of R, K, L and F, wherein at least two of $X_3$, $X_5$, $X_{14}$ and $X_{23}$ are amino acids independently selected from the group consisting of R and K. In yet other embodiments, $X_4$, $X_{11}$, and $X_{22}$ are amino acids independently selected from the group consisting of S, A and Y and, preferably, $X_4$, $X_{11}$, and $X_{22}$ are each A.

In another aspect, the present invention provides an isolated polypeptide comprising the following amino acid sequence:

(SEQ ID NO: 1)
$X_1X_2X_3SX_5X_6X_7X_8X_9X_{10}AAX_{13}X_{14}X_{15}X_{16}X_{17}X_{18}X_{19}X_{20}LAX_{23}X_{24}$ wherein: $X_1$, $X_7$, $X_8$, $X_{15}$, $X_{18}$ and $X_{19}$ are amino acids independently selected from the group consisting of E and D; $X_2$ is an amino acid selected from the group consisting of F, V, L and W; $X_3$, $X_5$, $X_{14}$ and $X_{23}$ are amino acids independently selected from the group consisting of R and K; $X_6$, $X_9$, $X_{10}$, $X_{13}$, $X_{16}$, $X_{20}$ and $X_{24}$ are amino acids independently selected from the group consisting of L, F and W; and $X_{17}$ is an amino acid selected from the group consisting of F, A, L and W; and wherein each letter stands for the conventional one-letter amino acid code. The polypeptides of SEQ ID NO:1 have cholesterol efflux activity, ABCA1-stabilization activity, anti-oxidant activity as well as anti-inflammatory activity.

In a particularly preferred embodiment, the polypeptides of the present invention comprise one or more D-amino acids as described herein. In certain embodiments, every amino acid (e.g., every enantiomeric amino acid) is a D-amino acid. It has been found that polypeptides comprising all D-amino acids stimulate cholesterol efflux with high-capacity and high-affinity like the L-amino acid polypeptides. D-amino acids are readily incorporated at one or more positions in the polypeptide simply by using a D-form derivatized amino acid residue in the chemical synthesis. D-form residues for solid phase polypeptide synthesis are commercially available from a number of suppliers (see, e.g., Advanced Chem Tech, Louisville, Ky.; Nova Biochem, San Diego, Calif.; Sigma, St Louis, Mo.; Bachem California Inc., Torrance, Calif., etc.). The D-form amino acids can be incorporated at any position in the polypeptide as desired. Thus, for example, in one embodiment, the polypeptide can comprise a single D-amino acid, while in other embodiments, the polypeptide comprises at least two, generally at least three, more generally at least four, most generally at least five, preferably at least six, more preferably at least seven and most preferably at least eight D amino acids. In one embodiment, essentially every other (enantiomeric) amino acid is a D-form amino acid. In certain embodiments, at least 80%, preferably at least 90%, more preferably at least 95% of the enantiomeric amino acids are D-form amino acids. In one particularly preferred embodiment, essentially every enantiomeric amino acid is a D-form amino acid.

In yet another embodiment, peptidomimetics of the polypeptides of the present invention are provided. A "peptidomimetic" includes any modified form of an amino acid chain, including, but not limited to, phosphorylation, capping, fatty acid modifications and including unnatural backbone and/or side chain structures. It will be readily apparent to those of skill in the art that a peptidomimetic comprises the structural continuum between an amino acid chain and a non-peptide small molecule. Peptidomimetics generally retain a recognizable polypeptide-like polymer unit structure. Thus, a peptidomimetic typically retains the function of binding to any target molecule that a natural polypeptide binds to. Examples of suitable peptidomimetics are disclosed in U.S. Patent Application Publication No. 2006/0069030, the teachings of which are incorporated by reference for all purposes. Other peptidomimetics and methods of making same will be known to those of skill in the art.

In preferred embodiments, the peptidomimetics of the present invention fall into one of two categories: (i) surrogates; and (ii) analogs. Numerous surrogates have been developed for the amide bond of polypeptides. Frequently exploited surrogates for the amide bond include, but are not limited to, the following groups: (i) trans-olefins, (ii) fluoroalkene, (iii) methyleneamino, (iv) phosphonamides, and (v) sulfonamides. Examples of such surrogates are disclosed in U.S. Patent Application Publication No. 2006/0069030. Additionally, peptidomimetics based on more substantial modifications of the backbone of a polypeptide can be used. Peptidomimetics that fall in this category include (i) retro-inverso analogs, and (ii) N-alkyl glycine analogs (so-called peptoids). Again, examples of such analogs are disclosed in U.S. Patent Application Publication No. 2006/0069030.

In one embodiment of the present invention, the peptide or peptidomimetic is a retro-inverso analog. Retro-inverso analogs can be made according to the methods known in the art, in a manner similar to synthesizing L-amino acid based polypeptides. More specifically, examples of methods suitable for preparing such retro-inverso analogs are described in U.S. Pat. No. 4,522,752, which issued to Sisto et al. The final product, or intermediates thereof, can be purified by HPLC or any other suitable chromatographic method known to those of skill in the art.

In another embodiment, the peptide or peptidomimetic is a retro-enantio analog. Retro-enantio analogs can be synthesized from commercially available D-amino acids (or analogs thereof) using standard solid- or solution-phase polypeptide-synthesis techniques.

In still another embodiment, the peptidomimetic is a trans-olefin analog or derivative. Such trans-olefin analogs of a polypeptide can be readily synthesized according to the method of Shue et al., *Tetrahedron Lett.*, 28:3225 (1987). In addition, other methods known in the art can also be used. It will be appreciated that variations in the procedure of Sjue et al., or other procedures available, may be necessary depending on the nature of the reagents used in synthesizing the trans-olefin derivative.

It is also possible to couple the pseudodipeptides synthesized by the above method to other pseudodipeptides, to make pseudopeptides with several olefinic functionalities in place of amide functionalities. For example, pseudodipeptides corresponding to certain di-peptide sequences can be made and then coupled together by standard techniques to yield an analog of the polypeptide that has alternating olefinic bonds between residues.

Still another class of peptidomimetic derivatives includes phosphonate derivatives. The synthesis of such phosphonate derivatives can be adapted from known synthesis schemes (see, for example, Loots et al. in "Peptides: Chemistry and Biology," (Escom Science Publishers, Leiden, p. 118, 1988); Petrillo et al. in "Peptides: Structure and Function (Proceedings of the 9th American Peptide Symposium)," (Pierce Chemical Co. Rockland, Ill., 1985).

In other embodiments, the modification can be the introduction of carbohydrate or lipid moieties. Such modifications can change the solubility of the polypeptides in various mediums so that they can advantageously be prepared as a suitable pharmaceutical composition. Modifying lipid groups include, but are not limited to, farnesyl groups and myristoyl groups. Modifying carbohydrate groups include, but are not limited to, single sugars or oligosaccharides of any naturally occurring and/or synthetic sugar and sugar alcohols including, for example, glucose, galactose, rhamnose, mannose, arabinose, and other sugars, and their respective alcohols.

In certain embodiments, the peptidomimetics of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or mono-saccharide, and phosphates. Effects of such non-amino acid elements on the functionality of a peptidomimetic can be tested using the assay methods disclosed herein.

Thus, in a preferred embodiment, the peptidomimetics of the present invention have a three-dimensional conformation that is substantially similar to a polypeptide of SEQ ID NO:1, SEQ ID NOS:2-5 or SEQ ID NOS:6-7. In particular embodiments, the peptidomimetics include at least one backbone linkage that is not an amide linkage in the amino to carboxy direction, such as a retro-inverso polypeptide relative to a naturally-occurring polypeptide, or at least one backbone linkage that is not an amide linkage.

The polypeptides as well as the peptidomimetics of the present invention, including, for example, the retro-inverso peptidomimetics, can be modified so that the R-groups on the constituent amino acids and/or the terminal amino acids are blocked, i.e., protected, by a protecting group. It has been found that blockage, particularly of the amino and/or carboxy termini, greatly improves oral delivery and significantly increases serum half-life. As used herein, "protecting group" refers to a temporary substituent that protects a potentially reactive functional group from undesired chemical transformations. Examples of such protecting groups generally include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

A wide number of protecting groups are suitable for this purpose. Such groups include, but are not limited to, acetyl, $CH_3$—$(CH_2)_n$—CO—, amide, Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Born), cyclohexyloxy (cHxO), t-butoxymethyl (Bum), t-butoxy (tBuO), t-Butyl (tBu), and Trifluoroacetyl (TFA). The variable "n" is an integer from 0 to 12, typically 0 to 6 such as 0 to 4. Other suitable protecting groups are disclosed in U.S. Pat. No. 6,933,279, the teachings of which are incorporated by reference.

In one embodiment, preferred protecting groups include, but are not limited to, acetyl, amide, and alkyl groups with acetyl and alkyl groups being particularly preferred for N-terminal protection and amide groups being particularly preferred for carboxyl terminal protection. In one preferred embodiment, an acetyl group is used to protect the amino terminus and an amide group is used to protect the carboxyl terminus. In this embodiment, acetylation can be accomplished during the synthesis when the polypeptide is on the resin using acetic anhydride. Amide protection can be achieved by the selection of a proper resin for the synthesis. For instance, a rink amide resin can be used. After the completion of the synthesis, the semipermanent protecting groups on acidic bifunctional amino acids, such as Asp and Glu, and basic amino acids, such as Lys, as well as the hydroxyl of Tyr, are all simultaneously removed. The polypeptides released from such a resin using acidic treatment comes out with the N-terminal protected as acetyl and the C-terminal protected as $NH_2$, with the simultaneous removal of all of the other protecting groups.

A. Chemical Synthesis

The polypeptides can be chemically synthesized using methods well known in the art including, e.g., solid phase synthesis (see, e.g., Merrifield, J. Am. Chem. Soc., 85:2149-2154 (1963) and Abelson et al., Methods in Enzymology, Volume 289: Solid-Phase Peptide Synthesis (1st ed. 1997)). Polypeptide synthesis can be performed using manual techniques or by automation. Automated synthesis can be achieved, for example, using Applied Biosystems 431A Peptide Synthesizer (Perkin Elmer). Alternatively, various fragments of the polypeptide can be chemically synthesized separately and then combined using chemical methods to produce the full length polypeptide. The sequence and mass of the polypeptides can be verified by GC mass spectroscopy. Once synthesized, the polypeptides can be modified, for example, by N-terminal acetyl- and C-terminal amide-groups as described above. Synthesized polypeptides can be further isolated by HPLC to a purity of at least about 80%, preferably 90%, and more preferably 95%.

B. Recombinant Expression

The polypeptides described herein can also be expressed recombinantly, especially when the polypeptide does not comprise a "D" amino acid residues. This embodiment relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

Polymerase chain reaction or other in vitro amplification methods may also be useful, for example, to clone nucleic acid sequences that code for the polypeptides to be expressed, to make nucleic acids to use as probes for detecting the presence of encoding mRNA in physiological samples, for nucleic acid sequencing, or for other purposes. Nucleic acids amplified by the PCR reaction can be purified from agarose gels and cloned into an appropriate vector.

Gene expression of a sequence of the invention can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

To obtain high level expression of a nucleic acid sequence, such as the nucleic acid sequences encoding a polypeptide of this invention, one typically subclones a nucleic acid sequence that encodes a polypeptide sequence of the invention into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding a polypeptide of the invention or a subsequence thereof. Suitable bacterial promoters are well known in the art and described, e.g., in Sambrook et al. and Ausubel et al. The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant polypeptides to provide convenient methods of isolation, e.g., His tags. In some cases, enzymatic cleavage sequences (e.g., Met-His-Ile-Glu-Gly-Arg which form the Factor Xa cleavage site) are added to the recombinant polypeptides. Bacterial expression systems for expressing the polypeptides are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of polypeptides of the invention, which are then purified using standard techniques (see, e.g., Colley et al., *J. Biol. Chem.*, 264:17619-17622 (1989); Guide to Protein Purification, in Methods in Enzymology, vol. 182 (Deutscher, ed., 1990)). Transformation of cells is performed according to standard techniques (see, e.g., Morrison, *J. Bact.*, 132:349-351 (1977); Clark-Curtiss & Curtiss, *Methods in Enzymology*, 101:347-362 (Wu et al., eds, 1983). For example, any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of a polypeptide of the invention. Polypeptides of the invention are recovered from the culture using standard techniques identified below.

C. Purification of Polypeptides

Polypeptides are purified to substantial purity by standard techniques known in the art, including, for example, extraction and purification from inclusion bodies, size differential filtration, solubility fractionation (i.e., selective precipitation with such substances as ammonium sulfate); column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when polypeptides are being purified. For example, polypeptides having established molecular adhesion properties can be reversible fused to recombinant polypeptides. With the appropriate ligand, the recombinant polypeptides can be selectively adsorbed to a purification column and then freed from the column in a relatively pure form. The fused polypeptide is then removed by enzymatic activity. Finally, the polypeptides may be purified using immunoaffinity columns.

IV. Methods of Identifying Polypeptides with Desired Activity

The polypeptides or peptidomimetics of the present invention can be readily screened for their ability to mediate cholesterol efflux and/or stabilize ABCA (e.g., ABCA1) using methods well known to those of skill in the art.

A number of different screening protocols can be utilized to identify polypeptides or peptidomimetics of the present invention that mediate cholesterol efflux and/or stabilize ABCA (e.g., ABCA1). In one embodiment, the screening methods involve screening a plurality of test polypeptides to identify those polypeptides that mediates cholesterol efflux and/or stabilizes ABCA (e.g., ABCA1) in, e.g., mammalian cells, including human cells.

In addition to screening for their ability to mediate cholesterol efflux and/or stabilize ABCA, candidate test polypeptides can also be screened for other activities including, e.g., anti-oxidant activities and anti-inflammatory activities. A number of different screening protocols can be utilized to identify polypeptides or peptidomimetics of the present invention that have anti-oxidant activity and/or anti-inflammatory activity.

It will be readily apparent to those of skill in the art that numerous other screening assays, in addition to those disclosed herein, can be used to screen the polypeptides or peptidomimetics of the present invention for the desired biological activities.

A. Screening for Cholesterol Efflux Activity

Suitable cholesterol efflux assays are described in, e.g., Bielicki, J. K and Oda, M. N., *Biochemistry*, 41:2089-2096 (2002); Jia et al., *Biochem. Biophys. Res. Common.*, 297:206-213 (2002). In some embodiments, a polypeptide known to mediate cholesterol efflux (e.g., helix 9/10 of Apo A-I) is used to screen for additional mediators of cholesterol efflux in a cell based assay. For example, cell lines in which cholesterol efflux can be enhanced using a cAMP analog that up-regulates ABCA1 protein expression (e.g., J774 macrophages) can conveniently be used to assess the ability of a polypeptide of the present invention to mediate cholesterol efflux. The cells are incubated with labeled cholesterol (e.g., [$^3$H]cholesterol) under conditions appropriate for cholesterol uptake by the cells. Thus, cAMP or cAMP analogs (e.g., CPT-cAMP) are incubated with the cells for a suitable time before the initiation of cellular cholesterol efflux, i.e., prior to contacting the cells with a test polypeptide. Measurement of labeled cholesterol appearing in the medium is used to determine the cholesterol efflux mediating activity of the test polypeptide.

B. Screening for ABCA Stabilization Activity

Multiple assays known in the art can be used to measure the ABCA stabilization activity of a polypeptide of the invention. For example, binding assays can be used to test the ability of the test polypeptide to bind to ABCA (e.g., ABCA1). It has been found that polypeptides having ABCA stabilization activity are also likely mediators of cholesterol efflux. As such, in a preferred embodiment, the polypeptides or peptidomimetics of the present invention have the ability to mediate cholesterol efflux and to stabilize ABCA. In one screening embodiment, the binding assays can be competitive assays. Other assays include, for example, direct measurement of ABCA (e.g., ABCA protein or nucleic acids) following contact with the test polypeptide.

1. Binding Assays

Binding assays usually involve contacting ABCA with one or more test polypeptides, and allowing sufficient time for ABCA and the test polypeptides to form a binding complex. Any binding complexes formed can be detected using any of a number of established analytical techniques. Protein binding assays include, but are not limited to, immunohistochemical binding assays, flow cytometry or other assays. In some embodiments, competition assays are used to determine whether a test polypeptide has ABCA stabilization activity. Competition assays are well known in the art. Typically, a competitor compound, i.e., a compound known to bind ABCA, is labeled so that differences in binding to ABCA (e.g., in the presence of increasing amount of a test polypeptide of the invention that may bind to ABCA) can be measured. The particular label or detectable group used in the assay is not a critical aspect of the invention, as long as it does not significantly interfere with the binding of the test compound to ABCA. As described herein, the detectable group (or, alternatively, detectable moiety or label) can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include, but are not limited to, magnetic beads (e.g., DYNA-BEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

In some embodiments, ABCA expressing and non-expressing cells are used to measure the ABCA (e.g., ABCA1) stabilization activity of a test polypeptide by measuring the relative ABCA binding affinities of the test polypeptide and a competitor compound (e.g., full-length Apo A-I A or Apo A-I 9/10 polypeptide) for ABCA. In some embodiments, the binding affinity of full-length Apo A-I A to ABCA is compared to the binding affinity of a labeled polypeptide of the invention as described in, e.g., Remaley et al., *J. Lipid Res.*, 44:828-836 (2003). Cells expressing ABCA are incubated in the presence and absence of the competitor compound, and then exposed to a range of concentrations of individual labeled test polypeptides (e.g., a radiolabeled polypeptide of the invention). Typically, the concentrations of test polypeptides will range from about 0.1 µg/ml to about 200 µg/ml, about 0.5 µg/ml to about 100 µg/ml, about 1 µg/ml to about 40 µg/ml, or about 5 µg/ml to about 20 µg/ml.

2. Direct Measurement of ABCA

In some embodiments, the stabilization of ABCA is measured by direct measurement of ABCA (e.g., ABCA protein, or nucleic acid) using a cell based assay. Cell based assays can be performed in any cells in which ABCA is expressed (e.g., J774 macrophages), including cells which have been transfected with ABCA (e.g. HeLa cells). Any cell type can be used. For example, J774 macrophages can be used to assess relative ABCA1 protein levels in the presence and absence of polypeptides of the invention. The cells are first contacted with a compound that will induce ABCA (e.g., cAMP or a cAMP analogue such as, 8-bromo-cAMP) to upregulate ABCA (e.g., ABCA1) expression, then exposed to synthetic ABCA1 protein levels in the presence and absence of polypeptides of the invention in the absence of the cAMP stimulus to evaluate whether ABCA1 protein was stabilized or degraded. Relative levels of ABCA1 protein can be assessed using any means known in the art including, e.g., immunoblot analysis of cell membranes (Oram et al., *J. Biol. Chem.*, 278:52379-52385 (2003)) or hybridization of nucleic acid probes to ABCA mRNA.

C. Screening for Antioxidant Activity

Polypeptides or peptidomimetics of the invention can be screened for antioxidant activity using methods known in the art. For example, U.S. Patent Publication No. 2003/0087819 describes multiple assays that can be used to determine the antioxidant activity of a polypeptide, including, e.g., micelle substrate assays. A micelle substrate comprising a phospholipids (e.g., 1-palmitoyl-2-linoleoylphosphatidylcholine) is used to measure rates of lipid peroxidation catalyzed by specific enzymes (e.g., soybean lipoxygenase and/or xanthine/ xanthine oxidase). The enzymes initiate lipid peroxidation following the addition of recombinant polypeptides of the invention to the phospholipid micelles. Increases in conjugated dienes (a product of lipid peroxidation) are monitored by ultraviolet absorption spectroscopy (234 nm) at 25° C. The mass of phospholipid hydroperoxides is calculated using the molar absorptivity coefficient ($\epsilon$=29,500 Lcm$^{-1}$ mol$^{-1}$) of conjugated dienes. Initial rates of lipoxygenase mediated lipid peroxidation are calculated from the slopes of the linear portion of the oxidation curves and results can be expressed as nmoles of phospholipid peroxide formed/min. Based on the maximum levels of lipid peroxide accumulation obtained in the absence of polypeptide (i.e., the plateau associated with the oxidation curves), it is possible to derive quantitative information regarding the potency of the polypeptides of the invention (e.g., a concentration of polypeptides resulting in 50% protection against lipid peroxidation). Other methods relates to screening for polypeptides capacity to prevent oxidation of ApoB lipoproteins as LDL, VLDL and Lp(A).

Other assays for screening for anti-oxidant activity are disclosed in PCT Publication No. WO 02/15923, the teachings of which are incorporated herein by reference.

D. Screening for Anti-Inflammatory Activity

Polypeptides or peptidomimetics of the invention can be screened for anti-inflammatory activity using any means known in the art. For example, assays to assess the activity of enzymes (e.g., lecithin:cholesterol acetyltransferase (LCAT) or paraoxonase (PON)) sensitive to inflammatory events can be used to assess the anti-inflammatory activity of the polypeptides of the inventions. Suitable assays are described in, e.g., Chen et al., *J. Lipid Res.*, 23:680-691 (1982), which describes quantification of LCAT activity using an exogenous proteoliposome substrate, and Forte et al., *J. Lipid Res.*, 43:477-485 (2002), which describes quantification of PON activity. Other screens can include monitoring the polypeptides capacity to inhibit the mRNA expression and/or protein production of target cells following various stimulations (for example, adhesion molecules, TNF-α, LPS or combinations thereof)

E. Further Testing

Polypeptides that are initially identified as mediating cholesterol efflux or interacting with ABCA can be further tested to validate their ability to mediate cholesterol efflux and/or stabilize ABCA. The basic format of such methods involves administering a lead compound identified during an initial screen to an animal that serves as a model. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like). In a preferred embodiment, Apo E-/- mice, Apo A-II -/- mice, or Apo C-III -/- mice are used. Additional animal models are described in, e.g., Marschang et al., *Sem. Cell Dev. Biol.*, 14:25-35 (2003).

F. High Throughput Screening

In one embodiment, high throughput screening (HTS) methods are used to identify polypeptides or peptidomimetics of the present invention that mediate cholesterol efflux and/or stabilize ABCA. HTS methods involve providing a combinatorial polypeptide library containing a large number of potential therapeutic compounds (i.e., polypeptides or peptidomimetics that mediate cholesterol efflux or stabilize ABCA). Such "libraries" are then screened in one or more assays, as described herein, to identify those library members (i.e., particular polypeptides or peptidomimetics) that display a desired characteristic activity. The compounds thus identified can serve as conventional "lead compounds" or can themselves be used as potential or actual therapeutics.

A combinatorial polypeptide library is a collection of diverse polypeptides generated by either chemical synthesis or biological synthesis, by combining a number of chemical "building blocks," i.e., amino acids. More particularly, a linear combinatorial polypeptide library is formed by combining a set of chemical building blocks (amino acids) in every possible way for a given compound length (i.e., the number of amino acids in a polypeptide compound). Millions of polypeptide compounds can be synthesized through such combinatorial mixing of chemical building blocks. In a preferred embodiment, conservative variants of the polypeptides of SEQ ID NOS:1-11 are generated and screened for desired biological activities (e.g., cholesterol efflux activity) in a high-throughput manner.

Devices for the preparation of combinatorial libraries are known to those of skill in the art and are commercially available from a number of different sources (see, e.g., ECIS™, Applied BioPhysics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

V. Methods of Use

The non-naturally occurring polypeptides of the present invention use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-oxidant activity as well as anti-inflammatory activity, any combination of these activities and, preferably, all of these activities.

In view of their biological activities and, in particular, their ability to mediate cholesterol efflux, the polypeptides of the present invention (or peptidomimetics thereof) can be used to treat elevated cholesterol levels in a mammal, or to treat prophylactically a mammal at risk of developing elevated cholesterol levels. In addition, the polypeptides or peptidomimetics can also be used for improving the lipid parameters in a mammal. An improvement in "lipid parameters" includes, for example, one or more of a decrease in the propensity of lipoproteins to adhere to a blood vessel, a decrease in the amount of atherosclerotic plaque (even though plasma LDL and/or HDL concentrations may not significantly changed), a reduction in the oxidative potential of an HDL or LDL particle, a regression in atherosclerosis (e.g., as measured by carotid angiography or ultrasound) and a reduction in cardiac events. Thus, the polypeptides or peptidomimetics of the present invention can be used to treat or prevent (i.e., prophylactically treat) diseases and conditions associated with dyslipidemia, hypercholesterolemia and inflammation, or diseases and conditions that are treatable by altering lipid parameters, such as those diseases and conditions disclosed herein.

In addition to the diseases and conditions specifically disclosed herein, those of skill in the art will know of other diseases and conditions associated with dyslipidemia, hypercholesterolemia and inflammation that can be treated or prevented using the polypeptides or peptidomimetics of the present invention.

A. Treating or Preventing A Symptom(s) of Atherosclerosis

In one embodiment, the present invention provides methods for treating, ameliorating and/or preventing one or more symptoms of atherosclerosis. The methods preferably involve administering to an organism, preferably a mammal and, more preferably, a human, one or more of the polypeptides of this invention (or peptidomimetics of such polypeptides). The polypeptide(s) can be administered, as described herein, according to any of a number of standard methods including, but not limited to, injection, suppository, nasal spray, time-release implant, transdermal patch, orally and the like. In one particularly preferred embodiment, the polypeptide(s) is administered orally (e.g., as a syrup, capsule, tablet, etc.).

The methods of the present invention are not limited to treating humans or non-human animals having one or more symptom(s) of atherosclerosis (e.g., hypertension, narrowing of vessels, plaque formation and rupture, heart attack, angina, or stroke, high levels of plasma cholesterol, high levels of low density lipoprotein, high levels of very low density lipoprotein, or inflammatory proteins, etc.), but are also very useful in a prophylactic context. Thus, the polypeptides of this invention (or peptidomimetics thereof) can be administered to an organism, such as a human or non-human animal, to prevent the onset, i.e., development, of one or more symptoms of atherosclerosis. Suitable candidate subjects for prophylactic treatment include, for example, those subjects having one or more risk factors for atherosclerosis (e.g., family history, genetic markers that correlate with atherosclerosis, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

Treatment can complement or obviate the need for vascular surgery making anti-atherosclerosis treatment systemic and sustainable. Thus, the peptide can be given before intervention to optimize circulation before surgery, during surgery for regional administration in the vasculature or its vicinity, or post-surgery to lessen inflammation and atherosclerosis caused by mechanical trauma by surgical intervention.

B. Treating or Preventing A Symptom(s) of Atherosclerosis Associated with an Acute Inflammatory Response The atherosclerosis-inhibiting polypeptides of this invention are also useful in a number of other contexts. In particular, it has been found that cardiovascular complications (e.g., atherosclerosis, stroke, etc.) frequently accompany or follow the onset of an acute phase inflammatory response. Such an acute phase inflammatory response is often associated with a recurrent inflammatory disease (e.g., leprosy, tuberculosis, systemic lupus erythematosus, rheumatoid arthritis, etc.), a viral infection (e.g., influenza, HIV, etc.), a bacterial infection, a fungal infection, an organ transplant, a wound or other trauma, an implanted prosthesis, a biofilm, and the like.

In view of their antioxidant activity, the polypeptides described herein can be used to reduce or prevent the formation of oxidized phospholipids during or following an acute phase inflammatory response, thereby mitigating or eliminating cardiovascular complications associated with such a condition.

Thus, in certain embodiments, this invention contemplates administering one or more of the polypeptides of this invention to a subject at risk for, or incurring, an acute phase inflammatory response and/or at risk for or incurring a symptom of atherosclerosis.

The peptides of the invention effects lipids and thereby can be useful for the treatment of disease states in which lipids and lipid metabolism play a role. Thus, for example, a person having or at risk for coronary disease can prophylactically be administered a polypeptide of this invention during flu season. A human (or other animal) subject to a recurrent inflammatory condition, e.g., rheumatoid arthritis, various autoimmune diseases, etc., can be treated with a polypeptide of this invention to mitigate or prevent the development of atherosclerosis or stroke. Similarly, a human (or other animal) subject to trauma, e.g., acute injury, tissue transplant, etc., can be treated with a polypeptide of this invention to mitigate or prevent the development of atherosclerosis or stroke.

In certain instances, such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example, cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase inflammatory response, or risk therefore is evaluated by measuring one or more APPs. Measuring such markers is well known to those of skill in the art, and commercial companies exist that provide such measurement (e.g., AGP measured by Cardiotech Services, Louisville, Ky.). Once it has been determined that a person is experiencing an acute phase inflammatory response or is at risk of experiencing an acute phase inflammatory response, the polypeptides of the present invention can be administered to reduce or prevent the formation of oxidized phospholipids during or following the acute phase inflammatory response, thereby mitigating or eliminating cardiovascular complications associated with such a condition.

C. Treating or Preventing a Symptom(s) or Condition Associated with Coronary Calcification and Osteoporosis It has also been found that oxidized lipids can be a cause of coronary calcification and osteoporosis. It is also thought that oxidized lipids can be involved in the pathogenesis of calcific aortic stenosis.

Thus, in another embodiment, the polypeptides of the present invention are used to treat, inhibit or prevent a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis and the like. In such methods, the polypeptides or peptidomimetics of the present invention can be administered to a human or non-human animal to reduce or prevent the formation of oxidized phospholipids, thereby inhibiting or preventing a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis and the like.

Typically, all of the above methods involve the administration of a single polypeptide of this invention or, alternatively, the administration of two or more different polypeptides of this invention. Such polypeptides can be administered alone or in combination with other therapeutic agents, such as those disclosed herein. The polypeptides can be provided as monomers or in dimeric, oligomeric or polymeric forms. In certain embodiments, the multimeric forms may comprise associated monomers (e.g., ionically or hydrophobically linked); whereas, in other embodiments, other multimeric forms comprise covalently linked monomers (directly linked or through a linker).

In addition, although all of the foregoing methods are described herein with respect to humans, it will be readily apparent to those of skill that such methods are also useful for other animals, i.e., for veterinary use. Thus, preferred organisms include, but are not limited to, humans, non-human primates, canines, equines, felines, porcines, ungulates, largomorphs, and the like.

D. Stabilization of Vulnerable Plaques

As explained herein, heart disease, specifically coronary artery disease, is a major cause of death, disability, and healthcare expense in the United States and other industrialized countries. Until recently, most heart disease was considered to be primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot (thrombus). The clot may choke off the flow of oxygen-rich blood (ischemia) to heart muscles, causing a heart attack. Alternatively, the clot may break off and lodge in the vessel of another organ, such as the brain, resulting in a thrombotic stroke.

Within the past decade, however, evidence has emerged changing to some extent the paradigm of atherosclerosis, coronary artery disease, and heart attacks. While the buildup of hard plaque may produce angina and severe ischemia in the coronary arteries, new clinical data suggest that the rupture of vulnerable plaques, which are often non-occlusive, per se, causes the vast majority of heart attacks. The rate is estimated as high as 60-80 percent.

In many instances, vulnerable plaques do not impinge on the vessel lumen; rather, much like an abscess, they are ingrained within the arterial wall. The majority of vulnerable plaques include a lipid pool, smooth muscle (endothelial) cells, and a dense infiltrate of cholesterol filled macrophages/foam cells contained by a thin fibrous cap. The lipid pool is believed to be formed as a result of pathological process involving low density lipoprotein (LDL), macrophages, and the inflammatory process. The macrophages oxidize the LDL, producing foam cells.

The macrophages, foam cells and associated endothelial cells release various substances, such as tumor necrosis factor, tissue factor, and matrix proteinases, which result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque may then spill into the blood stream, thereby initiating a clotting cascade. The cascade produces a blood clot that potentially results in a heart attack and/or stroke. The process is exacerbated due to the release of collagen and plaque components (e.g., collagen and tissue factor), which enhance clotting upon their release.

It has been found that the polypeptides of the present invention can stabilize vulnerable plaques by reducing plaque lipid content through reverse cholesterol transport. Thus, in another embodiment, the present invention provides methods for stabilizing a vulnerable plaque in a blood vessel of a mammal by administering to the mammal (and, more preferably, a human), one or more of the polypeptides of this invention (or peptidomimetics of such polypeptides). A "vulnerable" plaque is generally defined as a lipid-rich plaque with a thinned fibrous cap lacking proper collagen and smooth muscle cell support. Again, the polypeptides of the present invention can reduce plaque lipid content, thereby stabilizing such "vulnerable" plaques.

In one embodiment, the mammal is a mammal diagnosed as having one or more vulnerable plaques. In this embodiment, a number of different diagnostic assays have been developed for the detection (e.g., diagnosis and localization) of vulnerable plaques, including temperature detection strategies, labeling strategies, imaging strategies (e.g., devices utilizing magnetic resonance, ultrasound, infra-red, fluorescence, visible light, radio waves, x-ray, etc.), general strategies for discriminating the vulnerable plaque from surround healthy vascular tissue and the like (see, e.g., U.S. Pat. Nos. 6,245,026, 6,475,159, 6,475,210 and 7,118,567). One strategy involves the measurement of temperature within a blood vessel. For example, vulnerable plaque tissue temperature is generally elevated compared to healthy vascular tissue. Measurement of this temperature discrepancy allows detection of the vulnerable plaque. Another detection strategy involves labeling vulnerable plaque with a marker. The marker can be a substance specific for a component and/or characteristic of the vulnerable plaque (such as C-reactive protein). For example, the marker may have an affinity for the vulnerable plaque, more so than for healthy tissue. Detection of the marker may thus allow detection of the vulnerable plaque. Alternatively, the marker may not necessarily have an affinity for the vulnerable plaque, but will simply change properties while associated with the vulnerable plaque. The property change may be detected and thus allow detection of the vulnerable plaque.

In another embodiment, the mammal is at risk of having one or more vulnerable plaques. In this embodiment, a clinical symptom has developed and/or a clinical event has occurred that leads one of skill in the art to believe that the mammal is at risk of having one or more vulnerable plaques.

In connection with the above methods of stabilizing a vulnerable plaque, the polypeptide(s) can be administered, as described herein, according to any of a number of standard methods including, but not limited to, injection, infusion, suppository, nasal spray, time-release implant, transdermal patch, orally and the like. In one particularly preferred embodiment, the polypeptide(s) is administered orally (e.g., as a syrup, capsule, tablet, etc.). In addition, the polypeptides (or peptidomimetics) of the present invention can be used alone or in combination with other known pharmaceutical agents for the treatment of dyslipidemia, hypercholesterolemia and inflammation to raise plasma HDL concentrations and/or to promote reverse cholesterol transport.

VI. Combination Therapy

In some embodiments, the polypeptides or peptidomimetics of the present invention are administered in combination with one or more additional therapeutic agents for treating or preventing diseases and disorders associated with dyslipidemia, hypercholesterolemia and inflammation, such as cardiovascular disease, including atherosclerosis. For instance, in one embodiment, a polypeptide of the present invention is administered in conjunction with any of the standard treatments for atherosclerosis including, for example, statins (e.g., atorvastatin, lovastatin, pravastatin, simvastatin, fluvastatin, or rosuvastatin); a Nieman-Pick C1-Like 1 sterol transporter channel inhibitor (e.g., Ezetimibe); bile acid binders (e.g., cholestyramine or colestipol); platelet clumping inhibitors (e.g., aspirin, ticlopidine, or clopidogrel); niacin/nicotinamide; PPAR activators; Vitamin E; surgical intervention (e.g., angioplasty, stents, stents, or endarterectomy); and lifestyle changes (e.g., low-fat diets, weight loss, and exercise).

More particularly, the polypeptides or peptidomimetics of the present invention can be used in combination, either as separate units or fixed combinations, with one or more of the following: an antibody which binds to an unwanted inflammatory molecule or cytokine such as interleukin-6, interleukin-8, granulocyte macrophage colony stimulating factor, and tumor necrosis factor-$\alpha$; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen or acetaminophen; or a non-inflammatory cytokine such as interleukin-4 or interleukin-10. Other cytokines and growth factors such as interferon-$\beta$, tumor necrosis factors, antiangiogenic factors, erythropoietins, thrombopoietins, interleukins, maturation factors, chemotactic protein, and their variants and derivatives that retain similar physiological activities may also be used as an additional therapeutic agents.

The polypeptides or peptidomimetics of the present invention can be used in combination with drugs commonly used to treat lipid disorders in, for example, diabetic patients. Such drugs include, but are not limited to, HMG-CoA reductase inhibitors, nicotinic acid, ezetimide, bile acid sequestrants, fibric acid derivatives, MTP inhibitor, ACAT inhibitor and CETP inhibitors. Examples of HMG-CoA reductase inhibitors include lovastatin, pravastatin, simvastatin, rosuvastatin, fluvastatin and atorvastatin. Examples of bile acid sequestrants include cholestyramine, colestipol and colesevelam. Examples of fibric acid derivatives include gemfibrozil and fenofibrate, The polypeptides or peptidomimetics of the invention can also be used in combination with anti-hypertensive drugs, such as, for example, diuretics, $\beta$-blockers, cathepsin S inhibitors, methyldopa, $\alpha$2-adrenergic agonists, guanadrel, reserpine, $\beta$-adrenergic receptor antagonists, $\alpha$ 1-adrenergic receptor antagonists, hydralazine, minoxidil, calcium channel antagonists, ACE inhibitors and angiotensin II-receptor antagonists. Examples of $\beta$-blockers include acebutolol, bisoprolol, esmolol, propanolol, atenolol, labetalol, carvedilol and metoprolol. Examples of ACE inhibitors include captopril, enalapril, lisinopril, benazepril, fosinopril, ramipril, quinapril, perindopril, trandolapril and moexipril.

The polypeptides or peptidomimetics of the invention can also be used in combination with cardiovascular drugs such as calcium channel antagonists, $\beta$-adrenergic receptor antagonists and agonists, aldosterone antagonists, ACE inhibitors, angiotensin II receptor antagonists, nitrovasodilators, and cardiac glycosides. The polypeptides or peptidomimetics of the invention can also be used in combination with anti-inflammatory drugs such as H1-receptor antagonists, H2-receptor mediated agonists and antagonists, COX-2 inhibitors, NSAID, salicylates, acetaminophen, propionic acid derivatives, enolic cids, diaryl substituted fuanones, cyclooxygenase inhibitors, and bradykinin agonists and antagonists.

Other therapeutic agents suitable for use in combination with the polypeptides or peptidomimetics of the present invention are disclosed in U.S. Patent Application Publication No. 2005/0142180, which was published Jun. 30, 2005, the teachings of which are incorporated herein by reference.

The polypeptide (or peptidomimetics thereof) and the additional therapeutic agent can be administered simultaneously or sequentially. For example, the polypeptide may be administered first, followed by the additional therapeutic agent. Alternatively, the additional therapeutic agent may be administered first, followed by the polypeptide of the invention. In some cases, the polypeptide of the invention and the additional therapeutic agent are administered in the same formulation. In other cases, the polypeptide and the additional therapeutic agent are administered in different formulations. When the polypeptide and the additional therapeutic agent are administered in different formulations, their administration may be simultaneous or sequential.

VII. Pharmaceutical Formulations

In order to carry out the methods of the invention, one or more polypeptides of this invention or peptidomimetics thereof are administered to an individual diagnosed as having or at risk of having a disease or disorder associated with dyslipidemia, hypercholesterolemia and inflammation (e.g., to an individual diagnosed as having one or more symptoms of atherosclerosis, or as being at risk for atherosclerosis). The polypeptides or peptidomimetics thereof can be administered in their "native" form or, if desired, in the form of, for example, salts, esters, amides, prodrugs, derivatives, and the like, provided that the salt, ester, amide, prodrug or derivative is suitable pharmacologically, i.e., effective in the methods of the present invention.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectibles, implantable sustained-release formulations, etc.

As such, in another aspect, the present invention provides pharmaceutical compositions comprising a pharmaceutically effective amount of a polypeptide or peptidomimetic of the present invention and an acceptable carrier and/or excipients. A pharmaceutically acceptable carrier includes any solvents, dispersion media, or coatings that are physiologically compatible and that preferably does not interfere with or otherwise inhibit the activity of the polypeptide or peptidomimetic. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include, but are not limited to, wetting agents, emulsifying agents, dispersing agents or preservatives which are particularly useful for preventing the growth or action of microorganisms. Various preservatives are well known and include, for example, phenol and ascorbic acid. One skilled in the art will appreciate that the choice of pharmaceutically acceptable carrier(s), including a physiologically acceptable compound depends, for example, on the route of administration of the polypeptide(s) or peptidomimetic(s) and on the particular physiochemical characteristics of the polypeptide(s) or peptidomimetic(s).

In a preferred embodiment, the pharmaceutically acceptable carrier is physiological saline. Other pharmaceutically acceptable carriers and their formulations are well-known and generally described in, for example, Remington's Pharmaceutical Science (18$^{th}$ Ed., ed. Gennaro, Mack Publishing Co., Easton, Pa., 1990). Various pharmaceutically acceptable excipients are well-known in the art and can be found in, for example, Handbook of Pharmaceutical Excipients (4$^{th}$ ed., Ed. Rowe et al., Pharmaceutical Press, Washington, D.C.). Again, the pharmaceutical composition can be formulated as a solution, microemulsion, liposome, capsule, tablet, or other suitable form. The active component may be coated in a material to protect it from inactivation by the environment prior to reaching the target site of action.

In certain preferred embodiments, the polypeptides or peptidomimetics of this invention can be administered orally (e.g., via a tablet) or as an injectable in accordance with standard methods well known to those of skill in the art. In other preferred embodiments, the polypeptides or peptidomimetics can also be delivered through the skin using conventional transdermal drug delivery systems, i.e., transdermal "patches," wherein the polypeptide(s) or peptidomimetic(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

In some embodiments, implanted devices (e.g., arterial and intravenous stents, including eluting stents, and catheters) are used to deliver the formulations comprising the polypeptides and peptidomimetics of the invention. For example, aqueous solutions comprising the polypeptides and peptidomimetics of the invention are administered directly through the stents and catheters. In some embodiments, the stents and catheters may be coated with formulations comprising the polypeptides and peptidomimetics described herein. In some embodiments, the polypeptides and peptidomimetics will be in time-release formulations an eluted from the stents. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829,497; 6,827,798; 6,827,730; 6,827,703; 6,824,554; 6,824,553; 6,824,551; 6,824,532; and 6,819,951.

Unlike typical polypeptide formulations, the polypeptides of this invention comprising L-form or D-form amino acids can be administered, even orally, without protection against proteolysis by stomach acid, etc. Nevertheless, in certain embodiments, polypeptide delivery can be enhanced by the use of protective excipients. This is typically accomplished either by complexing the polypeptide with a composition to render it resistant to acidic and enzymatic hydrolysis, or by packaging the polypeptide in an appropriately resistant carrier such as a liposome. Means of protecting polypeptides for oral delivery are well known in the art (see, e.g., U.S. Pat. No. 5,391,377, which describes lipid compositions for oral delivery of therapeutic agents).

Elevated serum half-life can be maintained by the use of sustained-release polypeptide "packaging" systems. Such sustained release systems are well known to those of skill in the art. In one preferred embodiment, the ProLease biodegradable microsphere delivery system for proteins and polypeptides is used (Tracy, *Biotechnol. Prog.*, 14:108 (1998); Johnson et al., *Nature Med.*, 2:795 (1996); Herbert et al., *Pharmaceut. Res.*, 15:357 (1998)), which involves the use of a dry powder composed of biodegradable polymeric microspheres containing the polypeptide in a polymer matrix that can be compounded as a dry formulation with or without other agents.

The ProLease microsphere fabrication process was designed to achieve a high polypeptide encapsulation efficiency while maintaining protein integrity. The process consists of (i) preparation of freeze-dried protein particles from bulk polypeptide by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the polypeptide, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., $-40°$ C.). During encapsulation, the polypeptide is maintained in the solid state in the absence of water, thus minimizing water-induced conformational mobility of the polypeptide, preventing polypeptide degradation reactions that include water as a reactant, and avoiding organic-aqueous interfaces where polypeptides may undergo denaturation. A preferred process uses solvents in which most polypeptides are insoluble, thus yielding high encapsulation efficiencies (e.g., greater than 95%).

In another embodiment, one or more components of the solution can be provided as a "concentrate," e.g., in a storage container (e.g., in a premeasured volume) ready for dilution, or in a soluble capsule ready for addition to a volume of water.

In certain embodiments of the present invention, the pharmaceutical compositions are sustained release formulations. Polypeptides or peptidomimetics of the present invention may be admixed with biologically compatible polymers or matrices which control the release rate of the copolymers into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. Acceptable carriers include carboxymethyl cellulose (CMC) and modified CMC.

The pharmaceutical composition of the present invention is preferably sterile and non-pyrogenic at the time of delivery, and is preferably stable under the conditions of manufacture and storage. These pharmaceutical compositions can be sterilized by conventional, well known sterilization techniques.

In therapeutic applications, the compositions of this invention are administered to an individual diagnosed as having or at risk of having a disease or disorder associated with dyslipidemia, hypercholesterolemia and inflammation (and, in preferred embodiments, to an individual diagnosed as having one or more symptoms of atherosclerosis or as being at risk for atherosclerosis) in an amount sufficient to cure or at least partially prevent or arrest the disease, condition and/or its complications. An amount adequate to accomplish this is defined as a "therapeutically effective dose." Amounts effective for this use will depend upon the severity of the disease and the general state of the patient's health. Single or multiple administrations of the compositions can be administered depending on the dosage and frequency as required and tolerated by the patient. In any event, the composition should provide a sufficient quantity of the active agents, i.e., polypeptides or peptidomimetics, of the formulations of this invention to effectively treat (ameliorate one or more symptoms) the individual or patient.

The concentration of polypeptide or peptidomimetic can vary widely, and will be selected primarily based on fluid volumes, viscosities, body weight, circulating plasma levels of the polypeptide, polypeptide toxicities, progression of the disease (e.g., atherosclerosis), the production of antibodies that specifically bind to the polypeptide, and the like in accordance with the particular mode of administration selected and the patient's needs. Typically, the dose equivalent of a polypeptide or peptidomimetic is from about 0.1 to about 50 mg per kg, preferably from about 1 to about 25 mg per kg, most preferably from about 1 to about 20 mg per kg body weight. It will be appreciated that such dosages may be varied to optimize a therapeutic regimen in a particular subject or group of subjects.

For administration, polypeptides of the present invention can be administered at a rate determined by the LD50 of the polypeptide, and the side-effects of the polypeptide at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

As explained herein, the polypeptides or peptidomimetics of the present invention can be modified in a number of different ways. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. In addition, to enhance delivery and/or biological activities in vivo, salts, esters, amides, prodrugs and other derivatives of the polypeptides or peptidomimetics of the present invention can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology, which typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the polypeptides described herein are halide salts, such as may be prepared using hydrochloric or hydrobromic acids. Conversely, preparation of basic salts of the polypeptides or peptidomimetics of the present invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., sodium salts and copper salts.

Preparation of esters typically involves functionalization of hydroxyl and/or carboxyl groups that may be present within the polypeptides or peptidomimetics of the present invention. The esters are typically acyl-substituted derivatives of free alcohol groups, i.e., moieties that are derived from carboxylic acids of the formula RCOOH, wherein R is alkyl and, preferably, lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The foregoing formulations and administration methods are clearly intended to be illustrative and not limiting in any way. It will be appreciated that, using the teaching provided herein, other suitable formulations and modes of administration can be readily devised.

VIII. Lipid-Based Formulations

In another aspect, the polypeptides and peptidomimetics of the present invention are preferably administered in conjunction with one or more lipids. The lipids can be formulated as an excipient to protect and/or enhance transport/uptake of the polypeptides or peptidomimetics or they can be administered separately.

The lipids can be formulated into liposomes, nanocapsules, microparticles, microspheres, lipids particles, lipid vesicles and the like. Such lipid formulations can be used to encapsulated the polypeptides and peptidomimetics of the present invention and/or they can be simply complexed/admixed with such polypeptides and peptidomimetics. Those of skill in the art will know how to use such lipid formulations to either encapsulate or complex the polypeptides or peptidomimetics of the present invention. For instance, the formation and use of liposomes is generally known to those of skill in the art. Recently, liposomes were developed with improved serum stability and circulation half-times (see, U.S. Pat. No. 5,741, 516). Further, various methods of liposome and liposome-like preparations as potential drug carriers have been reviewed (see, U.S. Pat. Nos. 5,567,434; 5,552,157; 5,565, 213; 5,738,868 and 5,795,587).

In one embodiment, the polypeptides or peptidomimetics of the present invention are complexed with a lipid, such as a phospholipid (e.g., 1-palmitoyl-2-oleoyl-sn-glycerol-phosphatidylcholine ("POPC") in a manner similar to that disclosed in U.S. Patent Application Publication No. 2005/0142180, which was published Jun. 30, 2005, the teachings of which are incorporated herein by reference. It has surprisingly been found that when the polypeptides and peptidomimetics of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells.

As such, the present invention provides polypeptide-lipid complexes (or, alternatively, peptidomimetic-lipid complexes) having an increased ability to efflux cholesterol from cells. Typically, the lipid is mixed with the polypeptide prior to administration. The polypeptides of the present invention and lipids can be mixed in an aqueous solution in appropriate ratios and can be complexed by methods known in the art, including, but not limited to, freeze-drying, detergent solubilization followed by dialysis, microfluidization, sonication, and homogenization. Complex efficiency can be optimized, for example, by varying pressure, ultrasonic frequency or detergent concentration. An example of a detergent commonly used to prepare polypeptide-lipid complexes is sodium cholate.

In certain embodiments, the polypeptide-lipid (e.g., phospholipids) complex can be in solution with an appropriate pharmaceutical diluent or carrier. In other embodiments, freeze-dried or lyophilized preparations of the polypeptide-lipid complexes can be hydrated or reconstituted with an appropriate pharmaceutical diluent prior to administration. In another embodiment, the polypeptide-lipid complexes can be frozen preparations that are thawed until a homogenous solution is achieved prior to administration to a subject in need thereof.

The lipid can be any suitable lipid known to those of skill in the art. In one embodiment, non-phosphorus containing lipids can be used, including stearylamine, dodecylamine, acetyl palmitate, (1,3)-D-mannosyl-(1,3)digly-ceride, aminophenylglycoside, 3-cholesteryl-6'-(glycosylthio)hexyl ether glycolipids, N-(2,3-di(9-(Z)-octadecenyloxy))-prop-1-yl-N,N,N-trimethylammonium chloride and fatty acid amides.

In another embodiment, a phospholipids or a mixture of phospholipids is used. Suitable phospholipids include, but are not limited to, can be a small alkyl chain phospholipid, phosphatidylcholine, egg phosphatidylcholine, soybean phosphatidylcholine, dipalmitoylphosphatidylcholine, soy phosphatidylglycerol, egg phosphatidylglycerol, distearoylphosphatidylgly-cerol, dimyristoylphosphatidylcholine, distearoylphosphatidylcholine, dilaurylphosphatidylcholine, 1-myristoyl-2-palmitoylphosphatidylcholine, 1-palmitoyl-2-myristoylphosphatidylcholine, 1-palmitoyl-2-stearoylphospha-tidylcholine, 1-stearoyl-2-palmitoylphosphatidylcholine, dioleoylphosphatidylcholine, 1-palmitoyl-2-oleoylphosphatidylcholine, 1-oleoyl-2-palmitylphosphatidylcholine, dioleoylphosphatidylethanolamine, dilauroylphosphatidylglycerol, phosphatidylserine, phosphatidylethanolamine, phosphatidylinositol, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, phosphatidic acid, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, sphingolipids, brain sphingomyelin, dipalmitoylsphingomyelin, distearoylsphingomyelin, galactocerebroside, gangliosides, cerebrosides, phosphatidylglycerol, phosphatidic acid, lysolecithin, lysophosphatidylethanolamine, cephalin, cardiolipin, dicetylphosphate, distearoyl-phosphatidylethanolamine and cholesterol and its derivatives. Similarly, the phospholipid can be a derivative or analogue of any of the foregoing phospholipids or, again, a mixture of two or more of any of the foregoing phospholipids. Such phospholipids can be obtained from commercial sources, natural sources or by synthetic or semi-synthetic means known to those of skill in the art.

In preferred embodiments, the polypeptide-lipid complex is a polypeptide-phospholipid-complex. In a more preferred embodiment, the lipid is 1-palmitoyl-2-oleoyl phosphatidylcholine ("POPC") or ("1-palmitoyl-2-oleoyl-sn-glycero-3-phosphocholine").

It will be readily apparent to those of skill in the art that the complex comprising a polypeptide of the present invention and a lipid, preferably a phospholipids, can comprise any amount of lipid and any amount of the polypeptide, provided the complex is effective to mediate cholesterol efflux and, in turn, to treat diseases or symptoms associate therewith. As previously mentioned, it has surprisingly been found that when the polypeptides of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells. However, the polypeptide-lipid complexes of the present invention can comprise complexes with other ratios of phospholipid to polypeptide, such as about 100:1, about 10:1, about 5:1, about 3:1, about 2:1, about 1:1, about 1:2, about 1:3, about 1:5, about 1:10 and about 1:100 (wt of polypeptide/wt of lipid).

The polypeptide-lipid complexes of the present invention can be made by any method known to one of skill in the art. In some cases, it is desirable to mix the lipid and the polypeptide prior to administration. Lipids can be in solution or in the form of liposomes or emulsions formed using standard techniques, such as homogenization, sonication or extrusion. Sonication is generally performed with a tip sonifier, such as a Branson tip sonifier, in an ice bath. Typically, the suspension is subjected to several sonication cycles. Extrusion can be carried out by biomembrane extruders, such as the Lipex Biomembrane Extruder™ (Lipex Biomembrane Extruder, Inc. Vancouver, Canada). Defined pore size in the extrusion filters can generate unilamellar liposomal vesicles of specific sizes. The liposomes can also be formed by extrusion through an asymmetric ceramic filter, such as a Ceraflow Microfilter™, which is commercially available from the Norton Company, Worcester, Mass., or through a polycarbonate filter or other types of polymerized materials (i.e., plastics) known to those of skill in the art.

As previously mentioned, the polypeptide-lipid complexes of the present invention can be prepared in a variety of forms including, but not limited to, vesicles, liposomes or proteoliposomes. A variety of methods well known to those skilled in the art can be used to prepare the polypeptide-lipid complexes. A number of available techniques for preparing liposomes or proteoliposomes can be used. For example, a polypeptide of the present invention (e.g., a polypeptide of SEQ ID NOS:1-11 and, preferably, a polypeptide of SEQ ID NOS:4-7) can be co-sonicated (using a bath or probe sonicator) with the appropriate lipid to form the polypeptide-lipid complexes. In certain embodiments, the polypeptide can be combined with preformed lipid vesicles resulting in the spontaneous formation of an polypeptide-lipid complex. In another embodiment, the polypeptide-lipid complex can also be made by a detergent dialysis method. In this method, a mixture of the polypeptide, lipid and a detergent, such as sodium cholate, can be dialyzed to remove the detergent and reconstituted to make the polypeptide-lipid complexes (see, e.g., Jonas et al., *Methods Enzymol.*, 128:553-82 (1986)).

In other embodiments, the polypeptide-lipid complexes can be made by co-lyophilization as described in U.S. Pat. Nos. 6,287,590 and 6,455,088, the teachings of both of which are hereby incorporated by reference in their entirety. Other methods are disclosed in, for example, U.S. Pat. Nos. 6,004, 925, 6,037,323 and 6,046,166, the teachings of all of which are incorporated herein by reference in their entireties. Other methods of preparing polypeptide-lipid complexes will be apparent to those of skill in the art.

In one preferred embodiment, the polypeptide-lipid complexes can be made by homogenization.

IX. Nucleic Acids and Gene Therapy

In another embodiment, the present invention provides isolated nucleic acids encoding the polypeptides disclosed herein, expression vectors comprising the nucleic acids, and host cells comprising the expression vectors. More particularly, the present invention provides isolated nucleic acids encoding the polypeptides of the present invention having cholesterol efflux activities similar to full-length apolipoproteins, on a per molecule basis, and having high selectivity for ABAC1 in a manner similar to full-length apolipoproteins, the polypeptides including, but not limited to, the polypeptides having an amino acid sequence comprising SEQ ID NOS:1-11.

In certain embodiments, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with dyslipidemia, hypercholesterolemia and inflammation.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science*, 256:808-813 (1992); Nabel et al., *TIBTECH*, 11:211-217 (1993); Mitani et al., *TIBTECH*, 11:162-166 (1993); Mulligan, *Science*, 926-932 (1993); Dillon, *TIBTECH*, 11:167-175 (1993); Miller, *Nature*, 357:455-460 (1992); Van Brunt, *Biotechnology*, 6(10):1149-1154 (1998); Vigne, *Restorative Neurology and Neuroscience*, 8:35-36 (1995); Kremer et al., *British Medical Bulletin*, 51(1):31-44 (1995); Haddada et al., in *Current Topics in Microbiology and Immunology* (Doerfler & Böhm eds., 1995); and Yu et al., *Gene Therapy*, 1:13-26 (1994)).

For delivery of nucleic acids, viral vectors may be used. Suitable vectors include, for example, herpes simplex virus vectors as described in Lilley et al., *Curr. Gene Ther.*, 1(4): 339-58 (2001), alphavirus DNA and particle replicons as described in e.g., Polo et al., *Dev. Biol.* (Basel), 104:181-5 (2000), Epstein-Barr virus (EBV)-based plasmid vectors as described in, e.g., Mazda, *Curr. Gene Ther.*, 2(3):379-92 (2002), EBV replicon vector systems as described in e.g., Otomo et al., *J. Gene Med.*, 3(4):345-52 (2001), adenovirus associated viruses from rhesus monkeys as described in e.g., Gao et al., *PNAS USA.*, 99(18):11854 (2002), adenoviral and adeno-associated viral vectors as described in, e.g., Nicklin et al., *Curr. Gene Ther.*, 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al., *Mol. Cell. Biol.*, 8:3988-3996 (1988); Vincent et al. (1990) *Vaccines* 90 (Cold Spring Harbor Laboratory Press); Carter, *Current Opinion in Biotechnology* 3:533-539 (1992); Muzyczka, *Current Topics in Microbiol. and Immunol.*, 158:97-129 (1992); Kotin, *Human Gene Therapy*, 5:793-801 (1994); Shelling et al., *Gene Therapy*, 1:165-169 (1994); and Zhou et al., *J. Exp. Med.*, 179:1867-1875 (1994)). Additional suitable vectors include E1B gene-attenuated replicating adenoviruses described in, e.g., Kim et al., *Cancer Gene Ther.*, 9(9): 725-36 (2002) and nonreplicating adenovirus vectors described in e.g., Pascual et al., *J. Immunol.*, 160(9):4465-72 (1998) Exemplary vectors can be constructed as disclosed by Okayama et al., *Mol. Cell. Biol.*, 3:280 (1983).

Molecular conjugate vectors, such as the adenovirus chimeric vectors described in Michael et al., *J. Biol. Chem.*, 268:6866-6869 (1993) and Wagner et al., *Proc. Natl. Acad. Sci. USA*, 89:6099-6103 (1992), can also be used for gene delivery according to the methods of the invention.

In one illustrative embodiment, retroviruses provide a convenient and effective platform for gene delivery systems. A selected nucleotide sequence encoding a polypeptide of the invention is inserted into a vector and packaged in retroviral particles using techniques known in the art. The recombinant virus can then be isolated and delivered to a subject. Suitable vectors include lentiviral vectors as described in e.g., Scherr et al., *Curr. Gene Ther.*, 2(1):45-55 (2002). Additional illustrative retroviral systems have been described (e.g., U.S. Pat. No. 5,219,740; Miller et al., *BioTechniques*, 7:980-990 (1989); Miller, *Human Gene Therapy*, 1:5-14 (1990); Scarpa et al., *Virology*, 180:849-852 (1991); Burns et al., *Proc. Natl. Acad. Sci. USA*, 90:8033-8037 (1993); and Boris-Lawrie et al., *Curr. Opin. Genet. Develop.*, 3:102-109 (1993).

Other known viral-based delivery systems are described in, e.g., Fisher-Hoch et al., *Proc. Natl. Acad. Sci. USA*, 86:317-321 (1989); Flexner et al., *Ann. N.Y. Acad. Sci.*, 569:86-103 (1989); Flexner et al., *Vaccine*, 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques*, 6:616-627 (1988); Rosenfeld et al., *Science*, 252:431-434 (1991); Kolls et al., *Proc. Natl. Acad. Sci. USA*, 91:215-219 (1994); Kass-Eisler et al., *Proc. Natl. Acad. Sci. USA*, 90:11498-11502 (1993); Guzman et al., *Circulation*, 88:2838-2848 (1993); Guzman et al., *Cir. Res.*, 73:1202-1207 (1993); and Lotze et al., *Cancer Gene Ther.*, 9(8):692-9 (2002).

X. Use as Research Tools and in Methods of Diagnosis

The polypeptides and peptidomimetics of the invention are also useful as research tools. For example, the polypeptides or peptidomimetics of the invention can be used for investigating lipoprotein-receptor interactions in animals and animal models, particularly when a polypeptide or peptidomimetic thereof is labeled with a detectable moiety, e.g., a radioactive label, a fluorescent label, etc. In addition, the polypeptides of the invention can also be used to identify appropriate animal models for elucidation of lipid metabolic pathways. For example, the polypeptides can be used to identify animal models where lipid peroxidation contributes to the progression of atherosclerosis. Moreover, the polypeptides of the invention can be used to evaluate the anti-atherosclerotic potential of other compounds (including, e.g., polypeptide variants and other peptidomimetics).

In some cases, the polypeptides or peptidomimetics of the invention are used to target therapeutic agents to cells and tissues expressing ABCA.

In other embodiments, the polypeptides or peptidomimetics of the invention can be used in methods of diagnosing diseases and disorders associated with aberrant cholesterol efflux or with ABCA. For example, the peptides can be used in assays to diagnose reverse cholesterol transport deficiency and to identify individuals predicted to be responders to peptide treatment. Such diagnostic assays include in vitro assays. For example, cholesterol efflux can be evaluated in an assay in which a polypeptide of the invention, e.g., any one of SEQ ID NO:1-15, is mixed with plasma from a subject and exposed to cells to indicate whether a subject would respond to treatment (e.g., a large increase in efflux in the presence of the peptide compared with plasma-mediated efflux in the absence of the peptide suggests that the subject would be responsive). Similarly, a polypeptide of the invention, e.g., any one of SEQ ID NO:1-15, can be mixed with plasma from a subject to detect changes in HDL subclass distribution and/or to detect changes in anti-oxidative properties of the plasma in the presence of the peptide.

In some embodiments, the polypeptides or peptidomimetics are used for in vivo imaging methods. The polypeptides or peptidomimetics are conjugated to a detectable moiety and administered to a subject (e.g., a mammal such as a human). Detection of the detectable moiety allows imaging of a cell, tissue, or organ of interest, including, e.g., an atherosclerotic lesion or an amyloid plaque.)

The term "imaging" refers to a procedure or modality for generating an image of a detectable moiety in vivo, ex vivo, or in vitro as described herein or known to one of skill in the art. Examples of imaging modalities include, but are not limited to, magnetic resonance, nuclear magnetic resonance, radioscintigraphy, positron emission tomography, computed tomography, near-infrared fluorescence, X-ray, ultra sound, ultraviolet light, or visible light (see, e.g., Dahnhert, Radiology Review Manual (4th ed. 1999); Brant et al., Fundamentals of Diagnostic Radiobiology (2nd ed. 1999); Weissleder et al., Primer of Diagnostic Imaging (2nd ed. 1997); Buddinger et al., Medical Magnetic Resonance A Primer, Society of Magnetic Resonance, Inc. (1988); and Weissleder et al., *Nature Biotech.*, 17:375-378 (1999)).

The phrase "detectable moiety," as used herein, refers to a moiety or label that can be imaged and/or detected in vivo, ex vivo, or in vitro by a procedure or modality described herein or known to one of skill in the art. As used herein, the detectable moiety can be directly or indirectly linked to a polypeptide or peptidomimetic of the invention. A linker may serve to link the polypeptide or peptidomimetic to one detectable moiety. Alternatively, a linker may link the polypeptide to more than one detectable moiety. Likewise, a detectable moiety may be linked to more than one linker. The use of a plurality of detectable moieties attached to one polypeptide enables the detectability of the detectable moiety to be increased (e.g., by increasing its radiopacity, echogenicity or relaxivity) or, alternatively, it may enable the polypeptide to be detected in more than one imaging modality.

Linking of a detectable moiety to a polypeptide or peptidomimetic of the invention may be achieved by covalent or non-covalent means, usually involving interaction with one or more functional groups located on the detectable moiety, the linker and/or the polypeptide. Examples of chemically reactive functional groups that may be employed for this purpose include, but are not limited to, amino, hydroxyl, sulfhydryl, carboxyl, and carbonyl groups, as well as carbohydrate groups, vicinal dials, thioethers, 2-amino alcohols, 2-amino thiols, guanidinyl, imidazolyl and phenolic groups. In some embodiments, labile linkages, e.g., containing spacer arms that are biodegradable or chemically sensitive or which incorporate enzymatic cleavage sites, are used. The particular linker is not a critical aspect of the invention. Any linker known in the art may be used as long it binds the polypeptide or peptidomimetic and the detectable moiety together for an adequate period, i.e., a period sufficient for the polypeptide the desired target and be detected.

The detectable moieties used in the methods of the present invention can be any moiety capable of detection either directly or indirectly in an imaging procedure described herein or known to one of skill in the art. For example, the following detectable moieties may be used: moieties which emit or may be caused to emit detectable radiation (e.g., by radioactive decay, fluorescence excitation, spin resonance excitation, etc.), moieties which affect local electromagnetic fields (e.g., paramagnetic, superparamagnetic, ferrimagnetic or ferromagnetic species), moieties which absorb or scatter radiation energy (e.g., chromophores, particles (including gas or liquid containing vesicles), heavy elements and compounds thereof, etc.), and moieties which generate a detectable substance (e.g., gas microbubble generators).

A very wide range of materials detectable by imaging modalities is known from the art and the detectable moiety will be selected according to the imaging modality to be used. Thus, for example, for ultrasound imaging, an echogenic material or a material capable of generating an echogenic material will normally be selected; for X-ray imaging, the detectable moiety will generally be or contain a heavy atom (e.g., of atomic weight 38 or above); for MR imaging, the detectable moiety will either be a non zero nuclear spin isotope (such as $^{19}$F) or a material having unpaired electron spins and hence paramagnetic, superparamagnetic, ferrimagnetic or ferromagnetic properties; for light imaging, the detectable moiety will be a light scatterer (e.g., a colored or uncolored particle), a light absorber or a light emitter; for magnetometric imaging, the detectable moiety will have detectable magnetic properties; for electrical impedance imaging, the detectable moiety will affect electrical impedance; and for scintigraphy, SPECT, PET, etc., the detectable moiety will be a radionuclide.

Examples of suitable detectable moieties that are well known from the diagnostic imaging literature include, e.g., magnetic iron oxide particles, gas-containing vesicles, chelated paramagnetic metals (such as Gd, Dy, Mn, Fe, etc.) (see, for example, U.S. Pat. Nos. 5,228,446; 4,647,447; 4,863,715; 4,770,183, and 5,387,080; PCT Publication No. WO 97/25073, WO 96/09840, WO 85/02772, WO 92/17212, WO 97/29783, WO 91/15243, WO 93/05818, WO 96/23524, WO 95/26205 and WO 96/17628; EP-A-554213; and GB 9624918.0; metal radionuclides, paramagnetic metal ions, fluorescent metal ions, heavy metal ions and cluster ions as described in PCT Publication No. WO 91/14460, WO 89/00557, WO 92/17215, WO 96/40287 and WO 96/22914; and U.S. Pat. Nos. 4,647,447, 5,367,080 and 5,364,613; non-metal atomic moieties such as e.g., $^{123}$I, $^{131}$I and $^{18}$F, and heavy atoms such as I; organic chromophoric or fluorophoric moieties as described in Matsuoka, Topics in Applied Chemistry: Infrared absorbing dyes (1990); Waring et al., Topics in Applied Chemistry: The Chemistry and Application of Dyes (1990); "Handbook of Fluorescent Probes and Research Chemicals" Haugland, Molecular Probes Inc, 1996, DE-A-4445065, DE-A-4326466, JP-A-3/228046, Narayanan et al., *J. Org. Chem.*, 60:2391-2395 (1995), Lipowska et al., *Heterocyclic Comm.*, 1:427-430 (1995), Fabian et al., *Chem. Rev.*, 92:1197 (1992); PCT Publication No. WO96/23525: Strekowska et al., *J. Org. Chem.*, 57:4578-4580 (1992); and PCT Publication No. WO 96/17628; visible dyes as described in, Waring and Hallas, The Chemistry and Application of Dyes, Topics in Applied Chemistry (1990); Haugland, Handbook of Fluorescent Probes and Research Chemicals (6th ed. 1996).

Examples of imaging modalities suitable for detecting the detectable moiety linked to the ligand include, but are not limited to, magnetic resonance, nuclear magnetic resonance, radio scintigraphy, positron emission tomography, computed tomography, near-infrared fluorescence, X-ray, ultra sound, ultraviolet light, or visible light, wherein the image of the detectable moiety is indicative of the activity of a specific extracellular protease (see, for example, Dahnhert, Radiology Review Manual (4th ed. 1999); Brant et al., Fundamentals of Diagnostic Radiobiology, (2nd ed. 1999); Weissleder et al., Primer of Diagnostic Imaging, (2nd ed. 1997); Buddinger et al., Medical Magnetic Resonance A Primer, Society of Magnetic Resonance, Inc. (1988); and Weissleder et al., *Nature Biotech.*, 17:375-378 (1999)).

In certain circumstances, it may be desirable that the linker biodegrade after administration. By selecting an appropriately biodegradable linker, it is possible to modify the biodistribution and bioelimination patterns for the polypeptide and/or detectable moiety. Where polypeptide and/or detectable moiety are biologically active or are capable of exerting undesired effects if retained after the imaging procedure is over, it may be desirable to design biodegradability into the linker that ensures appropriate bioelimination or metabolic breakdown of the polypeptide and/or detectable moieties. Thus, a linker may contain a biodegradable function that on breakdown yields breakdown products with modified biodistribution patterns that result from the release of the detectable moiety from the polypeptide or from fragmentation of a macromolecular structure. By way of example, for linkers that carry chelated metal ion moieties, it is possible to have the linker incorporate a biodegradable function that on breakdown releases an excretable chelate compound containing the detectable moiety. Accordingly, biodegradable functions may, if desired, be incorporated within the linker structure, preferably at sites which are (a) branching sites, (b) at or near attachment sites for ligands or detectable moieties, or (c) such that biodegradation yields physiologically tolerable or rapidly excretable fragments.

XI. Kits

In another aspect, the present invention provides kits for the treatment, i.e., amelioration, or prevention of a disease or disorder, i.e., condition, associated with dyslipidemia, hypercholesterolemia and inflammation. In a preferred embodiment, the present invention provides kits for the treatment, i.e., amelioration, of one or more symptoms of atherosclerosis or for the prophylactic treatment of a subject (e.g., human or animal) at risk for atherosclerosis. The kits preferably comprise a container containing one or more of the polypeptides (or peptidomimetics) of this invention. The polypeptide or peptidomimetic can be provided in a unit dosage formulation (e.g., tablet, caplet, patch, suppository, etc.) and/or can be optionally combined with one or more pharmaceutically acceptable excipients.

The kit can, optionally, further comprise one or more other agents used in the treatment of a disease or condition associated with dyslipidemia, hypercholesterolemia and inflammation (such as heart disease and/or atherosclerosis). Such agents include, but are not limited to, those set forth above in connection with the section on "Combination Therapy." For instance, in certain embodiments, the kit can include beta blockers, vasodilators, aspirin, statins, ace inhibitors or ace receptor inhibitors (ARBs) and the like.

In addition, the kits can optionally include labeling and/or instructional materials providing directions (i.e., protocols) for the practice of the methods or use of the "therapeutics" or "prophylactics" of this invention. Preferred instructional materials describe the use of one or more polypeptides or peptidomimetics of this invention, for example, to mitigate one or more symptoms of atherosclerosis and/or to prevent the onset or increase of one or more of such symptoms in an individual at risk for atherosclerosis. The instructional materials can also, optionally, teach preferred dosages/therapeutic regiment, counter indications and the like.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips, etc.), optical media (e.g., CD ROM), and the like. Such media may include addresses to internet sites that provide such instructional materials.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

XII. EXAMPLES

Example 1

Cholesterol Efflux Activity of the Polypeptide of SEQ ID NO:4

The polypeptides of the present invention were synthesized using standard techniques and purified by high performance liquid chromatography. Polypeptides composed of all naturally occurring L-amino acids were used to carry out all of the following examples, unless otherwise indicated.

To establish characteristics related to the biological activity of the polypeptide of SEQ ID NO:4, cholesterol efflux experiments were conducted with ABCA1-expressing macrophages. J774 mouse macrophages labeled with [$^3$H]cholesterol were treated (20 h) with 22-hydroxycholesterol (10 μM)/cis-retinoic acid (10 μM) to upregulate cellular ABCA1 protein. The upregulated cells were washed and then exposed to increasing concentrations of the polypeptide of SEQ ID NO:4 added to the culture medium (no serum) in lipid-free form. The polypeptide stimulated cholesterol efflux in a concentration-dependent manner, promoting maximal-levels of efflux at 3 μg/ml (see, FIG. 1). Cholesterol efflux saturated over a narrow concentration-range (0.1 to 3 μg/ml) and a sigmoidal-shaped efflux curve was obtained, reflecting a high affinity and cooperative process involving ABCA1.

Example 2

Figure 2:
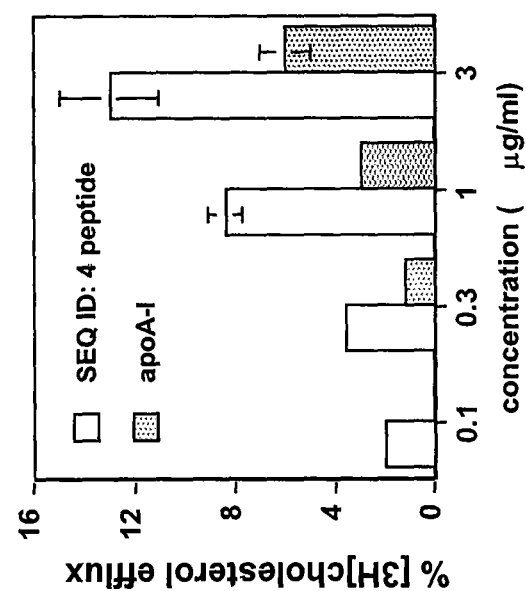
FIG. 2 illustrates that the polypeptide of SEQ ID NO:4 stimulated relatively high-levels of cholesterol efflux at mass concentrations where apoA-I was largely ineffective.

Cholesterol Efflux Activity of the Polypeptide of SEQ ID NO:4 Compared to ApoA-I Experiments were conducted to determine the relative potency of the polypeptide of SEQ ID NO:4 and the magnitude of its cholesterol efflux response compared to full-length apoA-I. Mouse macrophages labeled with [$^3$H]cholesterol were treated to upregulate ABCA1 as described in Example 1. The labeled macrophages were subsequently exposed to increasing concentrations of the polypeptide of SEQ ID NO:4 and ApoA-I based on mass. The polypeptide stimulated relatively high-levels of cholesterol efflux at concentrations where Apo A-I was largely ineffective (see, FIG. 2). Over its working concentration range, the polypeptide of SEQ ID NO:4 was at least 300% more potent than ApoA-I in stimulating cholesterol efflux from ABCA1 expressing macrophages.

Example 3

High-Affinity Efflux Activity of the Polypeptides of SEQ ID NOS:4-6

The affinity of the polypeptides of SEQ ID NOS:4, 5 and 6 for ABCA1 was evaluated by determining the Km values for activity in promoting cellular cholesterol efflux. Mouse macrophages were labeled with [$^3$H]cholesterol and treated with a cAMP analog to induce ABCA1 expression. Cholesterol efflux experiments (4 h) were performed with the labeled cells and by increasing the concentration of the polypeptides of SEQ ID NOS:4-6 and full-length apoA-I and apoE3 in the extracellular medium. Km values were calculated using the Michaelis-Menton equation and GraphPad Prism4 software. The Km values for the peptides were considerably lower (4-5 fold) than intact apolipoproteins when expressed on a mass basis (i.e., μg/ml), reflecting high-levels of cholesterol efflux at relatively low concentrations of the polypeptides of SEQ ID NOS:4-6 (see, FIG. 3). The exemplarily action of these polypeptides was reflected by the Km values expressed in molar units. The polypeptides of SEQ ID NOS:4-6 stimulated cholesterol efflux from ABCA1-expressing macrophages with high-efficiency with activity similar to full-length Apo A-I, Apo E, and the C-terminal (CT) domain of Apo E on per molecule basis.

Example 4

ABCA1 Directed Activity of the Polypeptides of SEQ ID NOS: 4 and 5

Figure 4:
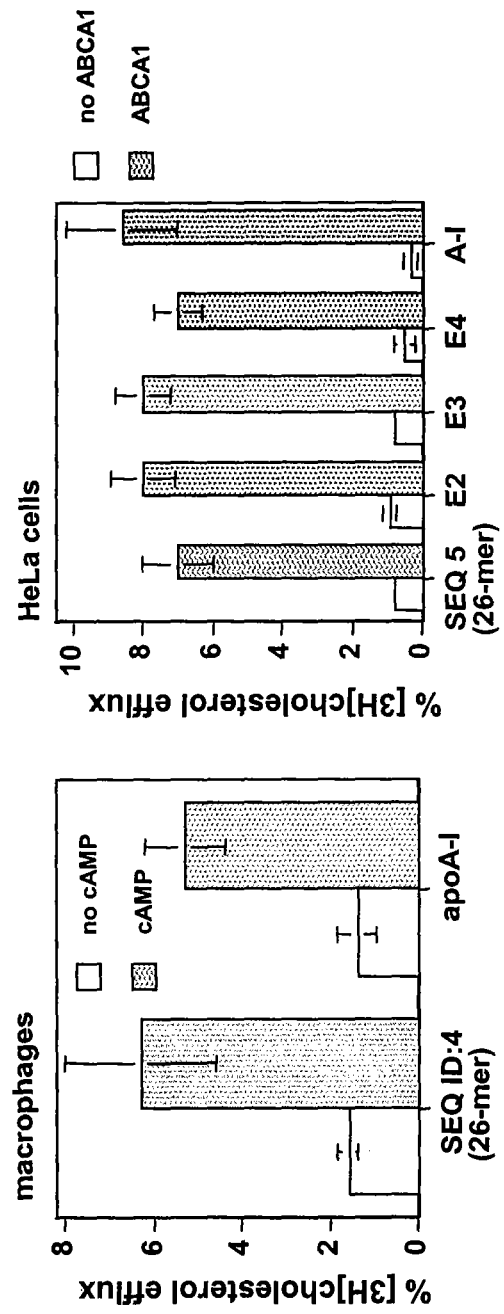
FIG. 4 illustrates that the polypeptide of SEQ ID NO:4 and SEQ ID NO. 5 required ABCA1 for efflux activity, as does apolipoprotein E2, E3, E4 and A-I. The requirement for ABCA1 indicates that non-specific activity in the absence of ABCA1 was minimal and similar to the native apolipoproteins. These results are consistent with the other findings that demonstrate that the polypeptides of the present invention are high-affinity ligands for ABCA1.

To verify that the peptides of the present invention, as exemplified by the polypeptides of SEQ ID NO:4 and SEQ ID NO:5, displayed activity directed toward ABCA1, mouse macrophages (see, left panel of FIG. 4) and HeLa cells transfected with ABCA1 cDNA (see, right panel of FIG. 4) were used in cholesterol efflux experiments. The ability of the polypeptides of SEQ ID NOS:4-6 to stimulate cholesterol efflux (8 hours) in the absence and presence of ABCA1 was evaluated, using relatively high, saturating concentrations of peptides that were >30-fold excess relative to the Km values. The large excess of polypeptide was provided to determine the extent (if any) of non-specific efflux, in the absence of ABCA1 induction. Under these conditions, the polypeptides required ABCA1 for activity, as does apolipoproteins E2, E3, E4 and A-I. Furthermore, the non-specific activity in the absence of ABCA1 was minimal and similar to the native, full-length apolipoproteins.

Example 5

Polypeptide of SEQ ID NO:4 Stabilizes Macrophage ABCA1 Protein

Figure 5:
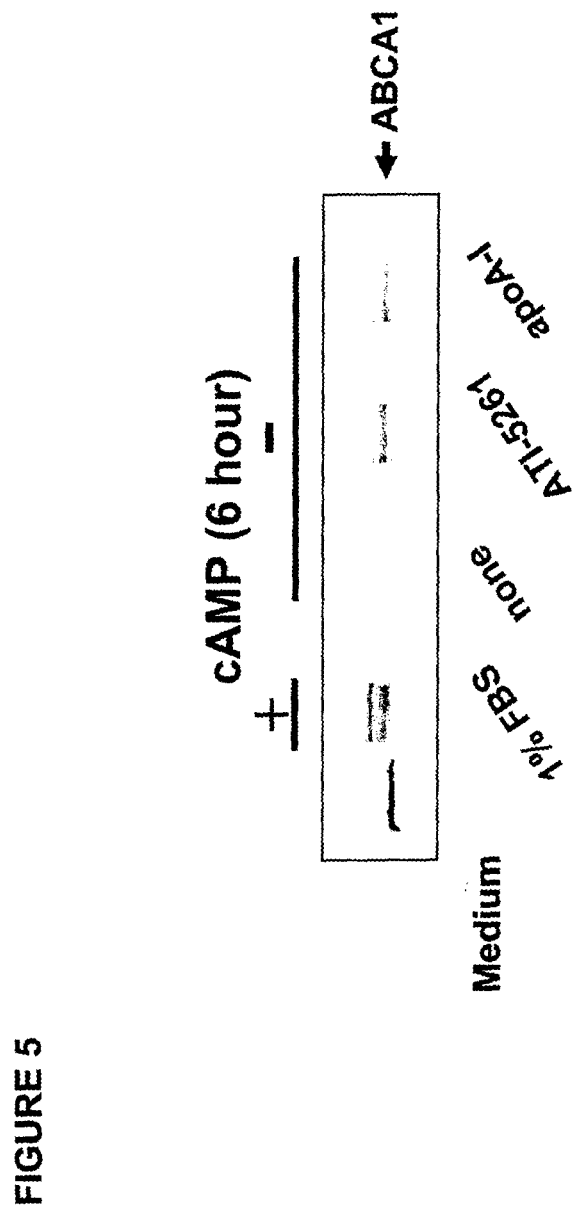
FIG. 5 illustrates that the polypeptide of SEQ ID NO:4 stabilizes macrophage ABCA1 protein. The presence of the polypeptide of SEQ ID NO:4 in the extracellular medium prevented the disappearance of ABCA1 protein similar to Apo A1 and consistent with ABCA1 stabilization activity.

To test whether the polypeptides of the present invention stabilize cellular ABCA1 protein concentrations, J774 mouse macrophages were treated with a cAMP analogue (24 h) to upregulate ABCA1 expression. The cells were subsequently incubated for 6 hours in serum-free medium (no cAMP stimulus) with and without the polypeptide of SEQ ID NO:4. ABCA1 protein in cell lysates was determined by Western blot analysis. Incubation with serum-free medium alone produced a marked decrease in ABCA1 protein, compared to baseline levels in macrophages continuously exposed to cAMP in 1% fetal bovine serum. The presence of the polypeptide of SEQ ID NO:4 in the extracellular medium prevented the disappearance of ABCA1 protein similar to Apo A-I, consistent with ABCA1 stabilization activity and unlike incubations with serum-free medium alone (see, FIG. 5).

Example 6

Figure 6:
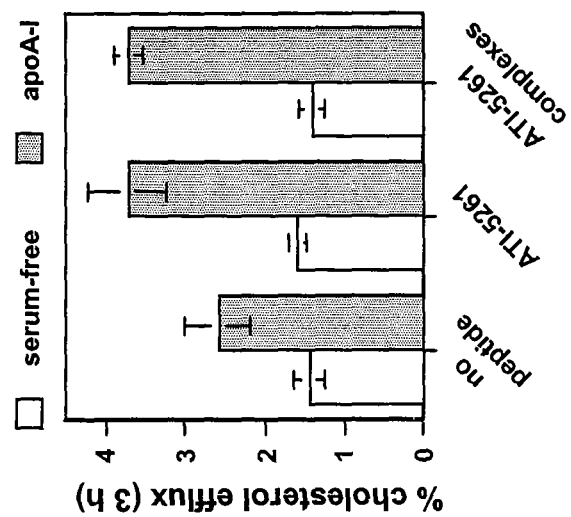
FIG. 6 illustrates that pretreatment of macrophages with the polypeptide of SEQ ID NO:4 enhances cholesterol efflux to Apo A-I. Pretreatment with polypeptide of SEQ ID NO:4 produced a 40% increase in Apo A-I-mediated cholesterol efflux from macrophages, compared to pretreatment with serum-free medium alone. Similar results were seen with complexes of the polypeptide of SEQ ID NO:4 and POPC.

Polypeptide of SEQ ID NO:4 Pretreatment of Macrophages Enhances Cholesterol Efflux to Apo A-I To determine whether conditioning of macrophages with the polypeptide of SEQ ID NO:4 upregulates cholesterol efflux to native apolipoproteins, J774 macrophages labeled with [$^3$H]cholesterol were induced for the ABCA1 response using a cAMP analog (24 h). This was followed by a 4 hour treatment (no cAMP) with serum-free medium alone or medium containing the polypeptide of SEQ ID NO:4. After 4 h with no cAMP, cholesterol efflux was initiated by adding fresh medium containing Apo A-I (10 μg/ml). Polypeptide of SEQ ID NO:4 pretreatment produced a 40% increase in Apo A-I-mediated cholesterol efflux from macrophages, compared to pretreatment with serum-free medium alone (see, FIG. 6). A similar increase in Apo A-I-mediated cholesterol efflux was obtained when macrophages were pre-exposed to Polypeptide SEQ ID NO:4:POPC complexes.

Example 7

Cholesterol Efflux Activity of the Polypeptides of the Present Invention

Figure 7:
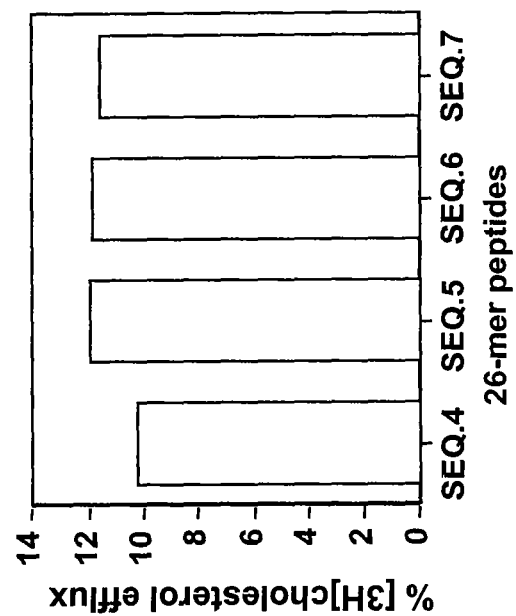
FIG. 7 illustrates that when added to [³H]cholesterol-labeled mouse macrophages in lipid-free form at a concentration of 3 µg/ml, the polypeptide of the present invention stimulated high-levels of cellular cholesterol efflux.

Additional experiments were conducted to determine if the polypeptides of the present invention each displayed high capacity to stimulate cholesterol efflux from ABCA1-expressing macrophages. When added to [$^3$H]cholesterol-labeled mouse macrophages in lipid-free form at a concentration of 3 μg/ml, the polypeptides of SEQ ID NOS:4-7 stimulated high-levels of cellular cholesterol efflux (see, FIG. 7). Thus, each of the exemplary polypeptides of the present invention with conservative substitutions of hydrophobic amino acids displayed the same capacity to stimulate cholesterol efflux.

Example 8

Cholesterol Efflux Activity of Truncated Polypeptides

Figure 8:
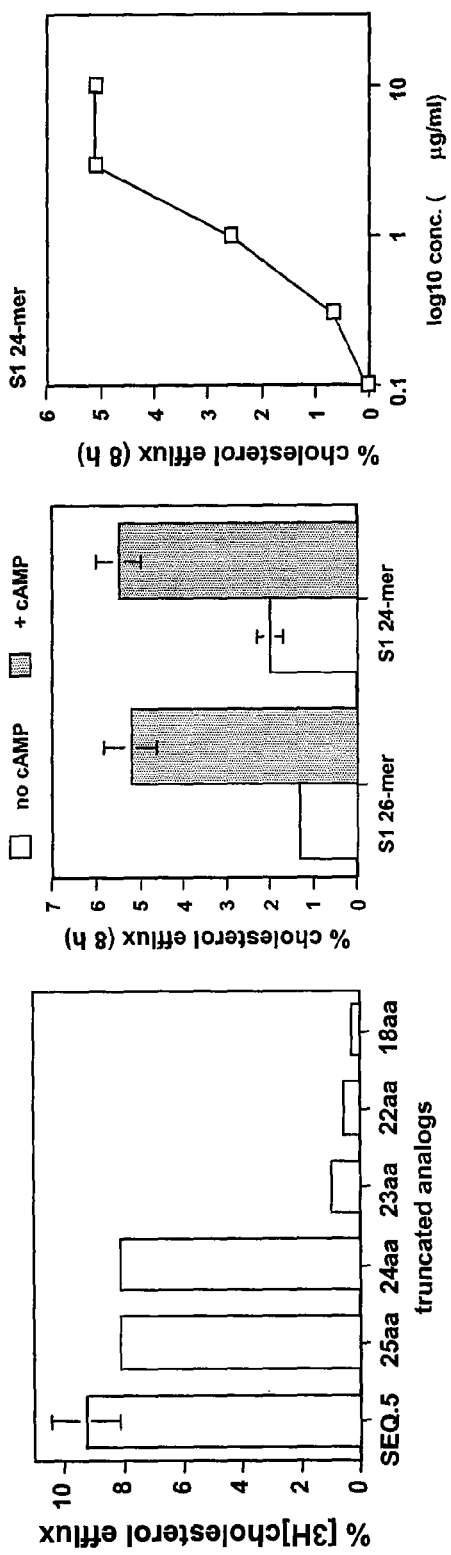
FIG. 8 illustrates that the 25- and 24-mer polypeptides lacking the C-terminal Ser26 and Lys25-Ser26, respectively, retained high activity and stimulated cholesterol efflux efficiently, like the 26-mer polypeptide (SEQ ID NO. 5), demonstrating that the last two amino acids (i.e., Lys25 and Ser26) of the polypeptides of the present invention are not essential for activity. In contrast, deletion of three or more residues from the C-terminal end produced polypeptides (23-, 22- and 18-mers) that were weakly active in stimulating cholesterol efflux.

To evaluate the impact of amino acid deletion, individual amino acids were sequentially removed from the C-terminal end of the polypeptide of SEQ ID NO:5. Mouse macrophages labeled with [$^3$H]cholesterol were treated to upregulate ABCA1 protein as described in Example 1. The ABCA1 expressing macrophages were exposed to 3 μg/ml of the lipid-free polypeptide of SEQ ID NO:5 and its truncated forms. The 25- and 24-mer polypeptides lacking the C-terminal Ser26 and Lys25-Ser26, respectively, retained high capacity to stimulate cholesterol efflux like the 26-mer polypeptide of SEQ ID NO:5 (see, FIG. 8). In contrast, deletion of three or more residues from the C-terminal end (23-, 22- and 18-mers) produced polypeptides that were weakly active. The 24-mer polypeptide of SEQ ID NO:5 stimulated cholesterol efflux in an ABCA1-dependent manner (middle panel), and with high efficiency (right panel) reaching maximal levels of efflux from ABCA1 expressing macrophages at 3 μg/ml.

Therefore, amino acid residues 1-24 constitute a core sequence that is able to support biological activity.

Example 9

Figure 9:
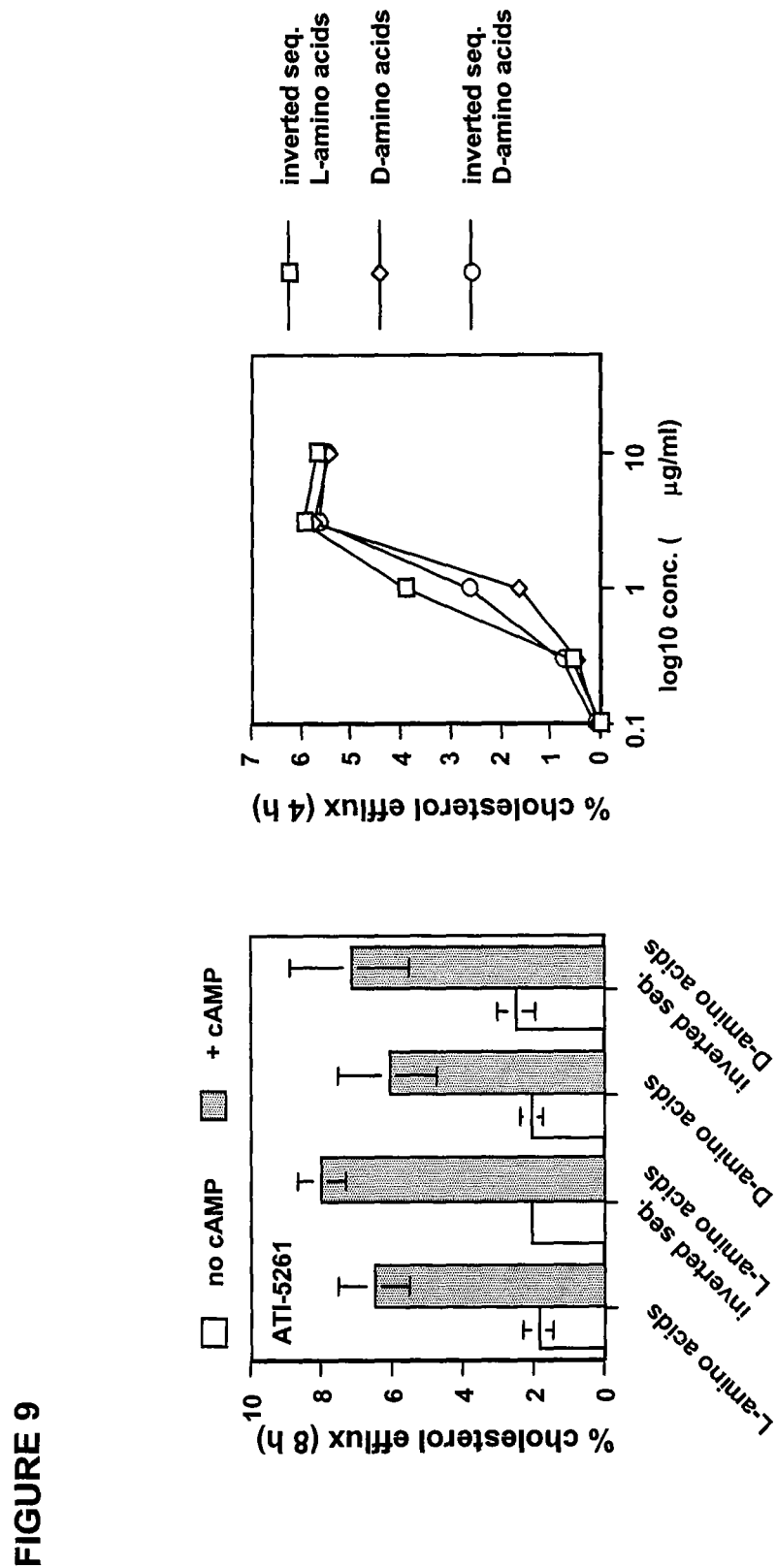
FIG. 9 illustrates that retro-inverted and D-amino acid analogs of the polypeptide of SEQ ID NO:4 stimulate ABCA1 cholesterol efflux in a ABCA1-dependent manner. Maximum levels of cholesterol efflux were achieved at concentrations of 3 µg/ml with these polypeptide analogs.

Retro-Inverted and D-Amino Acid Analogs of the Polypeptide of SEQ ID NO:4 Stimulate ABCA1 Cholesterol Efflux Inverted sequence peptides synthesized with all L-amino acids and all D-amino acids were tested for cholesterol efflux activity using ABCA1 expressing J774 macrophages. The sequence of the inverted peptides was as follows: SKLRAL-FEEAFERFAAFWEELKSRVE (SEQ ID NO:20), which is the amino acid of SEQ ID NO:4 (i.e., ATI-5261) in reverse order. For comparative purposes, the polypeptide of SEQ ID NO:4 was synthesized with all D-amino acids and tested for cholesterol efflux activity. At relatively high extracellular concentrations (30 µg/ml), the inverted sequence peptides (L- and D-amino acid forms) stimulated cholesterol efflux in an ABCA1-dependent manner (see, FIG. 9). Similarly, the polypeptide of SEQ ID NO:4 composed of all D-amino acids promoted ABCA1 cholesterol efflux like the polypeptide of SEQ ID NO:4 composed of all L-amino acids. Moreover, the L- and D-amino acid analogs of the polypeptide of SEQ ID NO:4 stimulated cholesterol efflux efficiently, reaching maximal levels of efflux at 3 µg/ml.

Example 10

Aspartic Acid Residues can Substitute for Glutamate without Loss of Activity

Figure 10:
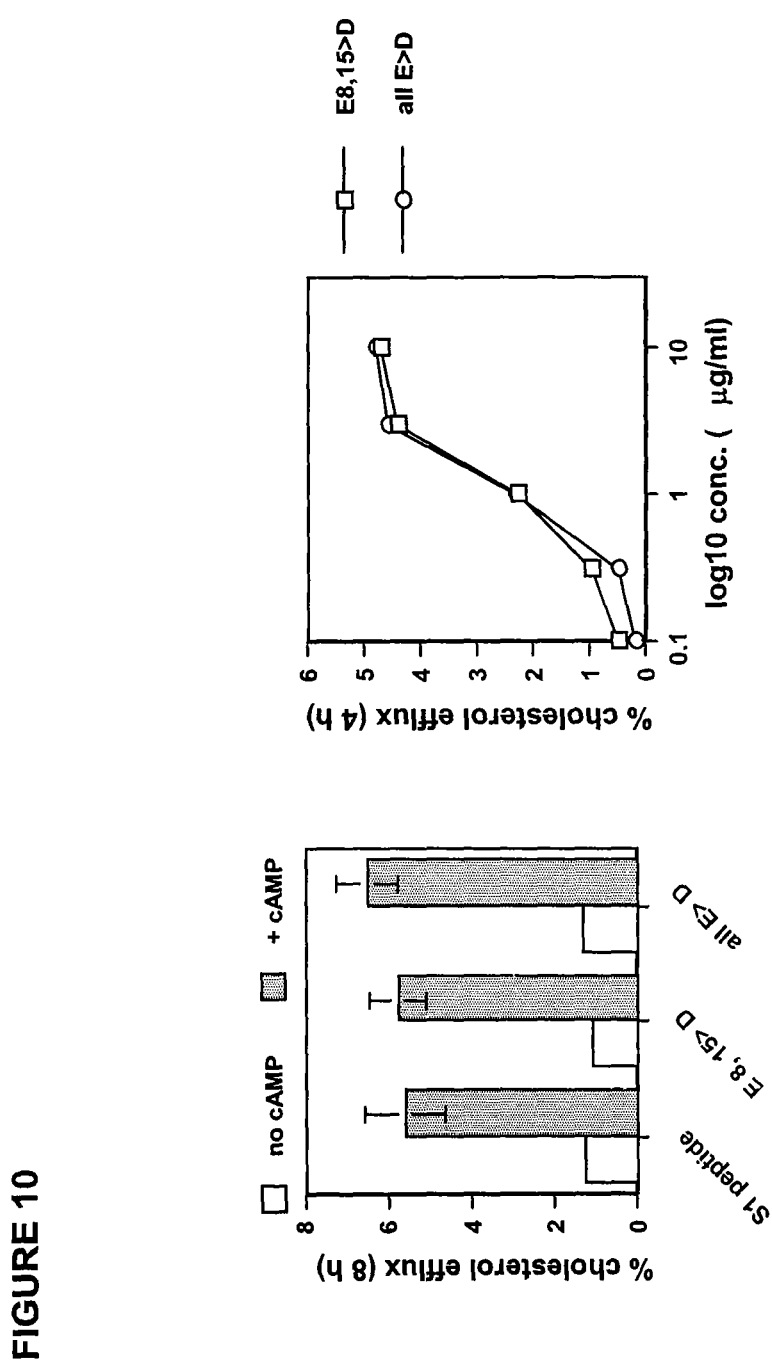
FIG. 10 illustrates that polypeptide analogs of the polypeptide of SEQ ID NO:5, wherein the glutamic acid residues were replaced with aspartic acid residues (i.e., E8, 15>D and E1, 7, 8, 15, 18, 19>D, retained high capacity to stimulate cholesterol efflux in an ABCA1-dependent manner, similar to the polypeptide of SEQ ID NO:5 ("S1"). Maximum levels of cholesterol efflux were achieved at concentrations of 3 µg/ml with these polypeptide analogs of SEQ ID NO:5.

Experiments were conducted using the polypeptide of SEQ ID NO:5 to determine whether conservative amino acid substitutions involving acidic amino acids could support ABCA1 cholesterol efflux activity. Two peptide analogs were engineered; the first replacing glutamic acid residues (E) at position 8 and 15 with aspartic acid residues (D), i.e., E8, 15>D polypeptides, and the second, replacing E1, 7, 8, 15, 18, 19 with D, i.e., all D (Asp) polypeptide. Cholesterol efflux activity was determined using J774 macrophages treated with and without a cAMP analog to modulate ABCA1 expression. Both polypeptide mutants with aspartic acid substitutions retained high capacity to stimulate cholesterol efflux in an ABCA1-dependent manner, similar to the polypeptide of SEQ ID NO:5 (i.e., the S1 polypeptide) (see, FIG. 10). Maximal levels of cholesterol efflux were achieved at concentrations of 3 µg/ml using the aspartic acid polypeptides and cAMP treated macrophages, indicating the polypeptide analogs with conservative acidic residue substitutions stimulated ABCA1 cholesterol efflux efficiently.

Example 11

Importance of Acidic Residues in the Polypeptides of the Present Invention

Figure 11:
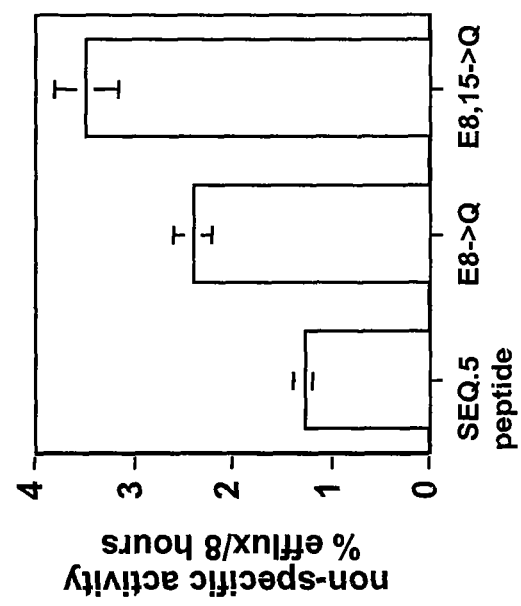
FIG. 11 illustrates that the ABCA1-mediated cholesterol efflux activity of the polypeptides of the present invention is dependent, in part, on the number of acidic residues in the polypeptide.

To test if acidic amino acids were necessary for conferring ABCA1 cholesterol efflux activity, the polypeptide of SEQ ID NO:5 was used to create site-specific mutants. The ABCA1 efflux activity was found to be dependent on the number of acidic residues in the polypeptide of SEQ ID NO:5. Substitution of a single glutamate residue (E) with a glutamine residue (Q), which is not charged, increased the non-specific activity of the polypeptide of SEQ ID NO:5 as judged by an increase in cholesterol efflux in the absence of ABCA1 up-regulation in macrophages (see, FIG. 11). The increase in non-specific efflux was further augmented when two acidic glutamate residues in the polypeptide of SEQ ID NO:5 were replaced with glutamine residures (E8, 15→Q8, 15). These data indicate that the specificity for ABCA1 correlates with the number of acidic residues, such as glutamate residues (or aspartate residues), in the polypeptide.

Example 12

Figure 12:
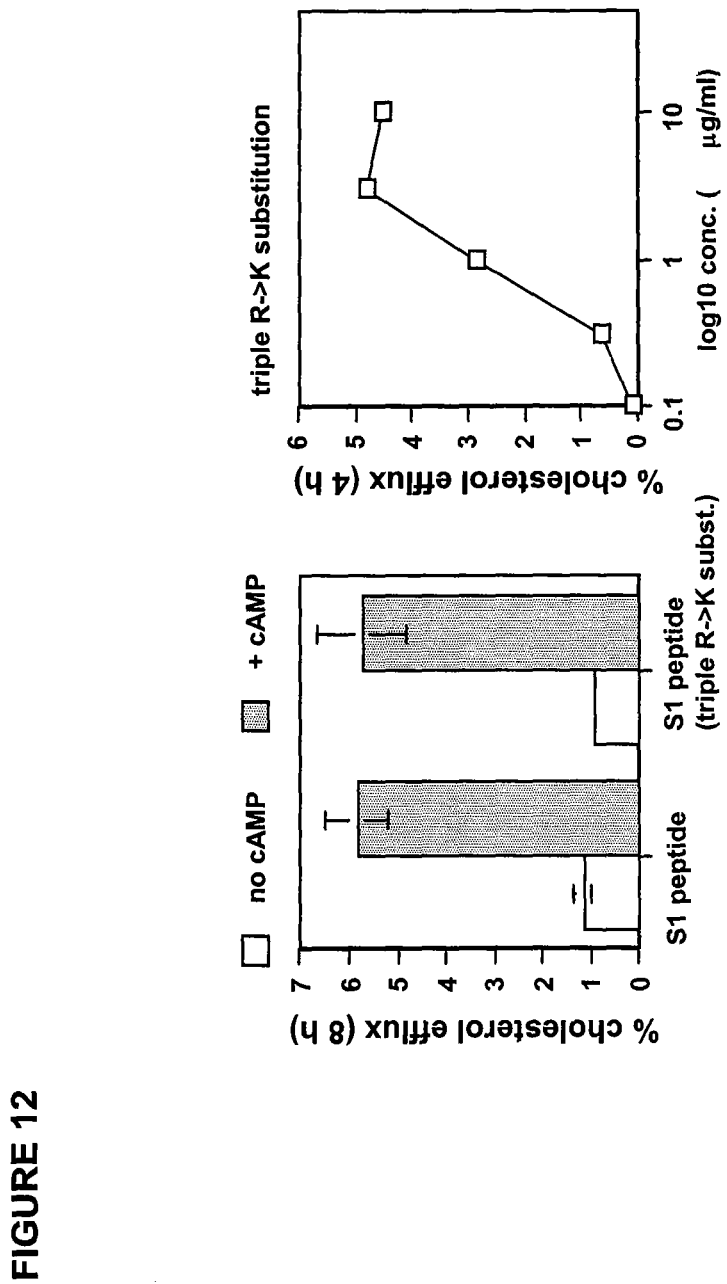
FIG. 12 illustrates that lysine residues can substitute for arginine in the polypeptides of the present invention without loss of activity. The analogs of the polypeptide of SEQ ID NO.:5 having the triple R3, 14, 23>K3, 14, 23 substitutions stimulated ABCA1 cholesterol efflux from macrophages treated with cAMP, similar to the parent polypeptide of SEQ ID NO:5.

Lysine Residues can Substitute for Arginine in the Polypeptides of the Present Invention without Loss of Activity To test whether conservative amino acid substitutions involving positively charged residues impacted cholesterol efflux activity, the polypeptides of the present invention, as exemplified by the polypeptide of SEQ ID NO:5, were synthesized with lysine (K) residues in place of arginine (R) at positions 3, 14 and 23. The analog of the polypeptide of SEQ ID NO:5 possessing the triple R3, 14, 23→K3, 14, 23 substitutions stimulated ABCA1 cholesterol efflux from macrophages treated with cAMP, similar to the parent polypeptide of SEQ ID NO:5 (see, FIG. 12). Low efflux was observed with both polypeptides using cells not induced for the ABCA1 response (i.e., no cAMP). The lysine substitution polypeptide also stimulated ABCA1 cholesterol efflux efficiently, reaching maximal levels of efflux at 3 µg/ml of polypeptide.

Example 13

Importance of Cationic Residues for ABCA1 Cholesterol Efflux Activity

Figure 13:
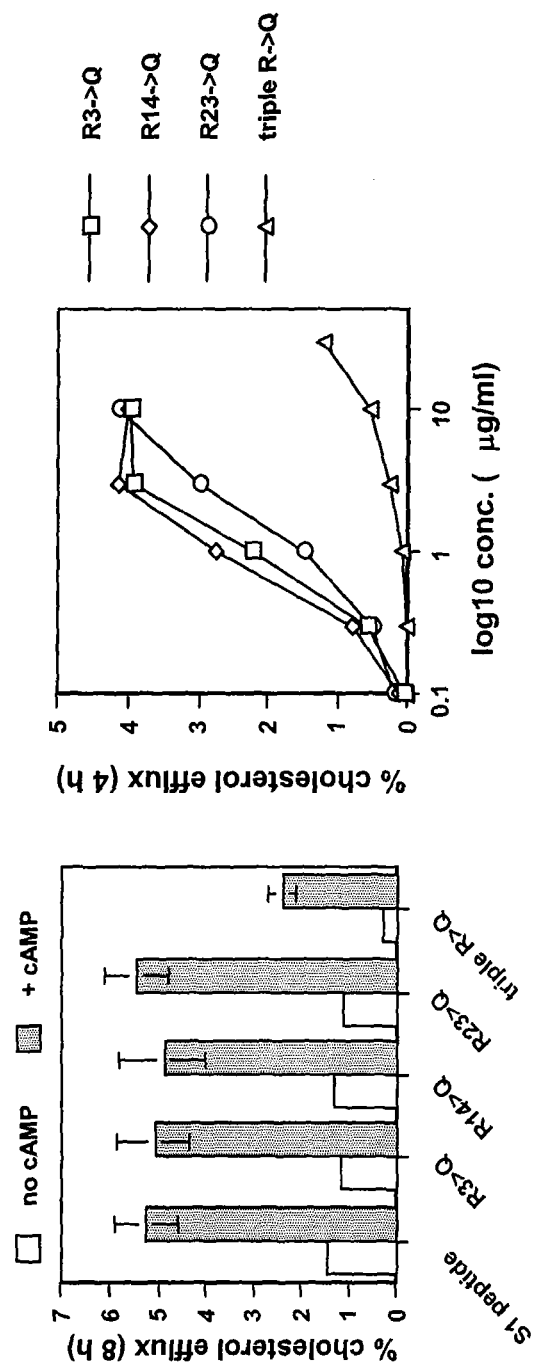
FIG. 13 illustrates the importance of cationic residues for ABCA1 cholesterol efflux activity. Analogs of the polypeptide of SEQ ID NO:5 having arginine (R) to glutamine (Q) substitutions, i.e., R3→Q, R14→Q and R23→Q, all mediated cholesterol efflux in an ABCA1 dependent manner, similar to the parent polypeptide of SEQ ID NO:5, when used at a concentration of 30 µg/ml. In contrast, when these three arginine residues (R) were replaced with glutamine (Q), the resulting polypeptide had greatly reduced efflux capacity and reduced efflux efficiency.

The polypeptide of SEQ ID NO:5 was engineered with arginine (R) to glutamine (Q) substitutions, to determine if positively charged residues were necessary for mediating ABCA1 cholesterol efflux. Single R→Q substitutions were made at positions 3, 14, and 23 in the linear sequence of the polypeptide of SEQ ID NO:5, thereby replacing a positively charged amino acid with an uncharged, polar amino acid. The single R→Q substitution polypeptides, R3→Q, R14→Q and R23→Q, all mediated cholesterol efflux in an ABCA1 dependent manner, similar to the parent polypeptide of SEQ ID NO:5, when used at a concentration of 30 µg/ml (see, FIG. 13). Moreover, the polypeptides with the single glutamine substitution stimulated ABCA1 cholesterol efflux with high efficiency, as judged by the concentration dependence curves. In contrast, when multiple arginine residues were simultaneously changed to glutamine within the polypeptide of SEQ ID NO:5, i.e., triple R3, 14, 23→Q3, 14, 23, the polypeptide had greatly reduced efflux capacity and reduced efflux efficiency.

Example 14

Figure 14:
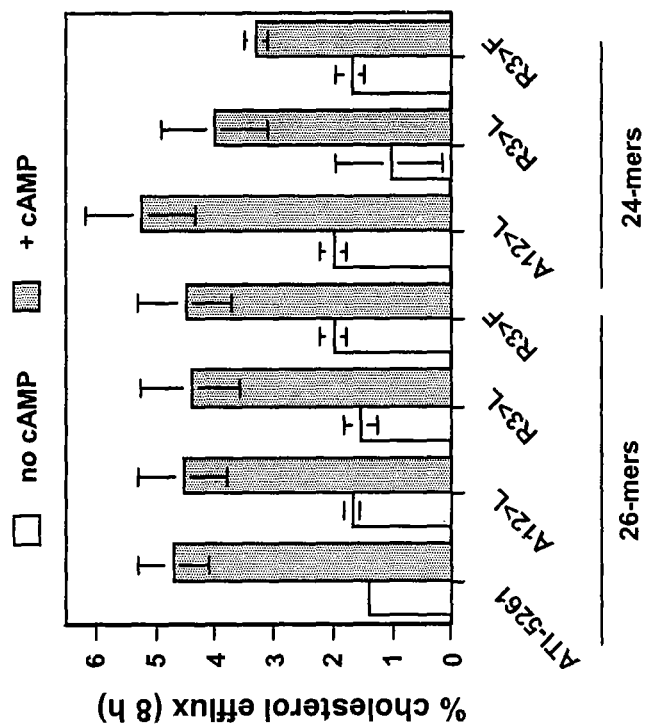
FIG. 14 illustrates that polypeptides of the present invention having hydrophobic amino acid substitutions at the lipid-water interface maintain their ability to stimulate high levels of cholesterol efflux. 26- and 24-mer polypeptides corresponding to the polypeptide of SEQ ID NO:4, wherein the arginine at position 3 was replaced with hydrophobic amino acids, i.e., R3>L and R3>F polypeptides, stimulated relatively high-levels of cholesterol efflux from ABCA1 expressing macrophages (i.e., plus cAMP). Similarly, A12>L polypeptide analogs of SEQ ID NO:4 also stimulated cholesterol efflux from macrophages in an ABCA1-dependent manner.

The Polypeptide of SEQ ID NO:4 Supports Hydrophobic Amino Acid Substitutions at the Lipid-Water Interface 26- and 24-mer polypeptides corresponding to the polypeptide of SEQ ID NO:4 were used to further explore the importance of interfacial positive charges, by replacing arginine at position 3 with hydrophobic amino acids, i.e., R3>L and R3>F polypeptides, thereby expanding the non-polar lipid-binding area of the polypeptide. The impact of the A12>L substitution was also tested for activity, which also expanded non-polar surface area. In keeping with results presented in Example 13, above, the R3 substitution polypeptides stimulated relatively high-levels of cholesterol efflux from ABCA1 expressing macrophages (i.e., plus cAMP); whereas, low-levels of cholesterol efflux were observed from macrophages not induced for the ABCA1 response (no cAMP) (see, FIG. 14). The A12>L substitution analogs of the polypeptide of SEQ ID NO:4, i.e., 26- and 24-mer forms, also stimulated cholesterol efflux from macrophages in an ABCA1-dependent manner.

Example 15

Substitutions of Polar Uncharged Amino Acids Support ABCA1 Efflux Activity

Figure 15:
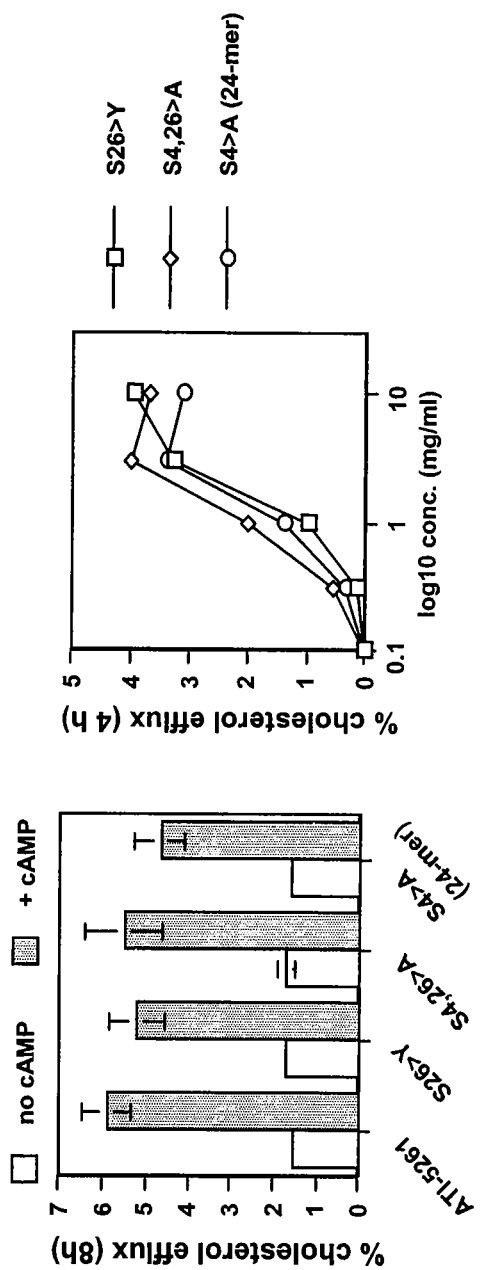
FIG. 15 illustrates that substitutions of polar uncharged amino acids support ABCA1 efflux activity. Polypeptide analogs of the polypeptide of SEQ ID NO:4 having a serine to tyrosine substitution at position 26 (i.e., S26>Y) or serine to alanine substitutions at positions 4 and 26 (S4, 26>A) retained ABCA1-dependent cholesterol efflux activity.

Substitutions involving polar uncharged residues located toward the middle of the polar surface of the polypeptide of SEQ ID NO:4 were tested for retention of ABCA1 cholesterol efflux activity. Replacement of serine with tyrosine (Y) at position 26 created a polypeptide, i.e., S26>Y, that stimulated ABCA1 cholesterol efflux like the parent 26-mer polypeptide of SEQ ID NO:4 (right panel of FIG. 15). In similar fashion, serine to alanine substitutions at positions 4 and 26 produced a polypeptide (S4, 26>A) that retained ABCA1-dependent cholesterol efflux activity. The 24-mer core peptide with the S4>A substitution also retained high capacity to stimulate ABCA1 cholesterol efflux; whereas, low-levels of cholesterol efflux were obtained in the absence of ABCA1 up-regulation (no cAMP). All polypeptides with S>A or S>Y substitutions stimulated cholesterol efflux efficiently from ABCA1 expressing macrophages, reaching maximal levels of efflux at concentrations of 3 µg/ml (left panel of FIG. 15).

Example 16

Figure 16:
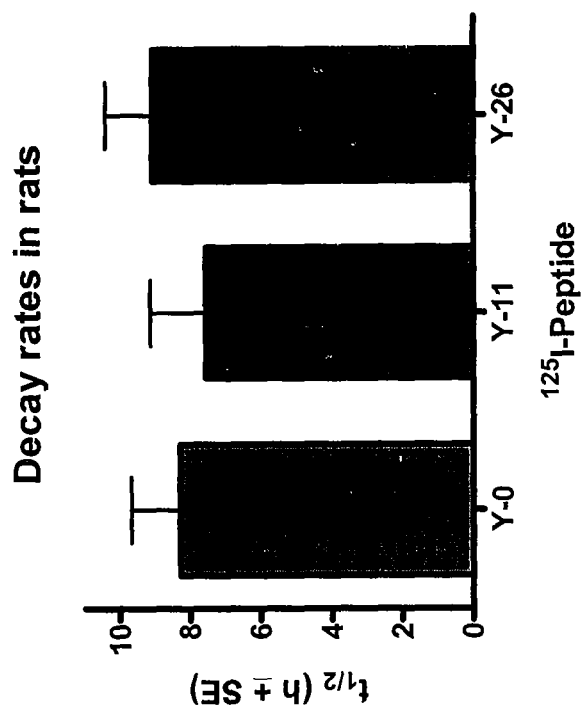
FIG. 16 illustrates that substitutions with non-polar and polar non-charged amino acids support ABCA1 efflux activity. Polypeptide analogs of the polypeptide of SEQ ID NO:4 having a A11>Y11 substitution having identical pharmacokinetic properties to that of the parent polypeptide. The pharmacokinetic analysis depicted here was based on a monophasic model.

Substitutions with Non-Polar and Polar Non-Charged Amino Acids Support ABCA1 Efflux Activity Position 11, i.e., A, in the polypeptide of SEQ ID NO:4 can be substituted with other non-polar (hydrophobic) amino acids as well as other polar non-charged amino acids. For instance, A11>Y11 substitution results in a polypeptide having identical pharmacokinetic properties using a monophasic decay model (see, FIG. 16).

Example 17

Figure 17:
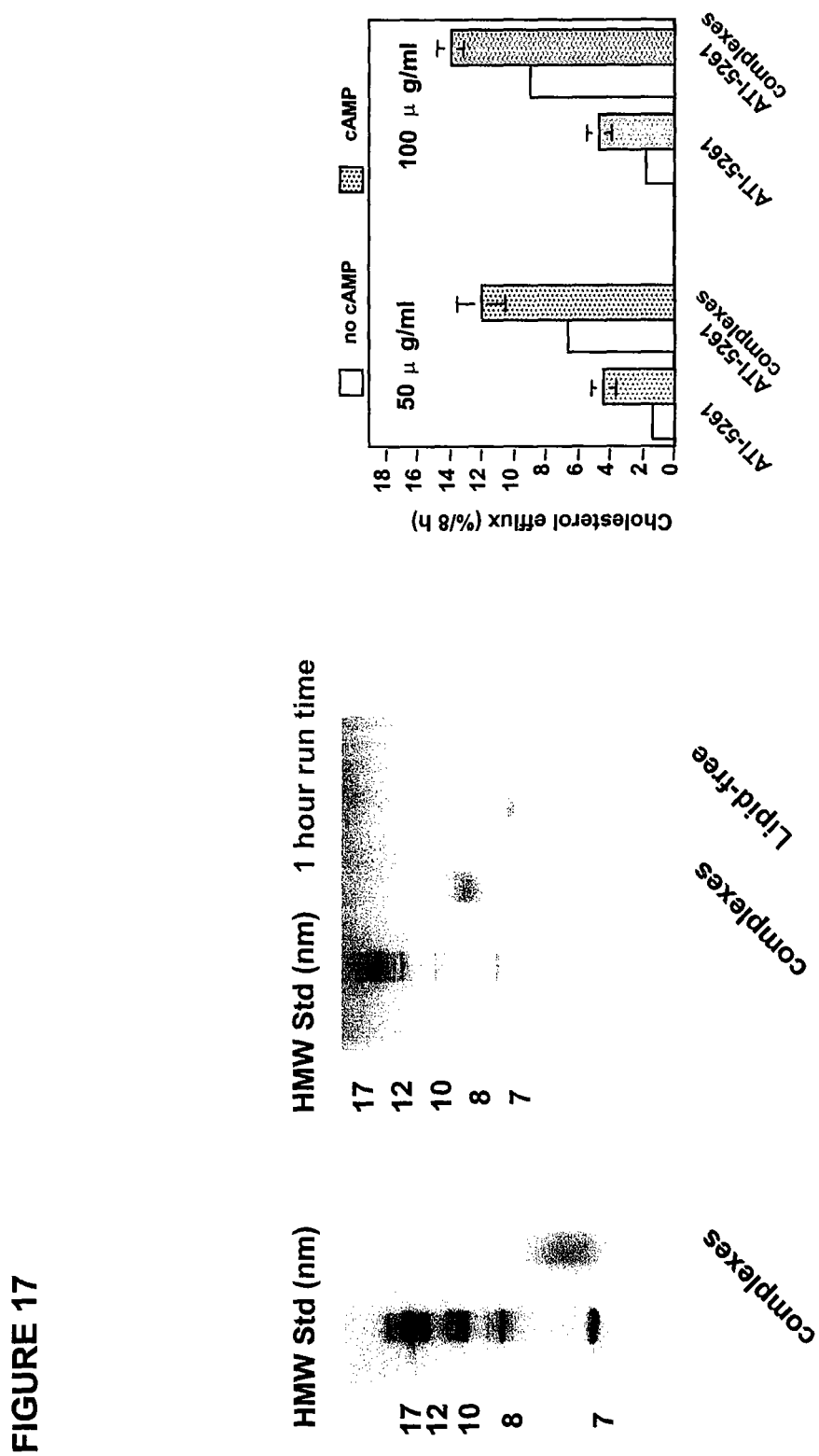
FIG. 17 illustrates that when the polypeptide of SEQ ID NO:4 is formulated with POPC, it stimulated cholesterol efflux from macrophages to a greater extent than the lipid-free polypeptide.

Cholesterol Efflux Activity of Polypeptide-Phospholipid Complexes 1-palmitoyl-2-oleoyl-phosphatidylcholine (POPC) was used to evaluate the cholesterol efflux properties of a formulated polypeptide of the present invention. The polypeptide of SEQ ID NO:4 was combined with POPC to create synthetic particles, using a modified cholate-dialysis procedure. Non-denaturing gradient electrophoresis (4-20% polyacrylamide gels) indicated the polypeptide:POPC complexes were 7-8 nm in size. Under conditions of short run-times, the lipid-free polypeptide migrated as a single band and further into the gel compared to the polypeptide:POPC complexes. These results provide evidence that the preparations of POPC complexes were not contaminated with lipid-free polypeptide. To test cholesterol efflux activity, J774 mouse macrophages were labeled with [$^3$H]cholesterol and treated with and without cAMP to modulate ABCA1 expression. The polypeptide formulated with POPC possessed ~5-fold greater capacity to stimulate cholesterol efflux, compared to the lipid-free polypeptide of SEQ ID NO:5 when used at concentrations of 50 and 100 µg/ml (see, FIG. 17). Interestingly, a component of the efflux response to the polypeptide:POPC complexes was dependent on ABCA1 activity, as greater cholesterol efflux was observed from cAMP-treated macrophages compared to control macrophages (no cAMP).

Example 18

Figure 18:
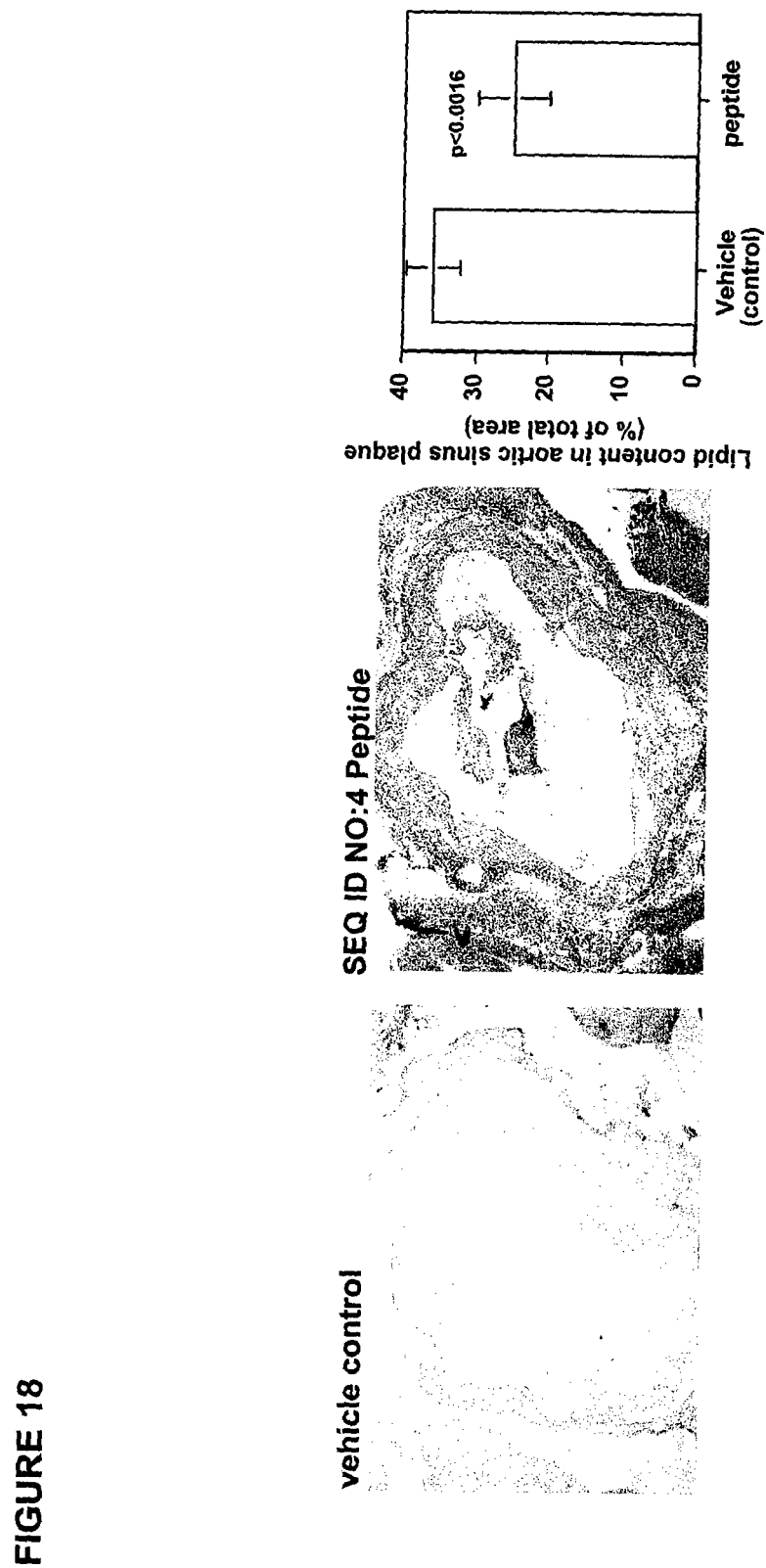
FIG. 18 illustrates that despite the advanced atherosclerosis and the continued presence of the dietary insult during the intervention, the polypeptide SEQ. ID NO. 4 significantly reduced established atherosclerosis compared to vehicle alone, as judged by highly significant reduction in the lipid-content of plaques within the aortic sinus.

In Vivo Effects of the Polypeptide of SEQ ID NO:4 on Established Atherosclerosis Male Apolipoprotein E deficient (Apo E −/−) mice (six-weeks of age) were fed a high-fat diet for 26 weeks. During the last 6 weeks on the high-fat diet, the mice received intraperitoneal (IP) injections of either saline or the polypeptide of SEQ ID NO:4 (10 mg/kg) at 2-day intervals. Mice injected with saline alone (control) possessed 38% greater atherosclerosis compared to mice receiving the polypeptide of SEQ ID NO:4. The effect of the polypeptide reducing established atherosclerosis was highly significant, as judged by the lipid-content of plaques in the aortic sinus (see, FIG. 18). This was accomplished using the lipid-free polypeptide of SEQ ID NO:4 composed of all L-amino acids administered in the continued presence of the dietary insult. Therefore, the polypeptide of SEQ ID NO:4 reduced aortic plaque lipid content in hypercholesterolemic mice that possessed substantial levels of atherosclerosis.

Example 19

The Polypeptides of Present Invention have Significant Atherosclerotic Effects

Figure 19A:
FIGS. 19A and 19B illustrates that the polypeptide of SEQ ID NO:4 and complexes of the polypeptide of SEQ ID NO:4 and POPC have the ability to reduce atherosclerosis in mice. After 6 weeks of treatment, the polypeptide of SEQ ID NO:4 reduced plaque lesion area over the whole aorta and decreased the lipid-content of aortic sinus plaque. Similar reduction in atherosclerosis were observed using complexes of the polypeptide of SEQ ID NO:4 and POPC.
Figure 19B:
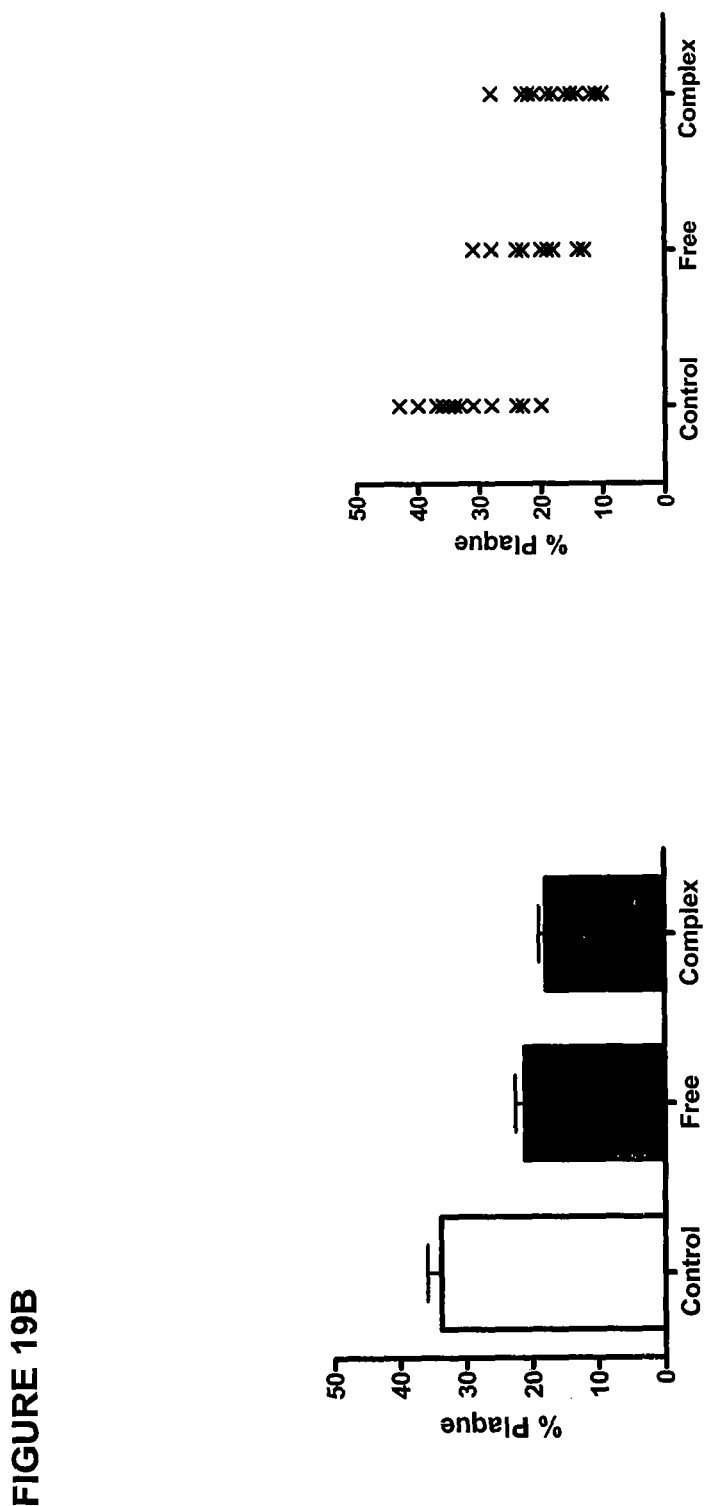

The polypeptide of SEQ ID NO:4 and its Y26 analog have been evaluated with respect to ability to inhibit atherosclerosis in Apolipoprotein E knock-out mice. The mice were given Western diet for 18 weeks and then randomized to receive saline, free polypeptide or polypeptide-phospholipid complex. The 30 mg/kg of body weight dose of polypeptide administered IP, based on the 40% bioavailability, corresponds to 12 mg/kg IV injection and was given every second day for 6 weeks in the first two studies and every day for 3 weeks in the third study. The degree of atherosclerosis was then determined in whole aorta and aortic root/sinus. Three experimental series were performed. The pooled data showed that both free polypeptide and polypeptide-phospholipid complex have significant antiatherosclerotic effects (see, FIGS. 19A and 19B). The results are equal to or better than previously have been obtained with IV infusions of 40 mg/kg Apolipoprotein A-I Milano/phospholipids complex into Apo E knock-out mice (Shah et al., *Circ.*, 97:780-5, 1998).

As noted above, data from three experimental series were pooled. Pooling of data is justified as only minor changes in the procedures were made (21 injections at 30 mg/kg over 42 and 21 days, respectively), and the diet regimens and sources of mice and polypeptide, respectively, were the same. In the first experiment S26 was substituted for Y26.

Example 20

In Vivo Effects of the Polypeptide of SEQ ID NO:4 on Cholesterol Efflux and RCT

Figure 20:
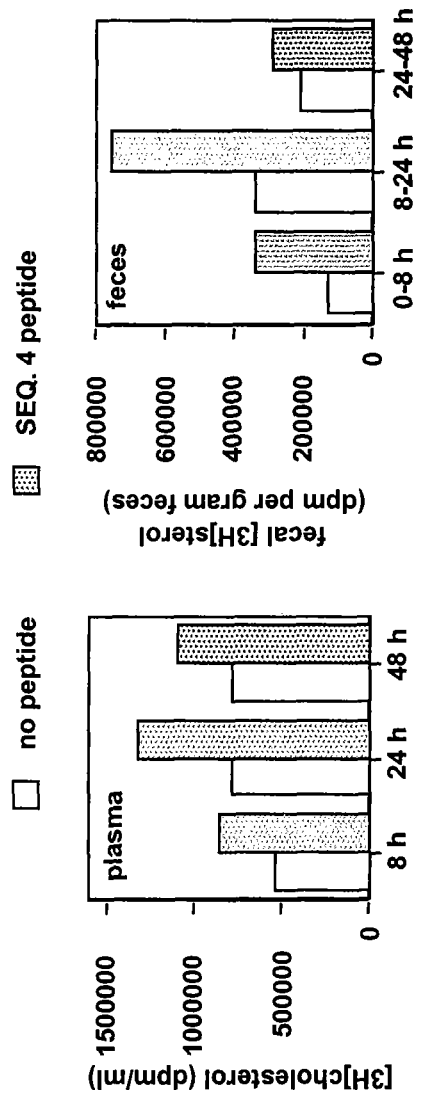
FIG. 20 illustrates that the polypeptide of SEQ ID NO. 4 stimulated cholesterol efflux in vivo, as judged by a pronounced (2-fold) increase in the levels of macrophage derived [$^3$H]cholesterol appearing in plasma at 8 and 24 hour post-injection, compared to saline vehicle alone. This was accompanied by a greater than 2-fold increase in fecal sterol secretion, indicating the polypeptide was highly effective in promoting the transport of FIG. 21 provides summary graphs that illustrate that the polypeptide of SEQ ID NO:4 has significant anti-atherosclerotic effects in preventing the formation of atherosclerotic plaques in LDL receptor knock-out mice. Analysis of the whole aorta by immunostaining showed that the amount of plaque was reduced in animals treated with the free peptide or with the peptide-phospholipid complex in comparison to control animals.
Figure 21:
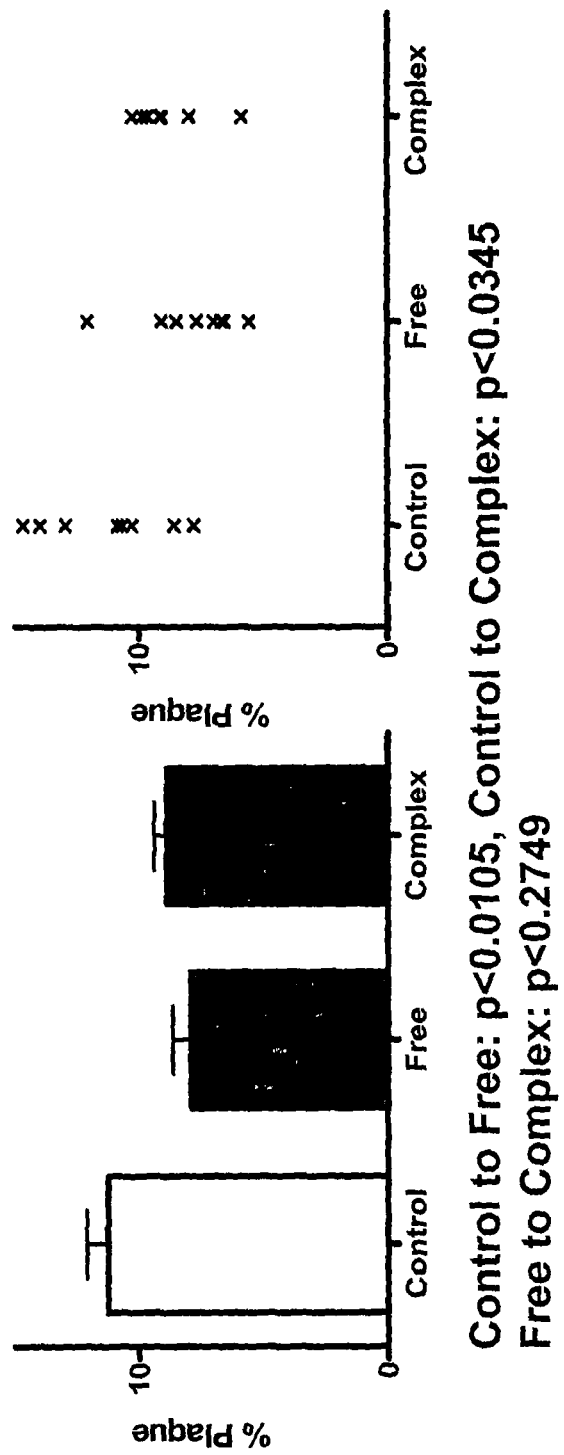

Apolipoprotein E deficient (ApoE −/−) mice at 6 months of age were used to evaluate the ability of the polypeptide of SEQ ID NO:4 to stimulate cholesterol efflux and Reverse Cholesterol Transport (RCT) in vivo. [$^3$H]cholesterol-labeled macrophage foam-cells (i.e., loaded with acetylated LDL) were injected into the intraperitoneal (IP) cavity of Apo E −/− mice in the presence and absence of the polypeptide of SEQ ID NO:4 (20 mg/kg). The polypeptide stimulated cholesterol efflux in vivo, as judged by a pronounced (2-fold) increase in the levels of macrophage derived [$^3$H]cholesterol appearing in plasma at 8 and 24 hour post-injection, compared to saline vehicle alone (see, FIG. 20). This was accompanied by a greater than 2-fold increase in fecal sterol secretion at 8 and 24 h. In general, the effects of the peptide were relatively long-lived persisting up to 48 h.

Example 21

Polypeptide of SEQ ID NO:4 and Polypeptide SEQ ID NO:4:POPC Complexes Reduce Established Atherosclerosis in Mice Beginning at 6 weeks of age, LDLr knockout mice were fed a high-fat western-diet for 26 weeks. After the dietary challenge, mice were switched to standard chow for 6 weeks. During the 6 weeks on chow diet, mice were injected IP every day with either the polypeptide of SEQ ID NO:4 or a polypeptide of SEQ ID NO:4:POPC complexes at a dose of 30 mg/kg. Control mice received IP injections with PBS vehicle alone. The presence of plaque lesions in the whole aorta was then evaluated. The results show that after 6 weeks of treatment, the polypeptide of SEQ ID NO:4 reduced plaque lesion area over the whole aorta. Similar reduction in atherosclerosis was observed in animals that received the polypeptide of SEQ ID NO:4:POPC complexes.

Example 22

The Polypeptides of the Present Invention have Anti-Inflammatory Properties

Figure 22:
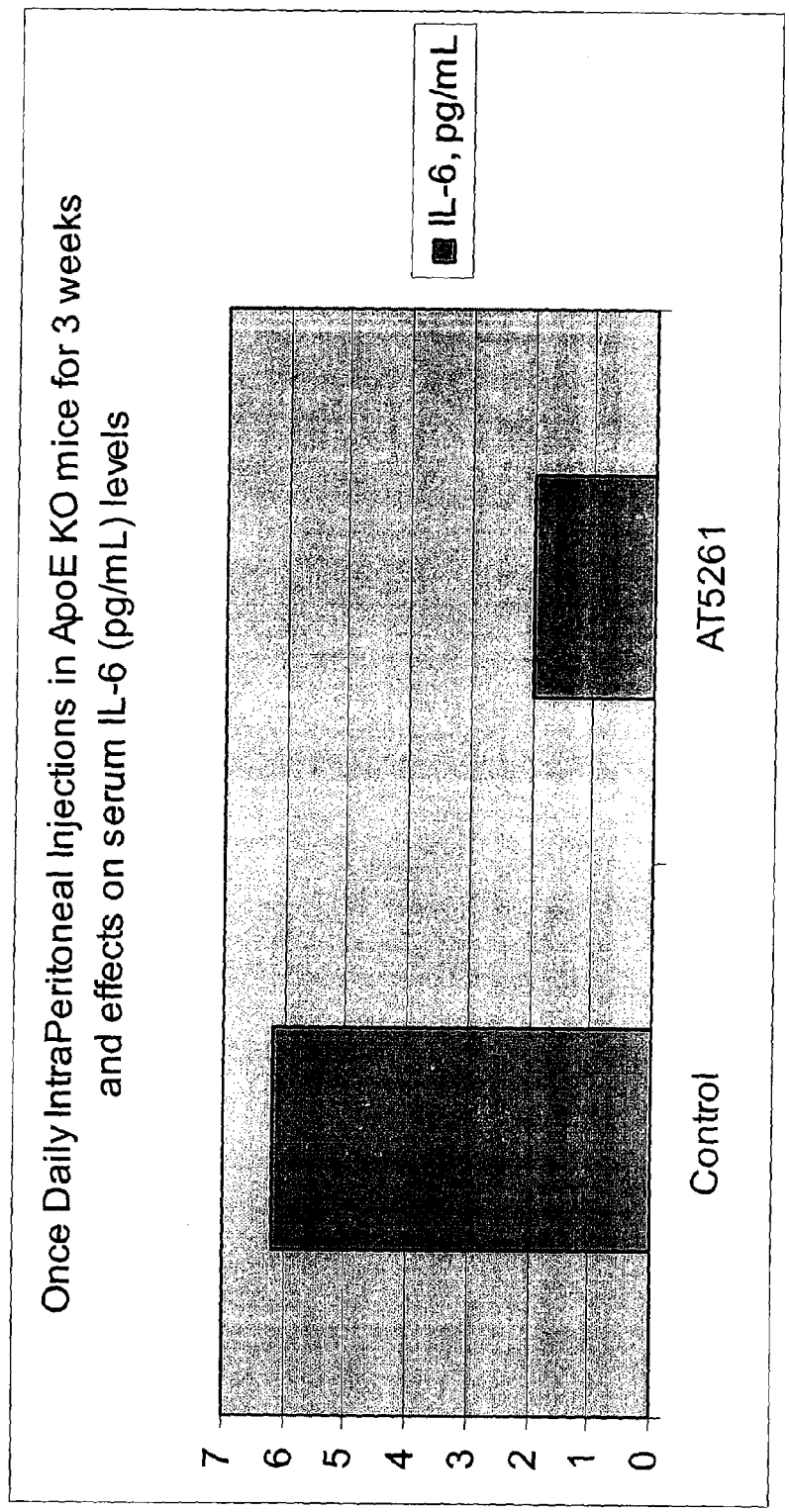
FIG. 22 illustrates that the polypeptide of SEQ ID NO:4 has anti-inflammatory properties. Administration of the polypeptide of SEQ ID NO:4 to apolipoprotein E-deficient rats resulted in lowered levels of the inflammatory cytokine IL-6 in comparison to control animals that received saline.

Apolipoprotein E deficient (ApoE −/−) mice at 6 weeks old were given a Western diets for 18 weeks before commencing treatment. Once daily, intraperitoneal injections were given as saline or the polypeptide of SEQ ID NO:4 (n=6-7 per group). At termination, serum was collected and analyzed for Interleukin-6 concentration by a fluorescent bead immunoassay utilizing flow cytometry (BMS820FF). Mice treated with the polypeptide of SEQ ID NO:4 had about 68% lower serum levels of IL-6 (see, FIG. 22).

Example 23

The Polypeptide of SEQ ID NO:4 has a Long Serum Half-Life

Figure 23:
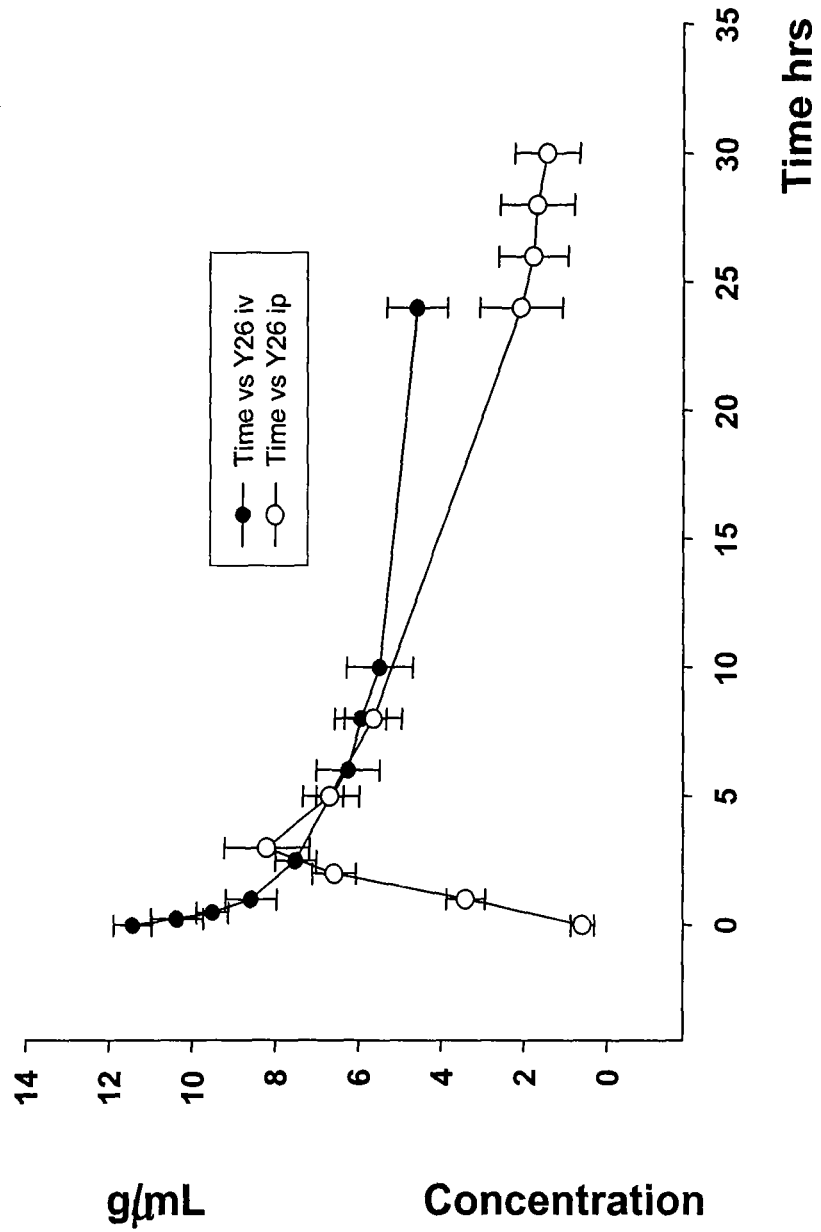
FIG. 23 illustrates that the polypeptide of SEQ ID NO:4, modified to include a tyrosine at the C-terminus, has a long serum half-life. The peptide was radiolabelled with iodine and the amount of polypeptide in serum samples was determined. The results showed that the polypeptide had a terminal half-life of about 34 hours when administered intravenously and a terminal half-life of about 11 hours when administered intraperitoneally.

This example demonstrates that peptides of the invention have a long half-life in serum). An iodinated version of polypeptide of SEQ ID NO:4, which was modified to have a Y residue at the C-terminus, was administered intravenously to Sprague-Dawley rats. The kinetics reflected a biphasic elimination, which is typical of peptides. Following an initial elimination phase during the first 2.5 hours, with 4.5 hours half-life, a terminal half-life of approximately 34 hours was seen. This distribution pattern resembles what has been reported for ApoA-I and HDL. The half-life of the peptide when administered IP was calculated to be about 11.2 hours. (See, FIG. 23).

TABLE I

Pharmacokinetic parameters for IP administration.
Time interval, 0-30 hours.

| Parameter | SEQ ID NO: 4/Y26 peptide |
|---|---|
| Correlation | −1.00 |
| Half-live, hours | 11.2 |
| Residual AUC | 15.9 |
| Bioavailibility, % | 37.6 |

The bioavailability in percent was calculated from the area under the curve IP as divided by area under the curve IV after adjustment for residual activity and the bioavailability was about 40%.

TABLE II

Pharmacokinetic parameters for IV administration Interval 0-2.5 hours is taken as first phase and 2.5-24 hours as second phase.

| Parameter | SEQ ID NO: 4/Y26 0-2.5 hours | SEQ ID NO: 4/Y26 2.5-24 hours |
|---|---|---|
| Correlation | −0.95 | −0.95 |
| Half-live, hours | 4.5 | 33.7 |
| Clearance ml/kg/hour | | 1.2 |
| Volume of distribution ml/kg | | 55.7 |
| Residual AUC | | 61.5 |

The calculated distribution of volume is approximately twice as large as the plasma volume, indicating substantial extravascular distribution.

The exemplary data provided above, e.g., demonstrate that the polypeptides of the invention have a long half life and demonstrate their in vivo efficacy. Furthermore, toxicology studies show no signs of cell disruption or hemolysis in spite of exposure by injections of doses >10× therapeutic dose. By low non-specific cholesterol efflux and lack of detergent effects cell membrane stability is preserved in spite of potent cholesterol removal from cells.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. An isolated polypeptide having cholesterol efflux and ABCA1 stabilizing activity, wherein the peptide comprises an amphipathic α-helix segment $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$ having at least 60% identity to EVRSKLEEWFAAFRE-FAEEFLARL (SEQ ID NO:12); and $X_1, X_7, X_8, X_{15}, X_{18}$ and $X_{19}$ are amino acids independently selected from the group consisting of D and E.

2. The isolated polypeptide of claim 1, wherein the amino acid sequence has at least 70% identity to (SEQ ID NO: 12)
EVRSKLEEWFAAFREFAEEFLARL.

3. The isolated polypeptide of claim 1, wherein the polypeptide further comprises $X_{25}$ and $X_{26}$ at the carboxyl terminus, wherein $X_{25}$ is an amino acid independently selected from the group consisting of R, K, A, V, L, I, F, W, M, P, G, S, T, C, Y, N and Q, and $X_{26}$ is an amino acid independently selected from the group consisting of S, C, T, G, A, P and Y.

4. The isolated polypeptide of claim 3, wherein $X_{25}$ is K and $X_{26}$ is S.

5. The isolated polypeptide of claim 3, wherein $X_{25}$ or $X_{26}$ is C.

6. The isolated polypeptide of claim 1, wherein the polypeptide further comprises a protecting group.

7. The isolated polypeptide of claim 6, wherein the protecting group is a protecting group selected from the group consisting of acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-butyl (tBu), and trifluoroacetyl (TFA).

8. The isolated polypeptide of claim 6, wherein the protecting group is coupled to the amino or carboxy terminus.

9. The isolated polypeptide of claim 1, wherein the polypeptide comprises a first protecting group coupled to the amino terminus and a second protecting group coupled to the carboxyl terminus.

10. The isolated polypeptide of claim 9, wherein the first protecting group is a protecting group selected from the group consisting of acetyl, propionyl, and a 3 to 20 carbon alkyl.

11. The isolated polypeptide of claim 10, wherein the first protecting group is an acetyl.

12. The isolated polypeptide of claim 9, wherein the first protecting group is an acetyl and the second protecting group is an amide.

13. The isolated polypeptide of claim 1, wherein all enantiomeric amino acids are "D" amino acids.

14. The isolated polypeptide of claim 1, wherein enantiomeric amino acids are a mixture of "L" amino acids and "D" amino acids.

15. A composition comprising a polypeptide of claim 1 and a pharmaceutically acceptable carrier.

16. The composition of claim 15, further comprising a therapeutic agent for treating cardiovascular disease.

17. A composition comprising a polypeptide of claim 1 complexed with a lipid.

18. The composition of claim 17, wherein the lipid is a phospholipid.

19. The composition of claim 18, wherein the phospholipid is 1-palmitoyl-2-oleoyl-sn-glycerol-3-phosphatidylcholine ("POPC").

20. The composition of claim 17, further comprising a pharmaceutically acceptable carrier.

21. A method for mediating cholesterol efflux in a mammal, the method comprising administering to the mammal a polypeptide of claim 1, whereby cholesterol efflux is mediated.

22. A method for treating a symptom of atherosclerosis wherein the symptom is high levels of low density lipoprotein in a mammal, the method comprising administering to the mammal a therapeutically effective amount of a polypeptide of claim 1.

23. A method for stabilizing a vulnerable plaque in a lumen wall of a mammal, the method comprising administering to the mammal a polypeptide of claim 1.

24. A kit for treating atherosclerosis, the kit comprising a container containing a polypeptide of claim 1.

25. The kit of claim 24, further comprising a pharmaceutically acceptable carrier.

26. The kit of claim 24, wherein the polypeptide is combined with a pharmaceutically acceptable carrier in a unit dosage formulation.

27. A detectable affinity ligand comprising an isolated polypeptide of claim 1 directly or indirectly linked to a detectable moiety.

28. The isolated polypeptide of claim 1, wherein:
$X_2$ is an amino acid selected from the group consisting of F, V, L and W;
$X_6, X_9, X_{10}, X_{13}, X_{16}, X_{20}$ and $X_{24}$ are amino acids independently selected from the group consisting of L, F and W;

$X_4$, $X_{11}$, and $X_{22}$ are amino acids independently selected from the group consisting of S, A and Y; and
$X_{17}$ is an amino acid selected from the group consisting of F, A, L and W.

* * * * *

SEQUENCE LISTING

<160> NUMBER OF SEQ ID NOS: 20

<210> SEQ ID NO 1
<211> LENGTH: 24
<212> TYPE: PRT

```
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-

```
<210> SEQ ID NO 2
<211> LENGTH: 24
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A

```
<222> LOCATION: (17)...(17)
<223> OTHER INFORMATION: Xaa = Phe or Ala

<400> SEQUENCE: 3

Glu Xaa Arg Ser Lys Leu Glu Glu Trp Phe Ala Ala Phe Arg Glu Phe
1               5                   10                  15

Xaa Glu Glu Phe Leu Ala Arg Leu Lys Ser
            20                  25

<210> SEQ ID NO 4
<211> LENGTH: 26
<212> TYPE: PRT
<213> ORGANISM: Artificial Sequence
<220> FEATURE:
<223> OTHER INFORMATION: ATI-5261 amphipathic alpha-helix polypeptide
      core sequence selectively binds HDL, high-affinity ligand for
      ATP-binding cassette transporter A1 (ABCA1), ABCA1-lipid
      cholesterol efflux, ABCA1-stablization, anti-oxidant and anti-
      inflammatory activity

<400> SEQUENCE: 4

Glu Val Arg Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 5
<211> LENGTH: 26
<212> TYPE: PRT
<213> ORGANISM: Artificial Sequence
<220> FEATURE:
<223> OTHER INFORMATION: S1 amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity

<400> SEQUENCE: 5

Glu Val Arg Ser Lys Leu Glu Glu Trp Phe Ala Ala Phe Arg Glu Phe
1               5                   10                  15

Phe Glu Glu Phe Leu Ala Arg Leu Lys Ser
            20                  25

<210> SEQ ID NO 6
<211> LENGTH: 26
<212> TYPE: PRT
<213> ORGANISM: Artificial Sequence
<220> FEATURE:
<223> OTHER INFORMATION: S2 amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity

<400> SEQUENCE: 6

Glu Phe Arg Ser Lys Leu Glu Glu Trp Phe Ala Ala Phe Arg Glu Phe
1               5                   10                  15

Phe Glu Glu Phe Leu Ala Arg Leu Lys Ser
            20                  25

<210> SEQ ID NO 7
<211> LENGTH: 26
<212> TYPE: PRT
<213> ORGANISM: Artificial Sequence
<220> FEATURE:
<223> OTHER INFORMATION: S3 amphipathic alpha-helix polypeptide core
      sequence selectively binds HDL, high-affinity ligand for ATP-
```

-continued binding cassette transporter A1 (ABCA1), ABCA1-lipid cholesterol
efflux, ABCA1-stablization, anti-oxidant and anti-inflammatory
activity

<400> SEQUENCE: 7

Glu Phe Arg Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 8
<211> LENGTH: 26
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (1)...(1)
<223> OTHER INFORMATION: Xaa = Glu or Asp
<220> FEATURE:
<221> NAME/KEY: MOD_RES
<222> LOCATION: (2)...(2)
<223> OTHER INFORMATION: Xaa = Phe, Val, Leu or Trp
<220> FEATURE:
<221> NAME/KEY: MOD_RES
<222> LOCATION: (3)...(3)
<223> OTHER INFORMATION: Xaa = Arg or Lys
<220> FEATURE:
<221> NAME/KEY: MOD_RES
<222> LOCATION: (5)...(5)
<223> OTHER INFORMATION: Xaa = Arg or Lys
<220> FEATURE:
<221> NAME/KEY: MOD_RES
<222> LOCATION: (6)...(6)
<223> OTHER INFORMATION: Xaa = Leu, Phe or Trp
<220> FEATURE:
<221> NAME/KEY: MOD_RES
<222> LOCATION: (7)...(8)
<223> OTHER INFORMATION: Xaa = Glu or Asp
<220> FEATURE:
<221> NAME/KEY: MOD_RES
<222> LOCATION: (9)...(10)
<223> OTHER INFORMATION: Xaa = Leu, Phe or Trp
<220> FEATURE:
<221> NAME/KEY: MOD_RES
<222> LOCATION: (13)...(13)
<223> OTHER INFORMATION: Xaa = Leu, Phe or Trp
<220> FEATURE:
<221> NAME/KEY: MOD_RES
<222> LOCATION: (14)...(14)
<223> OTHER INFORMATION: Xaa = Arg or Lys
<220> FEATURE:
<221> NAME/KEY: MOD_RES
<222> LOCATION: (15)...(15)
<223> OTHER INFORMATION: Xaa = Glu or Asp
<220> FEATURE:
<221> NAME/KEY: MOD_RES
<222> LOCATION: (16)...(16)
<223> OTHER INFORMATION: Xaa = Leu, Phe or Trp
<220> FEATURE:
<221> NAME/KEY: MOD_RES
<222> LOCATION: (17)...(17)
<223> OTHER INFORMATION: Xaa = Phe, Ala, Leu or Trp
<220> FEATURE:
<221> NAME/KEY: MOD_RES
<222> LOCATION: (18)...(19)
<223> OTHER INFORMATION: Xaa = Glu or Asp
<220> FEATURE:
<221> NAME/KEY: MOD_RES
<222> LOCATION: (20)...(20)
<223> OTHER INFORMATION: Xaa = Leu, Phe or Trp

```
<220> FEATURE:
<221> NAME/KEY: MOD_RES
<222> LOCATION: (23)...(23)
<223> OTHER INFORMATION: Xaa = Arg or Lys
<220> FEATURE:
<221> NAME/KEY: MOD_RES
<222> LOCATION: (24)...(24)
<223> OTHER INFORMATION: Xaa = Leu, Phe or Trp

<400> SEQUENCE: 8

Xaa Xaa Xaa Ser Xaa Xaa Xaa Xaa Xaa Xaa Ala Ala Xaa Xaa Xaa Xaa
 1               5                  10                  15

Xaa Xaa Xaa Xaa Leu Ala Xaa Xaa Lys Ser
            20                  25

<210> SEQ ID NO 9
<211> LENGTH: 26
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (1)...(1)
<223> OTHER INFORMATION: Xaa = Glu or Asp
<220> FEATURE:
<221> NAME/KEY: MOD_RES
<222> LOCATION: (2)...(2)
<223> OTHER INFORMATION: Xaa = Phe or Val
<220> FEATURE:
<221> NAME/KEY: MOD_RES
<222> LOCATION: (3)...(3)
<223> OTHER INFORMATION: Xaa = Arg or Lys
<220> FEATURE:
<221> NAME/KEY: MOD_RES
<222> LOCATION: (5)...(5)
<223> OTHER INFORMATION: Xaa = Arg or Lys
<220> FEATURE:
<221> NAME/KEY: MOD_RES
<222> LOCATION: (7)...(8)
<223> OTHER INFORMATION: Xaa = Glu or Asp
<220> FEATURE:
<221> NAME/KEY: MOD_RES
<222> LOCATION: (14)...(14)
<223> OTHER INFORMATION: Xaa = Arg or Lys
<220> FEATURE:
<221> NAME/KEY: MOD_RES
<222> LOCATION: (15)...(15)
<223> OTHER INFORMATION: Xaa = Glu or Asp
<220> FEATURE:
<221> NAME/KEY: MOD_RES
<222> LOCATION: (17)...(17)
<223> OTHER INFORMATION: Xaa = Phe or Ala
<220> FEATURE:
<221> NAME/KEY: MOD_RES
<222> LOCATION: (18)...(19)
<223> OTHER INFORMATION: Xaa = Glu or Asp
<220> FEATURE:
<221> NAME/KEY: MOD_RES
<222> LOCATION: (23)...(23)
<223> OTHER INFORMATION: Xaa = Arg or Lys

<400> SEQUENCE: 9

Xaa Xaa Xaa Ser Xaa Leu Xaa Xaa Trp Phe Ala Ala Phe Xaa Xaa Phe
 1               5                  10                  15

Xaa Xaa Xaa Phe Leu Ala Xaa Leu Lys Ser
            20                  25

<210> SEQ ID NO 10
```

```
<211> LENGTH: 26
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (2)...(2)
<223> OTHER INFORMATION: Xaa = Phe or Val
<220> FEATURE:
<221> NAME/KEY: MOD_RES
<222> LOCATION: (17)...(17)
<223> OTHER INFORMATION: Xaa = Phe or Ala

<400> SEQUENCE: 10

Glu Xaa Arg Ser Lys Leu Glu Glu Trp Phe Ala Ala Phe Arg Glu Phe
 1               5                  10                  15

Xaa Glu Glu Phe Leu Ala Arg Leu Lys Ser
                20                  25

<210> SEQ ID NO 11
<211> LENGTH: 24
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (1)...(1)
<223> OTHER INFORMATION: Xaa = Glu or Asp
<220> FEATURE:
<221> NAME/KEY: MOD_RES
<222> LOCATION: (2)...(2)
<223> OTHER INFORMATION: Xaa = Ala, Val, Leu, Ile, Phe, Trp, Met or Pro
<220> FEATURE:
<221> NAME/KEY: MOD_RES
<222> LOCATION: (3)...(3)
<223> OTHER INFORMATION: Xaa = Arg, Lys, Ala, Val, Leu, Ile, Phe, Trp,
      Met, Pro, Gly,
      Ser, Thr, Cys, Tyr, Asn or Gln, where at least two of positions
      3, 5, 14 and 23 are Arg or Lys
<220> FEATURE:
<221> NAME/KEY: MOD_RES
<222> LOCATION: (4)...(4)
<223> OTHER INFORMATION: Xaa = Ser, Thr, Gly, Ala or Tyr
<220> FEATURE:
<221> NAME/KEY: MOD_RES
<222> LOCATION: (5)...(5)
<223> OTHER INFORMATION: Xaa = Arg, Lys, Ala, Val, Leu, Ile, Phe, Trp,
      Met, Pro, Gly, Ser, Thr, Cys, Tyr, Asn or Gln, where at least two
      of positions 3, 5, 14 and 23 are Arg or Lys
<220> FEATURE:
<221> NAME/KEY: MOD_RES
<222> LOCATION: (6)...(6)
<223> OTHER INFORMATION: Xaa = Ala, Val, Leu, Ile, Phe, Trp, Met or Pro
<220> FEATURE:
<221> NAME/KEY: MOD_RES
<222> LOCATION: (7)...(8)
<223> OTHER INFORMATION: Xaa = Glu or Asp
<220> FEATURE:
<221> NAME/KEY: MOD_RES
<222> LOCATION: (9)...(10)
<223> OTHER INFORMATION: Xaa = Ala, Val, Leu, Ile, Phe, Trp, Met or Pro
<220> FEATURE:
<221> NAME/KEY: MOD_RES
<222> LOCATION: (11)...(11)
<223> OTHER INFORMATION: Xaa = Ser, Thr, Gly, Ala or Tyr
<220> FEATURE:
```

<221> NAME/KEY: MOD_RES
<222> LOCATION: (12)...(13)
<223> OTHER INFORMATION: Xaa = Ala, Val, Leu, Ile, Phe, Trp, Met or Pro
<220> FEATURE:
<221> NAME/KEY: MOD_RES
<222> LOCATION: (14)...(14)
<223> OTHER INFORMATION: Xaa = Arg, Lys, Ala, Val, Leu, Ile, Phe, Trp, Met, Pro, Gly, Ser, Thr, Cys, Tyr, Asn or Gln, where at least two of positions 3, 5, 14 and 23 are Arg or Lys
<220> FEATURE:
<221> NAME/KEY: MOD_RES
<222> LOCATION: (15)...(15)
<223> OTHER INFORMATION: Xaa = Glu or Asp
<220> FEATURE:
<221> NAME/KEY: MOD_RES
<222> LOCATION: (16)...(17)
<223> OTHER INFORMATION: Xaa = Ala, Val, Leu, Ile, Phe, Trp, Met or Pro
<220> FEATURE:
<221> NAME/KEY: MOD_RES
<222> LOCATION: (18)...(19)
<223> OTHER INFORMATION: Xaa = Glu or Asp
<220> FEATURE:
<221> NAME/KEY: MOD_RES
<222> LOCATION: (20)...(21)
<223> OTHER INFORMATION: Xaa = Ala, Val, Leu, Ile, Phe, Trp, Met or Pro
<220> FEATURE:
<221> NAME/KEY: MOD_RES
<222> LOCATION: (22)...(22)
<223> OTHER INFORMATION: Xaa = Ser, Thr, Gly, Ala or Tyr
<220> FEATURE:
<221> NAME/KEY: MOD_RES
<222> LOCATION: (23)...(23)
<223> OTHER INFORMATION: Xaa = Arg, Lys, Ala, Val, Leu, Ile, Phe, Trp, Met, Pro, Gly, Ser, Thr, Cys, Tyr, Asn or Gln, where at least two of positions 3, 5, 14 and 23 are Arg or Lys
<220> FEATURE:
<221> NAME/KEY: MOD_RES
<222> LOCATION: (24)...(24)
<223> OTHER INFORMATION: Xaa = Ala, Val, Leu, Ile, Phe, Trp, Met or Pro

<400> SEQUENCE: 11

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 12
<211> LENGTH: 24
<212> TYPE: PRT
<213> ORGANISM: Artificial Sequence
<220> FEATURE:
<223> OTHER INFORMATION: amphipathic alpha-helix polypeptide core sequence selectively binds HDL, high-affinity ligand for ATP-binding cassette transporter A1 (ABCA1), ABCA1-lipid cholesterol efflux, ABCA1-stablization, anti-oxidant and anti-inflammatory activity

<400> SEQUENCE: 12

Glu Val Arg Ser Lys Leu Glu Glu Trp Phe Ala Ala Phe Arg Glu Phe
 1               5                  10                  15

Ala Glu Glu Phe Leu Ala Arg Leu
            20

<210> SEQ ID NO 13
<211> LENGTH: 24
<212> TYPE: PRT
<213> ORGANISM: Artificial Sequence
<220> FEATURE:
<223> OTHER INFORMATION: amphipathic alpha-helix polypeptide core sequence selectively binds HDL, high-affinity ligand for ATP-binding cassette transporter A1 (ABCA1), ABCA1-lipid cholesterol efflux, ABCA1-stablization, anti-oxidant and anti-inflammatory activity

<400> SEQUENCE: 13

Glu Val Arg Ser Lys Leu Glu Glu Trp Phe Ala Ala Phe Arg Glu Phe
1               5                   10                  15

Phe Glu Glu Phe Leu Ala Arg Leu
            20

<210> SEQ ID NO 14
<211> LENGTH: 24
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity

<400> SEQUENCE: 14

Glu Phe Arg Ser Lys Leu Glu Glu Trp Phe Ala Ala Phe Arg Glu Phe
1               5                   10                  15

Phe Glu Glu Phe Leu Ala Arg Leu
            20

<210> SEQ ID NO 15
<211> LENGTH: 24
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity

<400> SEQUENCE: 15

Glu Phe Arg Ser Lys Leu Glu Glu Trp Phe Ala Ala Phe Arg Glu Phe
1               5                   10                  15

Ala Glu Glu Phe Leu Ala Arg Leu
            20

<210> SEQ ID NO 16
<211> LENGTH: 18
<212> TYPE: PRT
<213> ORGANISM: Artificial Sequence
<220> FEATURE:
<223> OTHER INFORMATION: portion of ATI-5261 amphipathic alpha-helix
      polypeptide core sequence

<400> SEQUENCE: 16

Glu Val Arg Ser Lys Leu Glu Glu Trp Phe Ala Ala Phe Arg Glu Phe
1               5                   10                  15

Ala Glu

<210> SEQ ID NO 17
<211> LENGTH: 26
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (1)...(1)

```
<223> OTHER INFORMATION: Xaa includes, but not limited to, Glu or Asp
<220> FEATURE:
<221> NAME/KEY: MOD_RES
<222> LOCATION: (2)...(2)
<223> OTHER INFORMATION: Xaa includes, but not limited to, Phe, Val,
      Leu or Trp
<220> FEATURE:
<221> NAME/KEY: MOD_RES
<222> LOCATION: (3)...(3)
<223> OTHER INFORMATION: Xaa includes, but not limited to, Arg or Lys
<220> FEATURE:
<221> NAME/KEY: MOD_RES
<222> LOCATION: (5)...(5)
<223> OTHER INFORMATION: Xaa includes, but not limited to, Arg or Lys
<220> FEATURE:
<221> NAME/KEY: MOD_RES
<222> LOCATION: (6)...(6)
<223> OTHER INFORMATION: Xaa includes, but not limited to, Leu, Phe or
      Trp
<220> FEATURE:
<221> NAME/KEY: MOD_RES
<222> LOCATION: (7)...(8)
<223> OTHER INFORMATION: Xaa includes, but not limited to, Glu or Asp
<220> FEATURE:
<221> NAME/KEY: MOD_RES
<222> LOCATION: (9)...(10)
<223> OTHER INFORMATION: Xaa includes, but not limited to, Leu, Phe or
      Trp
<220> FEATURE:
<221> NAME/KEY: MOD_RES
<222> LOCATION: (13)...(13)
<223> OTHER INFORMATION: Xaa includes, but not limited to, Leu, Phe or
      Trp
<220> FEATURE:
<221> NAME/KEY: MOD_RES
<222> LOCATION: (14)...(14)
<223> OTHER INFORMATION: Xaa includes, but not limited to, Arg or Lys
<220> FEATURE:
<221> NAME/KEY: MOD_RES
<222> LOCATION: (15)...(15)
<223> OTHER INFORMATION: Xaa includes, but not limited to, Glu or Asp
<220> FEATURE:
<221> NAME/KEY: MOD_RES
<222> LOCATION: (16)...(16)
<223> OTHER INFORMATION: Xaa includes, but not limited to, Leu, Phe or
      Trp
<220> FEATURE:
<221> NAME/KEY: MOD_RES
<222> LOCATION: (17)...(17)
<223> OTHER INFORMATION: Xaa includes, but not limited to, Phe, Ala,
      Leu or Trp
<220> FEATURE:
<221> NAME/KEY: MOD_RES
<222> LOCATION: (18)...(19)
<223> OTHER INFORMATION: Xaa includes, but not limited to, Glu or Asp
<220> FEATURE:
<221> NAME/KEY: MOD_RES
<222> LOCATION: (20)...(20)
<223> OTHER INFORMATION: Xaa includes, but not limited to, Leu, Phe or
      Trp
<220> FEATURE:
<221> NAME/KEY: MOD_RES
<222> LOCATION: (23)...(23)
<223> OTHER INFORMATION: Xaa includes, but not limited to, Arg or Lys
<220> FEATURE:
<221> NAME/KEY: MOD_RES
<222> LOCATION: (24)...(24)
<223> OTHER INFORMATION: Xaa includes, but not limited to, Leu, Phe or
      Trp

<400> SEQUENCE: 17

Xaa Xaa Xaa Ser Xaa Xaa Xaa Xaa Xaa Xaa Ala Ala Xaa Xaa Xaa Xaa
 1               5                   10                  15

Xaa Xaa Xaa Xaa Leu Ala Xaa Xaa Lys Ser
            20                  25
```

```
<210> SEQ ID NO 18
<211> LENGTH: 26
<212> TYPE: PRT
<213> ORGANISM: Artificial Sequence
<220> FEATURE:
<223> OTHER INFORMATION: amphipathic alpha-helix polypeptide core
      sequence selectively binds HDL, high-affinity ligand for ATP-
      binding cassette transporter A1 (ABCA1), ABCA1-lipid cholesterol
      efflux, ABCA1-stablization, anti-oxidant and anti-inflammatory
      activity
<220> FEATURE:
<221> NAME/KEY: MOD_RES
<222> LOCATION: (1)...(1)
<223> OTHER INFORMATION: Xaa includes, but not limited to, Glu or Asp
<220> FEATURE:
<221> NAME/KEY: MOD_RES
<222> LOCATION: (2)...(2)
<223> OTHER INFORMATION: Xaa includes, but not limited to, Phe or Val
<220> FEATURE:
<221> NAME/KEY: MOD_RES
<222> LOCATION: (3)...(3)
<223> OTHER INFORMATION: Xaa includes, but not limited to, Arg or Lys
<220> FEATURE:
<221> NAME/KEY: MOD_RES
<222> LOCATION: (5)...(5)
<223> OTHER INFORMATION: Xaa includes, but not limited to, Arg or Lys
<220> FEATURE:
<221> NAME/KEY: MOD_RES
<222> LOCATION: (7)...(8)
<223> OTHER INFORMATION: Xaa includes, but not limited to, Glu or Asp
<220> FEATURE:
<221> NAME/KEY: MOD_RES
<222> LOCATION: (14)...(14)
<223> OTHER INFORMATION: Xaa includes, but not limited to, Arg or Lys
<220> FEATURE:
<221> NAME/KEY: MOD_RES
<222> LOCATION: (15)...(15)
<223> OTHER INFORMATION: Xaa includes, but not limited to, Glu or Asp
<220> FEATURE:
<221> NAME/KEY: MOD_RES
<222> LOCATION: (17)...(17)
<223> OTHER INFORMATION: Xaa includes, but not limited to, Phe or Ala
<220> FEATURE:
<221> NAME/KEY: MOD_RES
<222> LOCATION: (18)...(19)
<223> OTHER INFORMATION: Xaa includes, but not limited to, Glu or Asp
<220> FEATURE:
<221> NAME/KEY: MOD_RES
<222> LOCATION: (23)...(23)
<223> OTHER INFORMATION: Xaa includes, but not limited to, Arg or Lys

<400> SEQUENCE: 18

Xaa Xaa Xaa Ser Xaa Leu Xaa Xaa Trp Phe Ala Ala Phe Xaa Xaa Phe
 1               5                  10                  15

Xaa Xaa Xaa Phe Leu Ala Xaa Leu Lys Ser
            20                  25

<210> SEQ ID NO 19
<211> LENGTH: 6
<212> TYPE: PRT
<213> ORGANISM: Artificial Sequence
<220> FEATURE:
<223> OTHER INFORMATION: Factor Xa cleavage site, enzymatic cleavage
      sequence

<400> SEQUENCE: 19

Met His Ile Glu Gly Arg
 1               5

<210> SEQ ID NO 20
<211> LENGTH: 26
<212> TYPE: PRT
<213> ORGANISM: Artificial Sequence
<220> FEATURE:
```

```
<223> OTHER INFORMATION: inverted peptide, ATI-5261 in reverse order

<400> SEQUENCE: 20

Ser Lys Leu Arg Ala Leu Phe Glu Glu Ala Phe Glu Arg Phe Ala Ala
1               5                   10                  15

Phe Trp Glu Glu Leu Lys Ser Arg Val Glu
            20                  25
```